(12) United States Patent
Graef et al.

(10) Patent No.: US 10,278,929 B2
(45) Date of Patent: May 7, 2019

(54) IDENTIFICATION OF STABILIZERS OF MULTIMERIC PROTEINS

(71) Applicant: The Board of Trustees of the Leland Stanford Junior University, Stanford, CA (US)

(72) Inventors: Isabella A. Graef, Woodside, CA (US); Mamoun M. Alhamadsheh, Fremont, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/936,159

(22) Filed: Mar. 26, 2018

(65) Prior Publication Data

US 2019/0054040 A1 Feb. 21, 2019

Related U.S. Application Data

(63) Continuation of application No. 15/092,446, filed on Apr. 6, 2016, now Pat. No. 10,039,726, which is a continuation of application No. 14/531,888, filed on Nov. 3, 2014, now Pat. No. 9,308,209, which is a continuation of application No. 13/696,505, filed as application No. PCT/US2011/035350 on May 5, 2011, now Pat. No. 8,877,795.

(60) Provisional application No. 61/332,638, filed on May 7, 2010.

(51) Int. Cl.
| | |
|---|---|
| *A61K 31/12* | (2006.01) |
| *A61K 31/519* | (2006.01) |
| *A61K 31/4196* | (2006.01) |
| *A61K 31/433* | (2006.01) |
| *A61K 31/428* | (2006.01) |
| *C07D 231/12* | (2006.01) |
| *C07D 487/04* | (2006.01) |
| *A61K 31/166* | (2006.01) |
| *G01N 21/64* | (2006.01) |

(52) U.S. Cl.
CPC ............ *A61K 31/12* (2013.01); *A61K 31/166* (2013.01); *A61K 31/4196* (2013.01); *A61K 31/428* (2013.01); *A61K 31/433* (2013.01); *A61K 31/519* (2013.01); *C07D 231/12* (2013.01); *C07D 487/04* (2013.01); *G01N 21/6428* (2013.01)

(58) Field of Classification Search
CPC .................................................... A61K 31/12
See application file for complete search history.

(56) References Cited

U.S. PATENT DOCUMENTS

| | | | |
|---|---|---|---|
| 4,255,329 A | 3/1981 | Ullman | |
| 4,657,914 A | 4/1987 | Bernardi et al. | |
| 4,668,640 A | 5/1987 | Wang et al. | |
| 5,315,015 A | 5/1994 | Hui et al. | |
| 5,521,202 A | 5/1996 | Yano et al. | |
| 7,560,488 B2 | 7/2009 | Kelly et al. | |
| 7,598,269 B2 | 10/2009 | Kong et al. | |
| 7,763,747 B2 | 7/2010 | Snow | |
| 8,877,795 B2 | 11/2014 | Graef et al. | |
| 9,169,214 B2 | 10/2015 | Graef et al. | |
| 9,308,209 B2 | 4/2016 | Graef et al. | |
| 10,039,726 B2 * | 8/2018 | Graef ................. | A61K 31/4196 |
| 2006/0160796 A1 | 7/2006 | Pfahl et al. | |
| 2006/0183792 A1 | 8/2006 | Fobare et al. | |
| 2009/0247547 A1 | 10/2009 | Shultz et al. | |

FOREIGN PATENT DOCUMENTS

| | | |
|---|---|---|
| WO | WO2004096808 | 11/2004 |
| WO | WO2006009826 | 1/2006 |
| WO | WO2008016811 | 2/2008 |
| WO | WO2008077597 | 7/2008 |
| WO | WO2008141020 | 11/2008 |
| WO | WO2008154241 | 12/2008 |
| WO | WO2009148961 | 12/2009 |
| WO | WO2010010190 | 1/2010 |
| WO | WO2010030592 | 3/2010 |

OTHER PUBLICATIONS

Adamski-Werner et al. (2004) "Diflunisal Analogues Stabilize the Native State of Transthyretin. Potent Inhibition of Amyloidogenesis" J Med Chem, 47(2):355-374.
Aldred et al. (1995) "The cerebral expression of plasma protein genes in different species" Comp Biochem Physiol B Biochem Mol Biol, 111(1):1-15.
Bartalena and Robbins (1993) "Thyroid hormone transport proteins" Clin Lab Med,13(3):583-598.
Blake et al. (1978) "Structure of prealbumin: Secondary, tertiary and quaternary Interactions determined by Fourier refinement at 1.8 Å" J Mol Biol, 121(3):339-356.
Baures et al (1998): STN International HCAPLUS database, (Columbus, Ohio), Accession No. 1998:617889.
Buxbaum et al. (2008) "Transthyretin protects Alzheimer's mice from the behavioral and biochemical effects of Aβ toxicity" Proc Natl Acad Sci, 105(7):2681-2686.

(Continued)

*Primary Examiner* — Golam M Shameem
(74) *Attorney, Agent, or Firm* — Edward J. Baba; Bozicevic, Field & Francis LLP

(57) ABSTRACT

Disclosed herein are compounds and compositions thereof which find use in increasing stability of TTR tetramers reducing its tendency to misfold and form aggregates. Also provided herein are methods for using these compounds and compositions for increasing stability of TTR and thereby decreasing aggegate formation by TTR. Also disclosed herein are methods to screen for candidate compounds that increase stability of TTR. Also disclosed herein are heterobifunctional compounds that include a TTR binding compound connected to a targeting moiety via a linker, for use in disrupting PPis of a target protein.

18 Claims, 24 Drawing Sheets

(56) References Cited

OTHER PUBLICATIONS

Chang et al. (1999) "Evolution of thyroid hormone binding by transthyretins in birds and mammals," Eur J Biochem, 259:534-542.
Choi et al. (2007) "Accelerated Aβ Deposition in APPswe/PS1ΔE9 Mice with Hemizygous Deletions of TTR(Transthyretin)" J Neurosci, 27(26):7006-7010.
Connelly et al. (2010) "Structure-based design of kinetic stabilizers that ameliorate the transthyretin amyloidosis" Current Opinion in Structural Biology, Elsevier Ltd., GB 20(1):54-62.
Emerson et al. (2003) "NMR characterization of interleukin-2 in complexes with the IL-2Ralpha receptor component, and with low molecular weight compounds that inhibit the IL-2/IL-Ralpha interaction" Protein Sci,12(4):811-822.
Farr et al (2001): STN International HCAPLUS database, (Columbus, Ohio), Accession No. 2001:338762.
He et al. (2005) "Small-molecule inhibition of TNF-alpha." Science, 310(5750):1022-1025.
Hull et al. (2004) "Islet amyloid: a critical entity in the pathogenesis of type 2 diabetes" J. Clin. Endocrinol & Metab, 89(8):3629-3643.
Johnson et al. (2005) "Native State Kinetic Stabilization as a Strategy to Ameliorate Protein Misfolding Diseases: A Focus on the Transthyretin Amyloidoses" Acc Chem Res, 38(12):911-921.
Koehler et al. (2003) "Discovery of an inhibitor of a transcription factor using small molecule microarrays and diversity-oriented synthesis" J Am Chem Soc, 125(28):8420-8421.

Maher et al. (1992) "Synthesis of some new 3-(2'-heterocyclicethyl)-2-methyl-3,4-dihydroquinazolin-4-one derivatives as antimicrobial agents" J Chem Tech & Biotech, 55(3):209-215.
Monaco et al. (1995) "Structure of a complex of two plasma proteins: transthyretin and retinol-binding protein" Science, 268(5231):1039-1047.
Peterson et al. (1998) "Inhibiting transthyretin conformational changes that lead to amyloid fibril formation" Proc Natl Acad Sci USA, 95(22):12956-12960.
Prapunpoj et al. (2006) "Change in structure of the N-terminal region of transthyretin produces change in affinity of transthyretin to T4 and T3" FEBS J 273(17):4013-4023.
Rickert et al. (2005) "The Structure of Interleukin-2 Complexed with its Alpha Receptor" Science, 308(5727):1477-1480.
Sekijima et al. (2008) "Pathogenesis of and Therapeutic Strategies to Ameliorate the Transthyretin Amyloidoses" Curr Pharm Des 14(30):3219-3230.
Suhr et al. (2000) "Liver Transplantation for Hereditary Transthyretin Amyloidosis" Transpl, 6(3):263-276.
Wiseman et al. (2005) "Kinetic Stabilization of an Oligomeric Protein by a Single Ligand Binding Event" Am Chem Soc, 127:5540-5551.
Yamauchi et al (2003): STN International HCAPLUS database, (Columbus, Ohio), Accession No. 2003:155526.

\* cited by examiner

IDENTIFICATION OF STABILIZERS OF MULTIMERIC PROTEINS

CROSS-REFERENCE

This application is a continuation of U.S. patent application Ser. No. 15/092,446, filed on Apr. 6, 2016, now U.S. Pat. No. 10,039,726, which is a continuation of U.S. patent application Ser. No. 14/531,888, filed Nov. 3, 2014, now U.S. Pat. No. 9,308,209, which is a continuation of U.S. patent Ser. No. 13/696,505, now U.S. Pat. No. 8,877,795, which is a 371 of PCT/US2011/035350, filed May 5, 2011, which claims the benefit of U.S. Provisional Patent Application No. 61/332,638, filed May 7, 2010, which applications are incorporated herein by reference in their entirety.

STATEMENT REGARDING FEDERALLY SPONSORED RESEARCH

This invention was made with government support under Grant No. PN2 EY016525 awarded by National Institute of Health. The government has certain rights in this invention.

INTRODUCTION

Targeting protein protein interactions (PPIs) is of therapeutic interest. To date approved inhibitors of PPIs are proteins rather than small-molecule inhibitors. For example, therapeutic monoclonal antibodies (mAbs) are used in treating cancer, autoimmune, infectious and neurodegenerative diseases. Therapeutic mAbs are costly to manufacture, they require administration by injection and can illicit an immune-response in the patient. For these reasons the development of small-molecule inhibitors of PPIs is of interest.

The cytokine tumor-necrosis factor alpha (TNF-α) plays an important role in the inflammatory response to tissue injury and various viral and bacterial infections. TNF-α forms homotrimers, which bind to the TNF-α receptors 1 and 2 and induce receptor trimerization. Depending on the cellular context, trimerization of the TNF receptor 1 (TNFR1) can lead to activation of the immune system by the NFκB signaling pathway. Since aberrantly increased TNF-α activity may also lead to tissue damage, inhibitors of TNF-α are of clinical interest for the treatment of autoimmune diseases, such as rheumatoid arthritis or Crohn's disease. These pathological conditions are currently being treated with anti-TNF-α antibodies and soluble receptor molecules, which act by sequestering TNF-α. Neutralising anti-TNF-α antibodies and soluble TNF receptor preparations have anti-inflammatory activities in clinical studies, particularly in rheumatoid arthritis. TNF-α also activates osteoclasts both by itself and in synergy with RANKL and is a target for the treatment of bone disorders such as osteoporosis. Inhibition of the interaction between TNF-α and its receptor TNFR1 using hetero-bifunctional molecules is of interest for inhibition of TNF-α activity.

Interleukin-2 (IL-2) is a 15.5 kD cytokine that has a predominant role in the growth of activated T cells. IL-2 stimulates T-cell proliferation by binding on the T-cell surface with picomolar affinity to a heterotrimeric receptor complex consisting of α, β, and γ chains. The IL2/IL-2Rα interaction is a target for therapeutic modulation because the IL2Rα is not expressed on resting T and B cells but is continuously expressed by the abnormal T cells of patients with forms of leukemia, autoimmunity, and organ transplant rejection. Antibodies that recognize the a receptor subunit (IL-2Rα) and block IL-2 binding are clinically effective as immunosuppressive agents. Inhibition of the interaction between IL-2 and IL-2Ra using hetero-bifunctional molecules is of interest for inhibition of IL-2 activity.

The deposition of a normally soluble protein into amyloid fibrils is a hallmark of human amyloid diseases. Conformational changes are sufficient for the conversion of a number of normally soluble human proteins into amyloid fibrils, including the immunoglobulin light chains, lysozyme, and transthyretin (TTR), and variants thereof. Fibril formation is believed to be intimately involved in the pathological mechanism of human amyloid disease based on the demonstrated neurotoxicity of amyloid fibrils produced in vitro, the observation of lower levels of amyloid in age-matched controls relative to Alzheimer disease patients, and the correlation of improved health with the clearance of amyloid in Familial Amyloid polyneuropathy (FAP) patients, where liver transplantation is used to replace mutant TTR with wild-type TTR.

There is an interest in identifying ways to prevent the conformational changes that result in the formation of amyloid fibrils. In the case of TTR, it has been determined that stabilizing TTR in its tetrameric form inhibits the formation of TTR amyloids.

Transthyretin (TTR or prealbumin) is a 55 kDa homotetrameric protein present in blood and cerebrospinal fluid. TTR is primarily synthesized in the liver. TTR transports holoretinol binding protein (RBP) and L-thyroxine (T4) in the blood and cerebrospinal fluid. The misfolding of wild type TTR (WT-TTR) or one of >100 different mutated variants, through dissociation to non-native monomeric intermediates that aggregate and polymerize into amyloid fibrils, is associated with various TTR amyloid diseases.

Several classes of small molecules have been reported to inhibit TTR amyloid formation by binding to the T4-binding sites in TTR and kinetically stabilizing its quaternary structure. TTR has two identical funnel-shaped T4-binding sites located at its dimer-dimer interface. TTR is abundant in plasma (1.8-5.4 µM tetramer concentration) and small molecule binders of TTR should not compete with the natural ligand (T4) as <1% of TTR in the plasma is typically bound to T4. Recently, Tafamidis, a TTR kinetic stabilizer, completed a successful phase II/III clinical trials for FAP. The nonsteroidal anti-inflammatory drug (NSAID) diflunisal also showed promising results in clinical trial for FAP.

Most of the other TTR stabilizers reported are structurally based on typical biaryl and halogenated biaryl analogues of T4 and NSAID-like compounds, respectively.

There is a need for discovery of TTR kinetic stabilizers.

SUMMARY

Disclosed herein are compounds and compositions thereof which find use in increasing stability of proteins particularly proteins that tend to misfold and form aggregates. Also provided herein are methods for using these compounds and compositions for increasing stability of proteins and thereby decreasing aggregate formation by these proteins. Also disclosed herein are methods to screen for candidate compounds that increase stability of proteins. Also disclosed herein are heterobifunctional compounds that include a TTR binding compound connected to a targeting moiety via a linker, for use in disrupting PPIs of a target protein.

BRIEF DESCRIPTION OF THE DRAWINGS

(FIG. 1B) $K_d$ for 1=72.5±4.7 nM. (FIG. 1C) $K_d$ for 2>3289 nM nM. (FIG. 1D) $K_d$ for 4=284.9±58.1 nM. (FIG. 1E) $K_d$ for diclofenac=370.4±145.4 nM). Raw data (top) and integrated heats (bottom) from the titration of TTR (2 µM) with ligands (25 µM). The solid red line through the integrated heats represents the best fit binding isotherm to a one-to-one binding model.

(FIG. 2A) calorimetric titration of 5 against TTR ($K_d$=819.7±129.7 nM). Raw data (top) and integrated heats (bottom) from the titration of TTR (2 µM) with probe 5 (25 µM). The solid red line through the integrated heats represents the best fit binding isotherm to a one-to-one binding model. (FIG. 2B) Fluorescence polarization saturation binding between 5 (100 nM) and increasing concentration of TTR (5 nM to 10 µM) (FIG. 2C) Displacement of 5 from TTR by increasing concentration (10 nM-50 µM) of ligand 1 ($K_{app}$=0.231 µM, $R^2$=0.997). FP Assays were performed in triplicate and the error bars represent STDV.

(FIG. 3A) 2 ($K_{app}$>50 µM). (FIG. 3B) Thyroxine T4 ($K_{app}$=0.186 µM, $R^2$=0.998). (FIG. 3C) Diclofenac ($K_{app}$=4.66 µM, $R^2$=0.999).

(FIG. 5A) Percentage of TTR (3.6 µM) fibril formation in the presence of ligands (7.2 µM) relative to aggregation in the absence of ligands (denoted 100%) at 72 hours. (FIG. 5B) Comparison of TTR (3.6 µM) aggregation inhibition in the presence of substoichiometric amounts of ligands (3.0 µM) relative to diclofenac.

(FIG. 6C) V1221 TTR was pre-incubated in the absence (V1221 TTR) or presence of ligands for 24 h at 4° C. and then added to human AC16 cardiac cell culture. (FIG. 6D) WT TTR pre-incubated in the absence (WT TTR) or presence of ligands for 24 h at 4° C. and then added to human IM-32 neuroblastoma cell culture.

(FIG. 8A) SPR sensogram showing concentration-dependent binding of ligand Ro-41-0960 to wild type biotinylated TTR on a streptavidin-coupled surface over a concentration of 90 nM to 3 µM, in order of increasing RUs. Normalized RUs are plotted over a time course. (FIG. 8B) SPR sensogram for niflumic acid binding to TTR. Equilibrium binding analysis indicates a $K_d$ of 186.1±23.8 nM ($k_{on}$=2.81×10$^6$±3.6×10$^5$ M$^{-1}$ s$^{-1}$ and $k_{off}$=0.523±3.6×10$^{-6}$ s$^{-1}$) (SD). (FIG. 8C) SPR sensogram for diclofenac binding to TTR. Equilibrium binding analysis indicates a $K_d$ of 123.5±8.91 nM ($k_{on}$=8.18×10$^6$±5.9×10$^5$ M$^{-1}$ s$^{-1}$ and $k_{off}$=1.01±0.003 s$^{-1}$) (SD).

DEFINITIONS

Figure 1A:
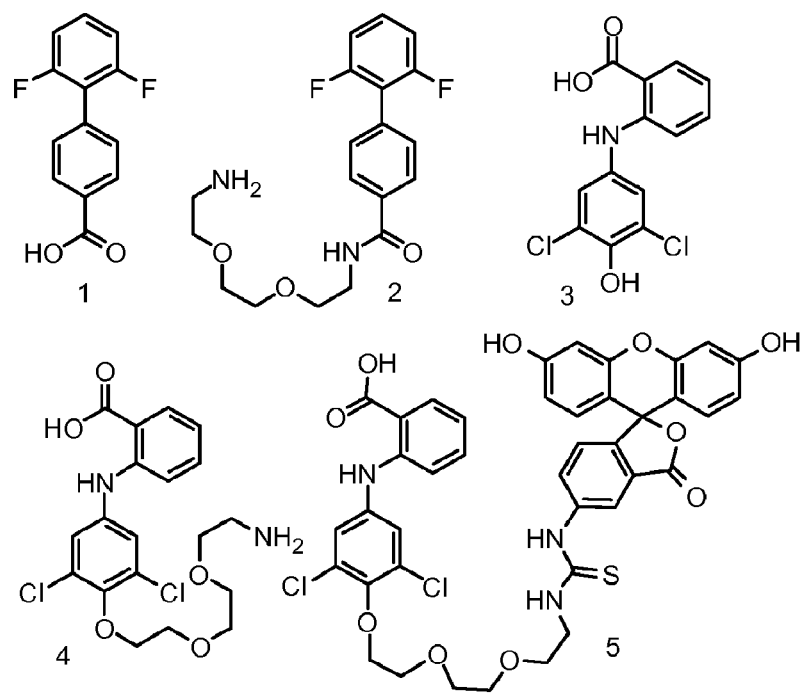
FIG. 1A depicts the structure of compounds 1-5.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature or during chemical synthesis. Isolated compounds are usually at least about 80% pure, or at least about 90% pure, at least about 98% pure, or at least about 99% pure, by weight. The present invention is meant to encompass diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject" and "patient" mean a mammal that may have a need for the pharmaceutical methods, compositions and treatments described herein. Subjects and patients thus include, without limitation, primate (including humans), canine, feline, ungulate (e.g., equine, bovine, swine (e.g., pig)), and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is preferably sterile, and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, isopropyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorometnyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

DETAILED DESCRIPTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that and in the appended claims, the singular forms "a," "an," and "the" include plural referents unless the context clearly dictates otherwise. Thus, for example, reference to "a method" includes a plurality of such methods and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -J, $=$W$-$, $-$X$=$, $=$Y$-$, $-$Z$=$, -Q, $-$R$^{V1}$, $-$R$^{V2}$, $-$R$^{V3}$, $-$R$^{V4}$, $-$R$^{T}$, $-$R$^{TT}$, -Q$^{CA}$, -Q$^{HA}$, $-$R$^{PP}$, $-$R$^{R}$, $-$R$^{RA}$, -L$^{R}$, -M$^{R}$, $-$R$^{R}$, $-$R$^{RR}$, $-$R$^{J}$, -M$^{J}$, $-$R$^{N}$, $-$R$^{J1}$, $-$R$^{J2}$, $-$R$^{J3}$, $-$R$^{J4}$, $-$R$^{J5}$, $-$R$^{J6}$, -L$^{J}$-, $-$R$^{J2XX}$, $-$R$^{JJ}$, $-$R$^{JJJ}$, L$^{JJJ}$-, $-$R$^{P2}$, $-$R$^{P3}$, $-$R$^{P4}$, $-$R$^{P5}$, $-$R$^{P6}$, $-$R$^{P2R}$, $-$R$^{P2RA}$, $-$R$^{P3R}$, $-$R$^{P3RA}$, $-$R$^{P4R}$, $-$R$^{P5R}$, $-$R$^{P5RA}$, $-$R$^{P6R}$, $-$R$^{P6RA}$, $-$R$^{AK}$, etc.) are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Overview

The present disclosure is based on the identification of compounds that bind to a TTR tetramer in the presence of a TTR ligand known to bind and stabilize TTR tetramer. These compounds stabilize TTR tetramers reducing the formation of TTR amyloid fibrils. These compounds find use in the preparation of heterobifunctional compounds that recruit TTR for use in disrupting PPIs.

The present disclosure also provides a method of identifying a ligand for TTR. Generally, the method uses a fluorescence polarization (FP)-probe comprising a ligand for TTR and a fluorescent moiety attached to the ligand by a linker. The FP probe binds to TTR to form a TTR-FP probe complex. The method includes: a) contacting a TTR-FP probe complex with a candidate compound, wherein the TTR-FP probe complex generates a FP signal; and b) determining the FP signal, wherein a decrease in the FP signal indicates the candidate compound binds to TTR and is a ligand for TTR.

Compositions

Provided herein are compounds that may be used to stabilize TTR tetramers reducing TTR amyloid fibril formation. These compounds can be incorporated into a variety of formulations for therapeutic administration by a variety of routes. More particularly, the compounds disclosed herein can be formulated into pharmaceutical compositions by combination with appropriate, pharmaceutically acceptable carriers, diluents, excipients and/or adjuvants. In most embodiments, the formulations are free of detectable DMSO (dimethyl sulfoxide), which is not a pharmaceutically acceptable carrier, diluent, excipient, or adjuvant.

Compounds

In some embodiments, a compound of the invention is of the structure of Formula I:

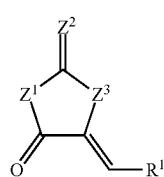

I where $R^1$ is an aryl or a heterocyclic group; and
$Z^1$, $Z^2$ and $Z^3$ are independently O, S, NH or $NR^2$, where $R^2$ is hydrogen, an alkyl or an aryl.

In some embodiments, a compound is of the structure of Formula I where:
$R^1$ is a phenyl, or a five-membered heterocyclic group;
$Z^1$ is NH;
$Z^2$ is NH or O; and
$Z^3$ is S or $NR^3$, where $R^3$ is lower alkyl.

In some embodiments, a compound of the invention is of the structure of Formula II:

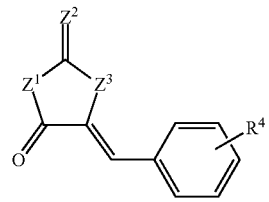

II where $Z^1$ is NH;
$Z^2$ is NH or O;
$Z^3$ is S or $NR^3$, where $R^3$ is lower alkyl; and
$R^4$ is one or more groups, each $R^4$ independently selected from hydrogen, an alkyl, an aryl, an alkoxy, an aryloxy, an acetyl, a carboxy, a formyl, an amido, a hydroxyl, a heterocyclic group, a halo, a nitro and a cyano, where optionally two or more $R^4$ groups may be cyclically linked. In some embodiments, in Formula II, $Z^1$ and $Z^2$ are NH and $Z^3$ is $NCH_3$.

In some embodiments, in the structure of Formula II at least one $R^4$ group is selected from a carboxy, a formyl and a hydroxy, and is attached at the 2-position of the phenyl ring. In some embodiments, in the structure of Formula II at least one $R^4$ group is selected from a carboxy, a formyl and a hydroxy, and is attached at the 3-position of the phenyl ring. In some embodiments, in the structure of Formula II at least one $R^4$ group is selected from a carboxy, a formyl and a hydroxy and is attached at the 4-position of the phenyl ring.

In some embodiments, a compound of the invention is of the structure of Formula III:

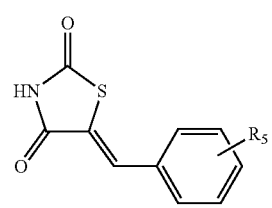

III where $R^5$ is one or more groups, each $R^5$ independently selected from hydrogen, an alkyl, an aryl, an alkoxy, an aryloxy, an acetyl, a carboxy, a formyl, an amido, a hydroxyl, a heterocyclic group, a halo, a nitro and a cyano, where optionally two or more $R^5$ groups may be cyclically linked. In some embodiments, in structure of Formula III, two $R^5$ groups on adjacent carbons of the ring may be cyclically linked to form a fused phenyl ring.

In some embodiments, a compound of the invention is of the structure of Formula III where:
$R^5$ is one or more groups, each $R^5$ independently selected from a benzyloxy group, a trifluoromethyl, a halo, a carboxy, a formyl, a lower alkyl, a hydroxyl, a lower alkoxy and a phenyl.

In some embodiments, in the structure of Formula III at least one $R^5$ group is selected from a carboxy, a formyl and a hydroxy, and is attached at the 2-position of the phenyl ring. In some embodiments, in the structure of Formula III at least one $R^5$ group is selected from a carboxy, a formyl and a hydroxy, and is attached at the 3-position of the phenyl ring. In some embodiments, in the structure of Formula III at least one $R^5$ group is selected from a carboxy, a formyl and a hydroxy and is attached at the 4-position of the phenyl ring.

In some embodiments, a compound of the invention is of the structure of Formula IV:

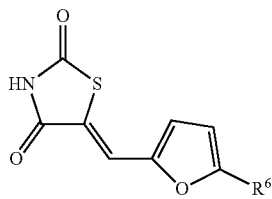

IV where $R^6$ is selected from hydrogen, an alkyl, an aryl, an alkoxy, an aryloxy, an acetyl, a carboxy, a formyl, an amido, a hydroxyl, a heterocyclic group, a halo, a nitro and a cyano.

In some embodiments, a compound of the invention is of the structure of Formula IV where $R^6$ is selected from a benzyloxy group, a trifluoromethyl, a bromo, a chloro, a methyl, a hydroxyl, a methoxy and a phenyl.

In some embodiments, a compound of the invention is of the structure of one of Formulas V, VI or VII:

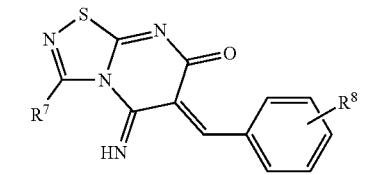

V

VI

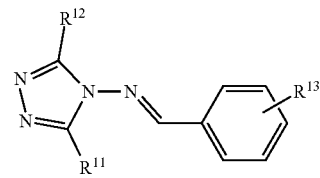

VII where $R^8$, $R^{10}$ and $R^{13}$ are independently one or more groups, each $R^8$, $R^{10}$ and $R^{13}$ independently selected from hydrogen, an alkyl, an aryl, an alkoxy, an aryloxy, an acetyl, a carboxy, a formyl, an amido, a hydroxyl, a heterocyclic group, a halo, a nitro and a cyano, where optionally two or more $R^8$, $R^{10}$ or $R^{13}$ groups may be cyclically linked; and $R^7$, $R^9$, $R^{11}$ and $R^{12}$ are independently selected from hydrogen, an alkyl, an aryl, an acetyl, a carboxy, a formyl, an amido, a sulfonyl, a sulfinyl, a thio, an acetyl and an amino.

In some embodiments, a compound of the invention is of the structure of one of Formulas V, VI or VII where $R^8$, $R^{10}$ and $R^{13}$ are independently one or more groups, each $R^8$, $R^{10}$ and $R^{13}$ independently selected from a benzyloxy group, a trifluoromethyl, a halo, a carboxy, a formyl, a methyl, a hydroxyl, a methoxy and a phenyl; and $R^7$, $R^9$, $R^{11}$ and $R^{12}$ are independently selected from methylsulfinyl, methylsulfonyl, a lower alkyl thioether, SH and a lower alkyl. In some embodiments, in Formula V, $R^7$ is —SCH$_3$ or —SO$_2$CH$_3$. In some embodiments, in Formula VI, $R^9$ is —SCH$_3$ or —SO$_7$CH$_3$.

In some embodiments, in the structure of one of Formulas V, VI and VII at least one $R^8$, $R^{10}$ or $R^{13}$ group is selected from a carboxy, a formyl and a hydroxy, and is attached at the 2-position of the phenyl ring. In some embodiments, in the structure of Formulas V, VI and VII at least one $R^8$, $R^{10}$ or $R^{13}$ group is selected from a carboxy, a formyl and a hydroxy, and is attached at the 3-position of the phenyl ring. In some embodiments, in the structure of Formulas V, VI and VII at least one $R^8$, $R^{10}$ or $R^{13}$ group is selected from a carboxy, a formyl and a hydroxy and is attached at the 4-position of the phenyl ring.

In some embodiments, a compound of the invention is of the structure of Formula VIII:

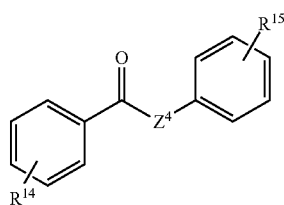

VIII where $Z^4$ is a single bond, a methylene, an aminomethylene, a hydroxymethylene or a linker of about 1 to 3 atoms in length; and $R^{14}$ and $R^{15}$ are independently one or more groups, each $R^{14}$ and $R^{15}$ group independently selected from hydrogen, an alkyl, an aryl, an alkoxy, an aryloxy, an acetyl, a carboxy, a formyl, an amido, a hydroxyl, a heterocyclic group, a halo, a nitro and a cyano, where optionally two or more $R^{14}$ or $R^{15}$ groups may be cyclically linked.

In some embodiments, a compound of the invention is of the structure of one of Formulas IX, X or XI:

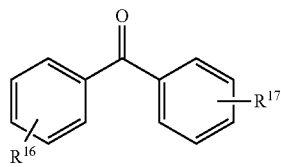

IX

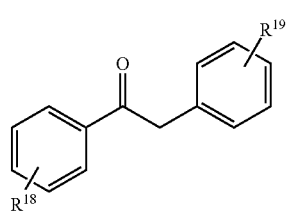

X

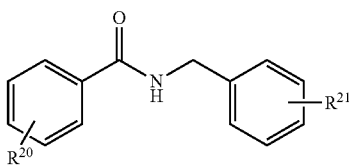

where $R^{16}$, $R^{17}$, $R^{18}$, $R^{19}$, $R^{20}$ and $R^{21}$ are independently one or more groups, each $R^{16}$, $R^{17}$, $R^{18}$, $R^{19}$, $R^{20}$ and $R^{21}$ group independently selected from hydrogen, an alkyl, an aryl, an alkoxy, an aryloxy, an acetyl, a carboxy, a formyl, an amido, a hydroxyl, a heterocyclic group, a halo, a nitro and a cyano, where optionally two or more $R^{16}$, $R^{17}$, $R^{18}$, $R^{19}$, $R^{20}$ or $R^{21}$ groups may be cyclically linked.

In some embodiments, a compound of the invention is of the structure of one of Formulas IX, X or XI where $R^{16}$, $R^{17}$, $R^{18}$, $R^{19}$, $R^{20}$ and $R^{21}$ are independently one or more groups, each $R^{16}$, $R^{17}$, $R^{18}$, $R^{19}$, $R^{20}$ and $R^{21}$ group independently selected from a lower alkoxy, a trifluoromethyl, a carboxy, a formyl, a lower alkyl, a hydroxyl, a nitro and a halo.

In some embodiments, in the structure of one of Formulas VIII, IX, X and XI at least one $R^{14}$, $R^{15}$, $R^{16}$, $R^{17}$, $R^{18}$, $R^{19}$, $R^{20}$ or $R^{21}$ group is selected from a carboxy, a formyl and a hydroxy, and is attached at the 2-position of the phenyl ring. In some embodiments, in the structure of one of Formulas VIII, IX, X and XI at least one $R^{14}$, $R^{15}$, $R^{16}$, $R^{17}$, $R^{18}$, $R^{19}$, $R^{20}$ or $R^{21}$ group is selected from a carboxy, a formyl and a hydroxy, and is attached at the 3-position of the phenyl ring. In some embodiments, in the structure of Formulas VIII, IX, X and XI at least one $R^{14}$, $R^{15}$, $R^{16}$, $R^{17}$, $R^{18}$, $R^{19}$, $R^{20}$ or $R^{21}$ group is selected from a carboxy, a formyl and a hydroxy and is attached at the 4-position of the phenyl ring.

In some embodiments, a compound of the invention is of the structure of Formula XII:

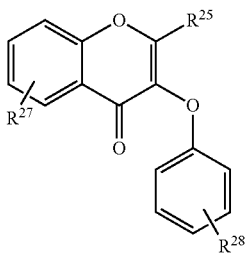

where $R^{25}$ is independently selected from hydrogen, an alkyl, a heterocyclic group, an aryl, a thio, cyano, an alkoxy, an aryloxy, a halo, and a hydroxyl; and $R^{27}$ and $R^{28}$ are independently one or more groups, each $R^{27}$ and $R^{28}$ independently selected from hydrogen, an alkyl, an aryl, an alkoxy, an aryloxy, an acetyl, a carboxy, a formyl, an amido, a hydroxyl, a heterocyclic group, a halo, a nitro and a cyano, where optionally two or more $R^{27}$ or $R^{28}$ groups may be cyclically linked.

In some embodiments, in the structure of Formula XII at least one $R^{27}$ or $R^{28}$ group is selected from a carboxy, a formyl and a hydroxy, and is attached at the 2-position of the phenyl ring. In some embodiments, in the structure of one of Formula XII at least one $R^{27}$ or $R^{28}$ group is selected from a carboxy, a formyl and a hydroxy, and is attached at the 3-position of the phenyl ring. In some embodiments, in the structure of Formula XII at least one $R^{27}$ or $R^{28}$ group is selected from a carboxy, a formyl and a hydroxy and is attached at the 4-position of the phenyl ring.

In some embodiments, a compound of the invention is of the structure of Formula XIII:

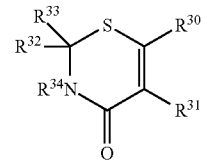

where $R^{30}$ and $R^{31}$ are independently selected from a hydrogen, an alkyl, a heterocyclic group, an aryl, a thio, cyano, an alkoxy, an aryloxy, a halo and a hydroxyl;

$R^{32}$ and $R^{33}$ are independently selected from hydrogen, an alkyl, a heterocyclic group and an aryl; and $R^{34}$ is selected from hydrogen, an alkyl, a heterocyclic group and an aryl, where optionally $R^{34}$ and $R^{32}$ may be cyclically linked to form a fused 6-membered ring.

In some embodiments, a compound is of the structure of Formula XIII where $R^{30}$ and $R^{31}$ are independently selected from cyano and benzylthio; $R^{32}$ and $R^{33}$ are independently selected from a hydrogen, an alkyl, a heterocyclic group and an aryl; and $R^{34}$ is hydrogen.

In some embodiments, a compound of the invention is of the structure of Formula XIV:

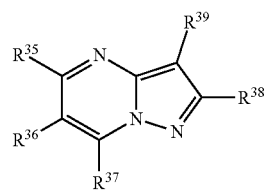

where $R^{35}$, $R^{36}$, $R^{37}$, $R^{38}$ and $R^{39}$ are independently selected from hydrogen, an alkyl, an aryl, an acetyl, a carboxy, a formyl, an amido, a heterocyclic group, a thio, cyano, a nitro, an alkoxy, an aryloxy, a halo and a hydroxyl.

In some embodiments, a compound of the invention is of the structure of Formula XIV where one of $R^{38}$ and $R^{39}$ is CO—$R^{40}$ where $R^{40}$ is selected from hydrogen, hydroxyl, an alkyl, an aryl, an amino and an alkoxy; and the other of $R^{38}$ and $R^{39}$ is selected from a hydrogen, an alkyl, an aryl, a heterocyclic group, a thio, cyano, a nitro, an alkoxy, an aryloxy, a halo and a hydroxyl.

In some embodiments, a compound of the invention is of the structure of one of Formulas XV and XVI:

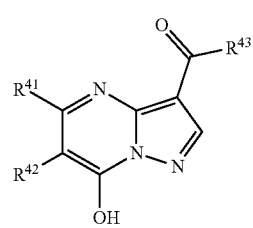

-continued

XVI where $R^{41}$ and $R^{42}$ are as defined above for $R^{35}$ and $R^{36}$; and $R^{43}$ is hydrogen, an amino or hydroxyl.

In some embodiments, a compound of the invention is of the structure of Formula XVII:

XVII where L is a linker of about 1 to 8 atoms in length;

$R^{51}$ and $R^{52}$ are selected from hydrogen, an alkyl, an aryl, an alkoxy, an aryloxy, a hydroxyl, a heterocyclic group, a halo, a nitro and a cyano;

$R^{53}$ is selected from hydrogen, an alkyl, an aryl and a heterocyclic group; and $R^{54}$ is selected from an aryl and a heterocyclic group.

In some embodiments, a compound is of the structure of Formula XVIII:

XVIII where n is 1, 2, 3 or 4;

$R^{55}$, $R^{56}$, and $R^{57}$ are as defined above for $R^{51}$, $R^{52}$, and $R^{53}$; and $R^{58}$ is selected from an aryl, an aryloxy and a heterocyclic group. In some embodiments, $R^{58}$ has the structure:

In some embodiments, a compound of the invention is of the structure of Formula XVIII where n is 2 or 3; $R^{55}$ and $R^{56}$ are methyl; $R^{57}$ is hydrogen; and $R^{58}$ is selected from an aryl, an aryloxy and a heterocyclic group.

In some embodiments, a compound of the invention is of the structure of one of Formulas XIX and XX:

XIX

XX where L is a linker of about 1 to 8 atoms in length;
n is 1, 2, 3 or 4;
$R^{61}$, $R^{62}$, and $R^{63}$ are as defined above for $R^{51}$, $R^{52}$, and $R^{53}$; and
$R^{64}$ and $R^{68}$ are independently one or more groups, each $R^{64}$ and $R^{68}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{64}$ or $R^{68}$ groups may be cyclically linked.

In some embodiments, a compound of the invention is of the structure of one of Formulas XIX and XX where n is 2 or 3; $R^{61}$, $R^{62}$, $R^{65}$ and $R^{66}$ are methyl; $R^{63}$ is $R^{67}$ are hydrogen; and $R^{64}$ and $R^{67}$ are independently selected from an aryl, an aryloxy and a heterocyclic group.

In some embodiments, in the structure of one of Formulas XIX and XX, at least one $R^{64}$ or $R^{68}$ group is selected from a carboxy, a formyl and a hydroxy, and is attached at the 2-position of the phenyl ring. In some embodiments, in the structure of one of Formulas XIX and XX, at least one $R^{64}$ or $R^{68}$ group is selected from a carboxy, a formyl and a hydroxy, and is attached at the 3-position of the phenyl ring. In some embodiments, in the structure of one of Formulas XIX and XX, at least one $R^{64}$ or $R^{68}$ group is selected from a carboxy, a formyl and a hydroxy and is attached at the 4-position of the phenyl ring.

In some embodiments, a compound of the invention is of the structure of Formula XXI:

XXI where $Z^5$ is a 5-membered heterocycle, a keto, a ketomethylene, a hydroxymethylene, a sulfonylamino or a amidomethylene; and $R^{71}$ and $R^{72}$ are independently one or more groups, each $R^{71}$ and $R^{72}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{71}$ or $R^{72}$ groups may be cyclically linked.

In some embodiments, in the structure of Formula XXI at least one $R^{71}$ or $R^{72}$ group is selected from a carboxy, a formyl and a hydroxy, and is attached at the 2-position of the phenyl ring. In some embodiments, in the structure of Formula XXI at least one $R^{71}$ or $R^{72}$ group is selected from a carboxy, a formyl and a hydroxy, and is attached at the 3-position of the phenyl ring. In some embodiments, in the structure of Formula XXI at least one $R^{71}$ or $R^{72}$ group is selected from a carboxy, a formyl and a hydroxy and is attached at the 4-position of the phenyl ring.

In some embodiments, a compound of the invention is of the structure of Formula XXII:

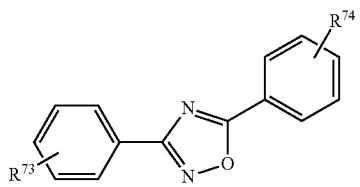

XXII where $R^{73}$ and $R^{74}$ are independently one or more groups, each $R^{73}$ and $R^{74}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{73}$ or $R^{74}$ groups may be cyclically linked.

In some embodiments, in the structure of Formula XXII at least one $R^{73}$ or $R^{74}$ group is selected from a carboxy, a formyl and a hydroxy, and is attached at the 2-position of the phenyl ring. In some embodiments, in the structure of Formula XXII at least one $R^{73}$ or $R^{74}$ group is selected from a carboxy, a formyl and a hydroxy, and is attached at the 3-position of the phenyl ring. In some embodiments, in the structure of Formula XXII at least one $R^{73}$ or $R^{74}$ group is selected from a carboxy, a formyl and a hydroxy and is attached at the 4-position of the phenyl ring.

In some embodiments, a compound of the invention is of the structure of Formula XXIII:

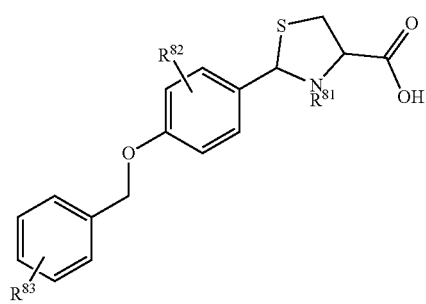

XXIII where $R^{81}$ is selected from an alkyl, an aryl, an alkoxy, an aryloxy, an acetyl, a carboxy, a formyl, an amido, a hydroxyl, a heterocyclic group, a halo, a nitro and a cyano; and $R^{82}$ and $R^{83}$ d independently one or more groups, each $R^{82}$ and $R^{83}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{82}$ and $R^{83}$ groups may be cyclically linked.

In some embodiments, a compound of the invention is of the structure of Formula XXIV:

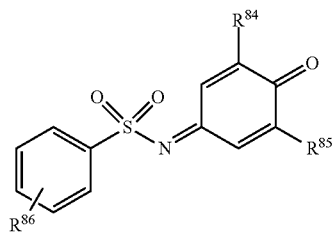

XXIV where $R^{84}$ and $R^{85}$ are independently selected from an alkyl, an aryl, an alkoxy, an aryloxy, an acetyl, a carboxy, a formyl, an amido, a hydroxyl, a heterocyclic group, a halo, a nitro and a cyano; and $R^{86}$ is one or more groups, each $R^{86}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{86}$ groups may be cyclically linked.

In some embodiments, a compound of the invention is of the structure of Formula XXV:

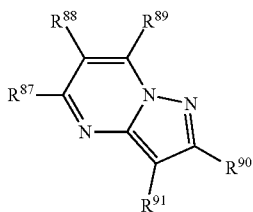

XXV where $R^{87}$, $R^{88}$, $R^{89}$, $R^{90}$ and $R^{91}$ are independently selected from an alkyl, an aryl, an alkoxy, an aryloxy, an acetyl, a carboxy, a formyl, an amido, a hydroxyl, a heterocyclic group, a halo, a nitro and a cyano.

In some embodiments, a compound of the invention is of the structure of Formula XXVI:

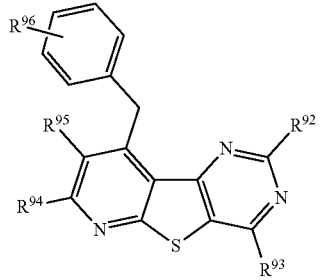

XXVI where $R^{92}$, $R^{93}$, $R^{94}$ and $R^{95}$ are independently selected from an alkyl, an aryl, an alkoxy, an aryloxy, an acetyl, a carboxy, a formyl, an amido, a hydroxyl, a heterocyclic group, a halo, a nitro and a cyano; and $R^{96}$ is one or more groups, each $R^{96}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{96}$ groups may be cyclically linked.

In some embodiments, a compound of the invention is of the structure of Formula XXVII:

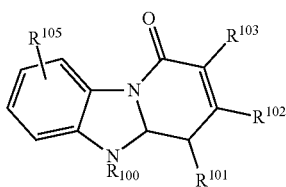

where $R^{100}$ is selected from an alkyl, an aryl, an acetyl, a sulfonyl and a heterocyclic group;

$R^{101}$, $R^{102}$ and $R^{103}$ are independently selected from an alkyl, an aryl, an alkoxy, an aryloxy, an acetyl, a carboxy, a formyl, an amido, a hydroxyl, a heterocyclic group, a halo, a nitro and a cyano; and $R^{105}$ is one or more groups, each $R^{105}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{105}$ groups may be cyclically linked.

In some embodiments, a compound of the invention is of the structure of Formula XXVIII:

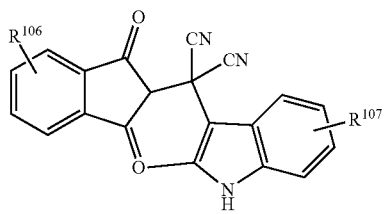

where $R^{106}$ and $R^{107}$ are independently one or more groups, each $R^{106}$ and $R^{107}$ independently selected from an alkyl, an aryl, an alkoxy, an aryloxy, an acetyl, a carboxy, a formyl, an amido, a hydroxyl, a heterocyclic group, a halo, a nitro and a cyano, where optionally two or more $R^{106}$ or $R^{107}$ groups may be cyclically linked.

In some embodiments a compound of the invention is of the structure of one of compounds 6-32 of Table 3. In some embodiments a compound of the invention is Ro 41-0960 or 3,5-dinitrocatechol (see Table 1).

TABLE 1

| Compound Structures | |
|---|---|
| 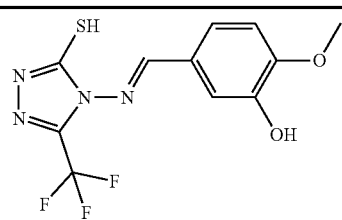 | 6 |
| 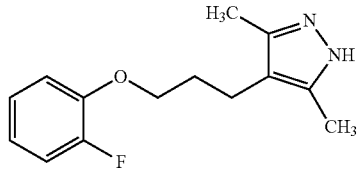 [SMILES: Cc1n[nH]c(C)c1CCCOc1ccccc1F] | 7 |

TABLE 1-continued

| Compound Structures | |
|---|---|
| 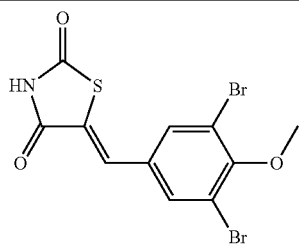 | 8 |
| 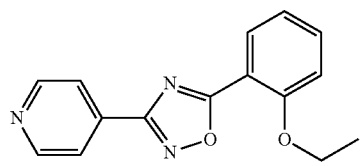 [SMILES: CCOc1ccccc1-c1nc(-c2ccncc2)no1] | 9 |
| 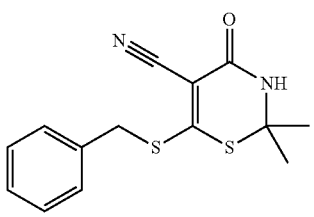 [SMILES: CC1(C)NC(=O)C(C#N)=C(SCc2ccccc2)S1] | 10 |
| 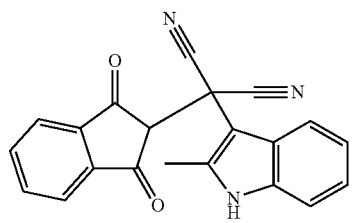 [SMILES: Cc1[nH]c2ccccc2c1C(C#N)(C#N)C1C(=O)c2ccccc2C1=O] | 11 |
| 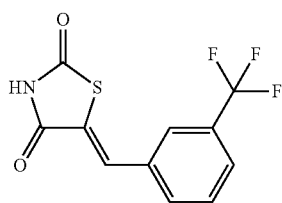 [SMILES: O=C1NC(=O)/C(=C/c2cccc(C(F)(F)F)c2)S1] | 12 |
| 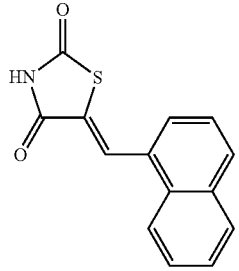 [SMILES: O=C1NC(=O)/C(=C/c2cccc3ccccc23)S1] | 13 |
| 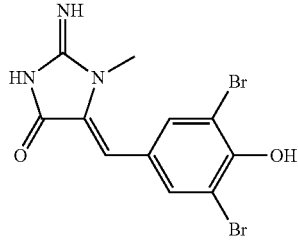 [SMILES: CN1C(=N)NC(=O)/C1=C/c1cc(Br)c(O)c(Br)c1] | 14 |

TABLE 1-continued
Compound Structures
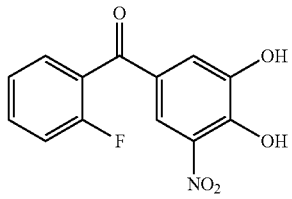
Ro 41-0960
14
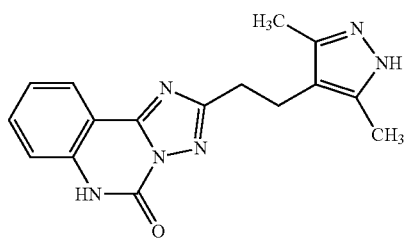 [SMILES: Cc1n[nH]c(C)c1CCc1nc2c3ccccc3[nH]c(=O)n2n1]
15
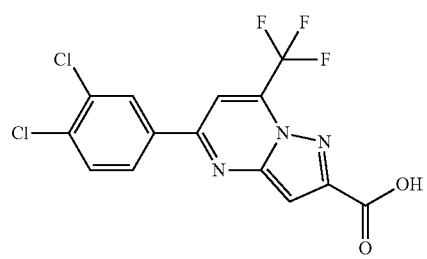 [SMILES: O=C(O)c1cc2nc(-c3ccc(Cl)c(Cl)c3)cc(C(F)(F)F)n2n1]
16
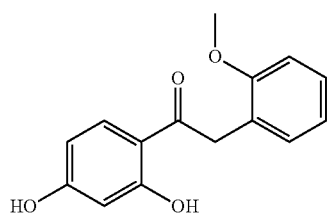 [SMILES: COc1ccccc1CC(=O)c1ccc(O)cc1O]
17
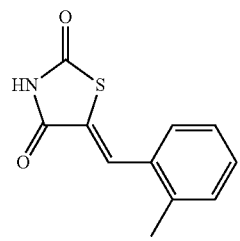
18
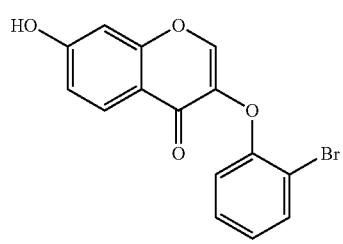 [SMILES: O=c1c(Oc2ccccc2Br)coc2cc(O)ccc12]
19
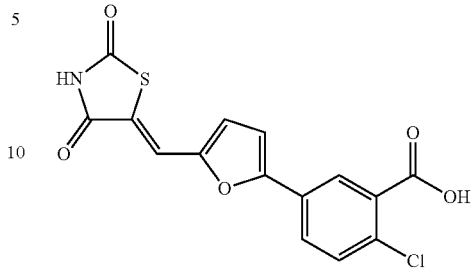
20
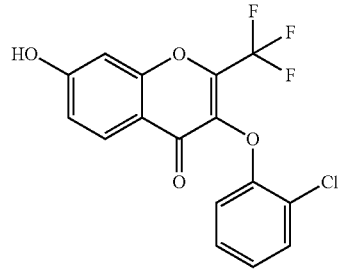 [SMILES: O=c1c(Oc2ccccc2Cl)c(C(F)(F)F)oc2cc(O)ccc12]
21
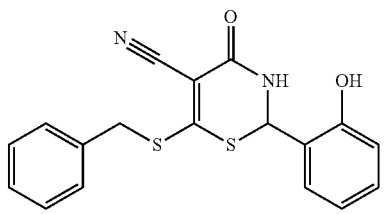 [SMILES: N#CC1=C(SCc2ccccc2)SC(c2ccccc2O)NC1=O]
22
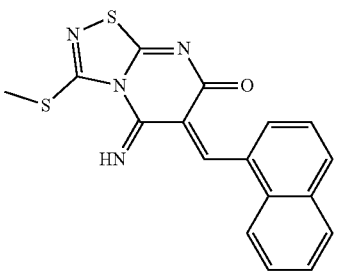 [SMILES: CSC1=NSC2=NC(=O)/C(=C\c3cccc4ccccc34)C(=N)N12]
23
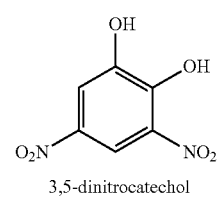
3,5-dinitrocatechol
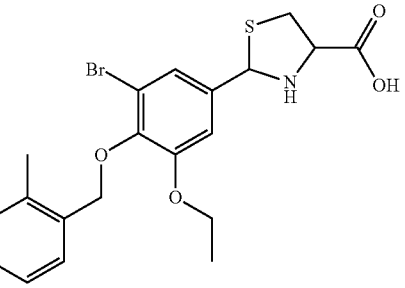
24

TABLE 1-continued

Compound Structures

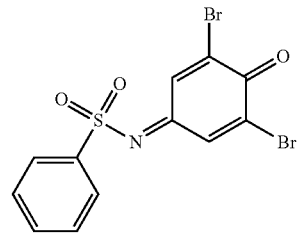 [SMILES: O=C1C(Br)=CC(=NS(=O)(=O)c2ccccc2)C=C1Br]
25

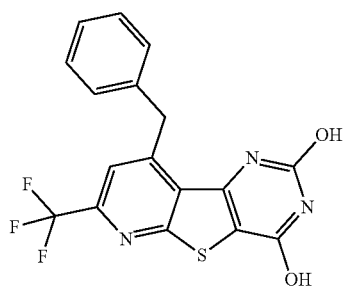 [SMILES: Oc1nc(O)c2sc3nc(C(F)(F)F)cc(Cc4ccccc4)c3c2n1]
26

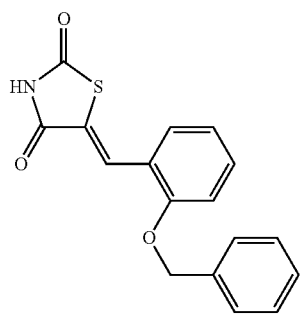 [SMILES: O=C1NC(=O)/C(=C/c2ccccc2OCc2ccccc2)S1]
27

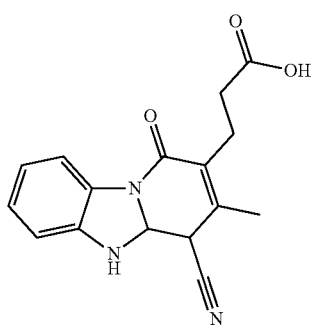 [SMILES: CC1=C(CCC(=O)O)C(=O)N2c3ccccc3NC2C1C#N]
28

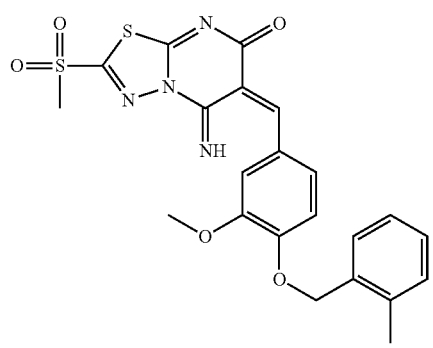 [SMILES: COc1cc(/C=C2\C(=N)N3N=C(S(C)(=O)=O)SC3=NC2=O)ccc1OCc1ccccc1C]
29

TABLE 1-continued

Compound Structures

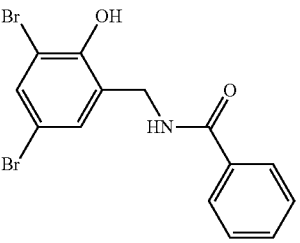 [SMILES: O=C(NCc1cc(Br)cc(Br)c1O)c1ccccc1]
30

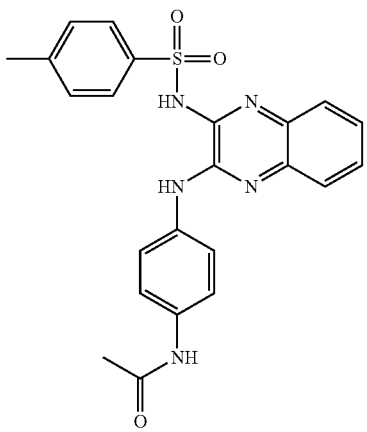 [SMILES: CC(=O)Nc1ccc(Nc2nc3ccccc3nc2NS(=O)(=O)c2ccc(C)cc2)cc1]
31

32

Bifunctional Compounds for Disrupting PPIs

Also provided are heterobifunctional compounds that include a recruitment moiety connected to a targeting moiety via a linker. The recruitment moiety is a ligand of an abundant serum protein (e.g., a TTR binding compound of the disclosure, as described above). The targeting moiety is a ligand for a protein target of interest. In some embodiments, the protein target is involved in a protein protein interaction (PPI) where disruption of the PPI is desirable. For example, the PPI may be important in the regulation of a biological process that leads to a particular disease condition, where disrupting the PPI of interest may provide a method of inhibiting or treating the disease condition.

In some embodiments, the heterobifunctional compound is of the formula R-L-T, where the recruitment moiety R is a TTR-binding compound described by a structure of Table 1; L is a linker; and T is a targeting moiety. In some cases, the subject heterobifunctional compound includes one or more, such as two or more, recruitment moieties.

The recruitment moiety is connected to the targeting moiety via a linker, at any convenient point of attachment, which may be readily selected by one of ordinary skill in the art such that the binding property of the ligand to its cognate protein is not significantly reduced. Exemplary attachment points and strategies of attachment include those described by Gestwicki et al. (Gestwicki, G. R. Crabtree, and I. A. Graef, Harnessing chaperones to generate small-molecule inhibitors of amyloid beta aggregation. Science, 2004. 306 (5697): p. 865-9) used to link Congo Red to a synthetic ligand for FKBP, which strategy and methods of chemical modification may be readily modified for use in the subject heterobifunctional compounds. In the TTR binding compounds described above, the position at which a linker may be connected using any convenient chemical modification chemistries is determined using any convenient selection method, such as but not limited to, modeling a X-ray crystal structure of TTR (e.g., a co-crystal structure of TTR with a ligand) to determine the mode of binding of the recruitment moiety to TTR and to select one or more appropriate positions which are not involved in contacts with the protein (e.g., solvent exposed positions), and which may be readily chemically modified. Further methods include determining whether a modification of interest has an adverse effect of the binding of the recruitment moiety to TTR using an in vitro binding assay. Exemplary modifications of four compounds of Table 1 (compounds Ro41-0960, 7, 14 and 9) which may be used to connect these compounds to linkers in the subject heterobifunctional compounds are shown below:

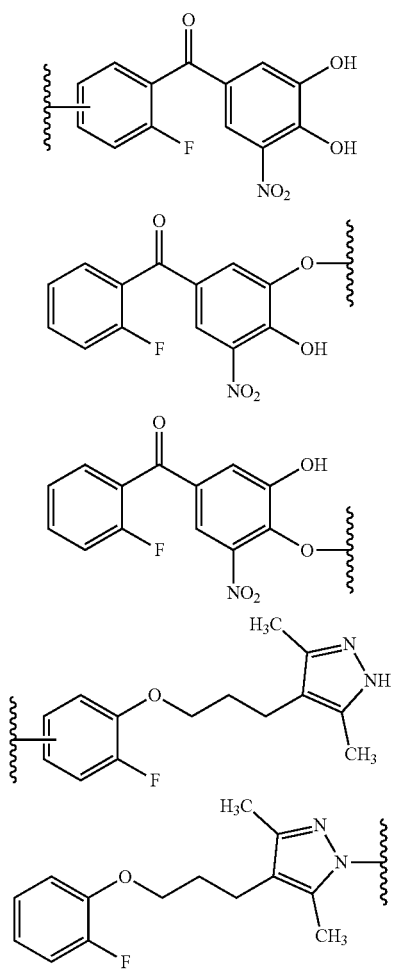

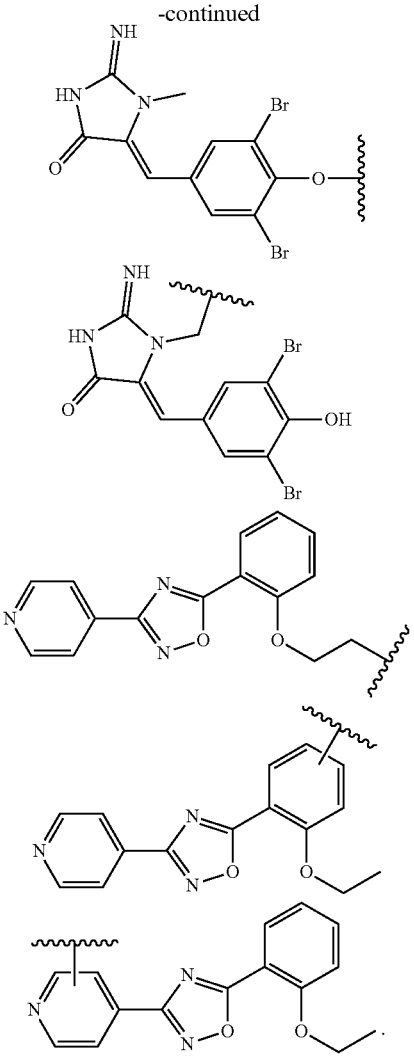

Figure 10:
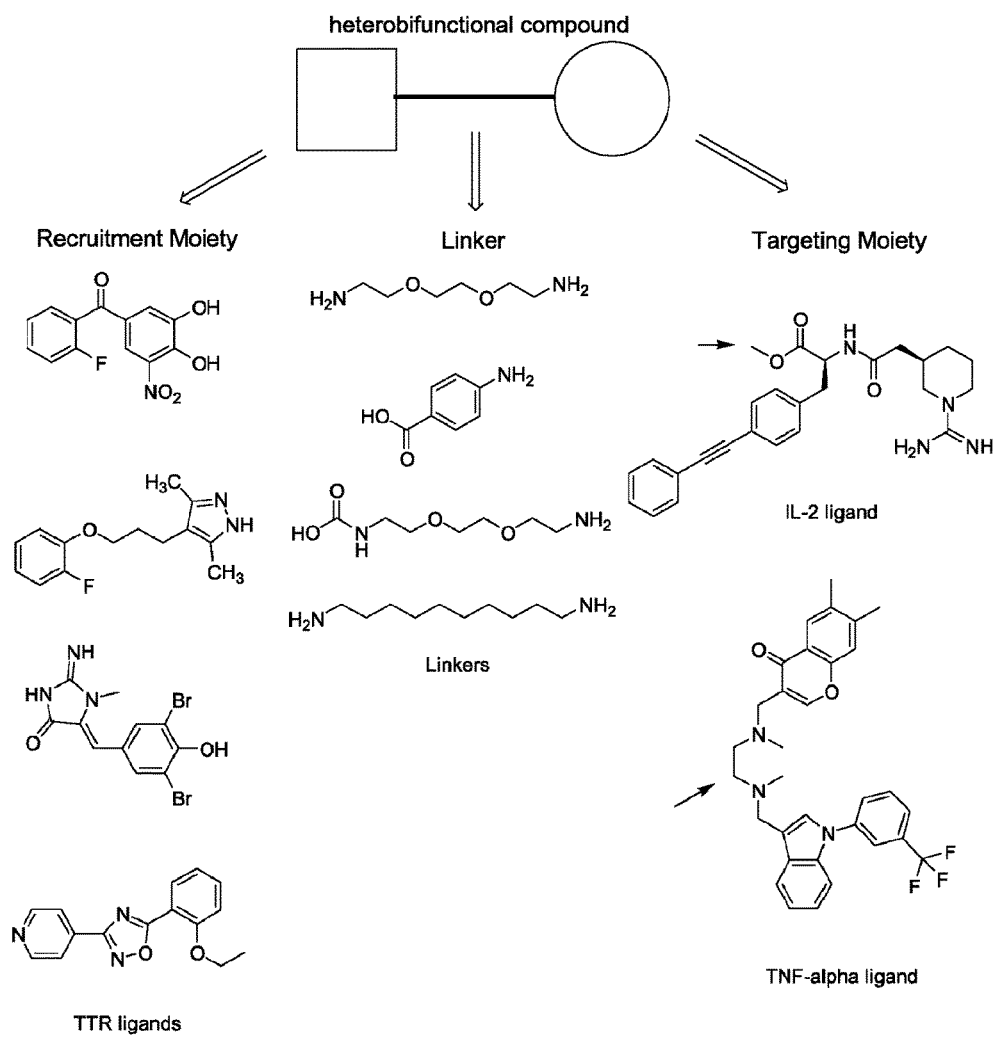
FIG. 10 depicts a heterobifunctional molecule (top) and the chemical structures of exemplary TTR ligands, linkers and targeting moieties, the IL2 binder Ro26-4550 (IC50 3-6 µM) and the TNFα ligand (IC50=22 µM) (bottom). The arrows show exemplary points of attachment of the linker to the targeting moiety.
Figure 11A:
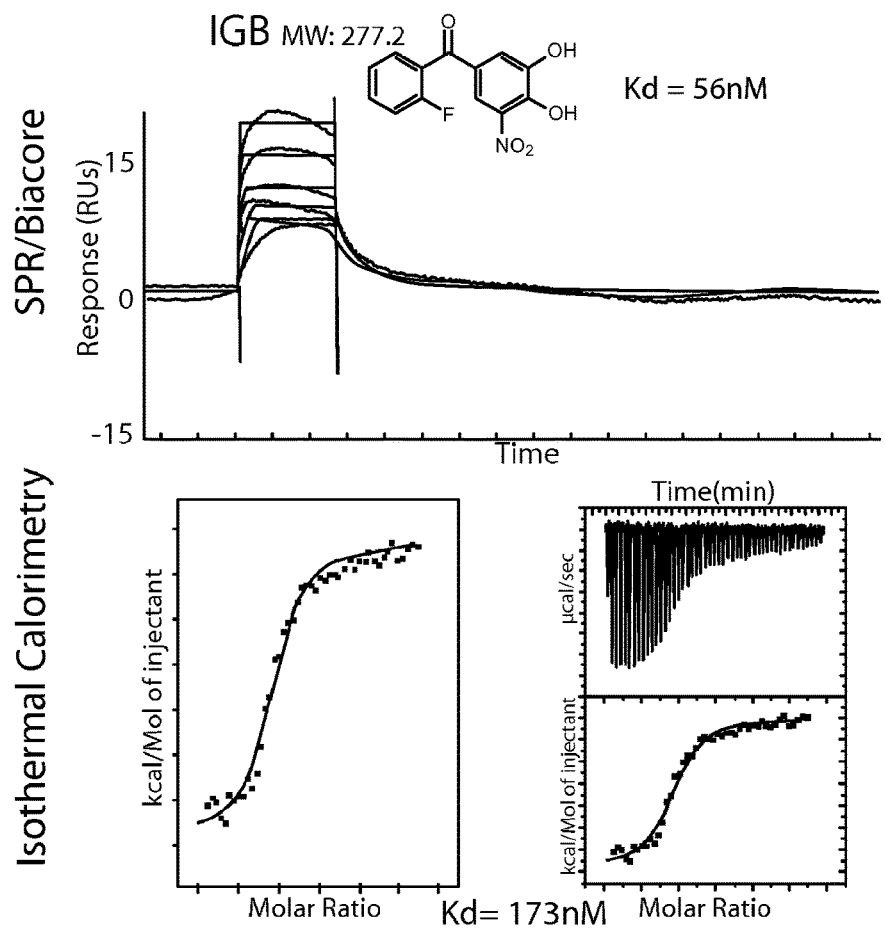
FIG. 11A-B shows SPR (Biacore) and ITC data and TTR binding affinities of two exemplary compounds identified using the FP-based HTS assay.
Figure 11B:
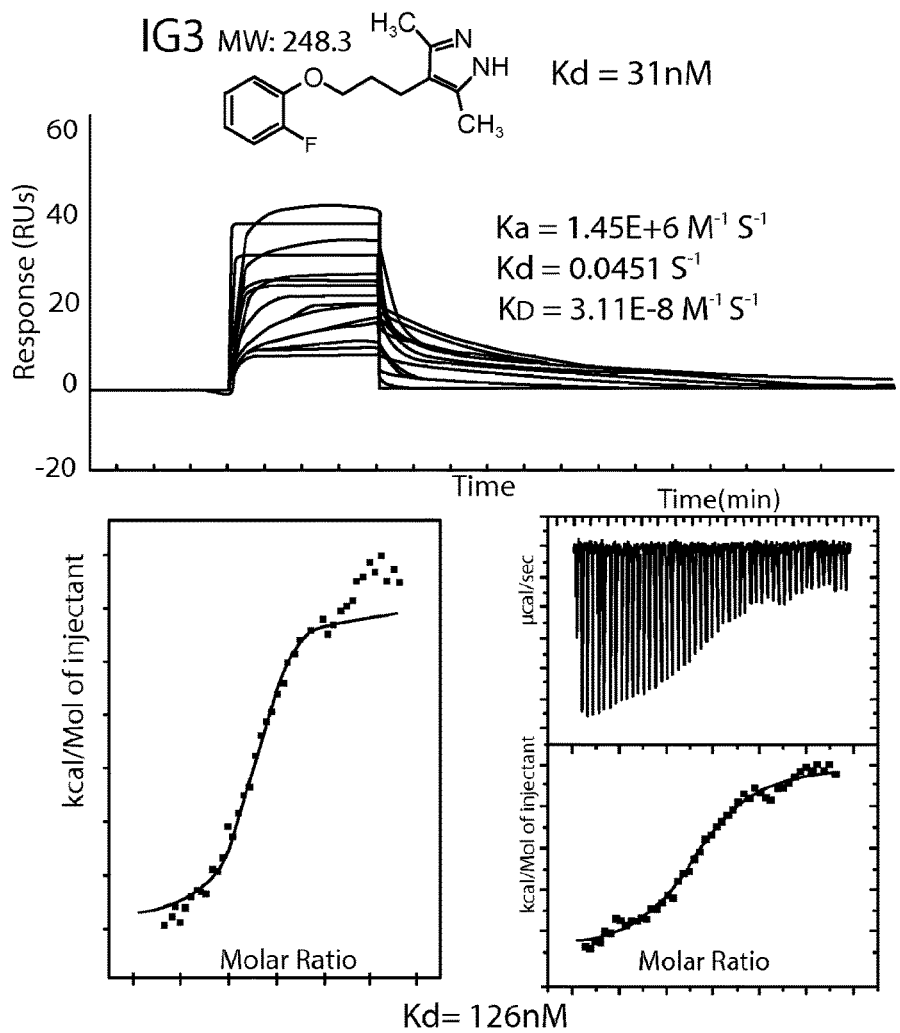
Figure 12:
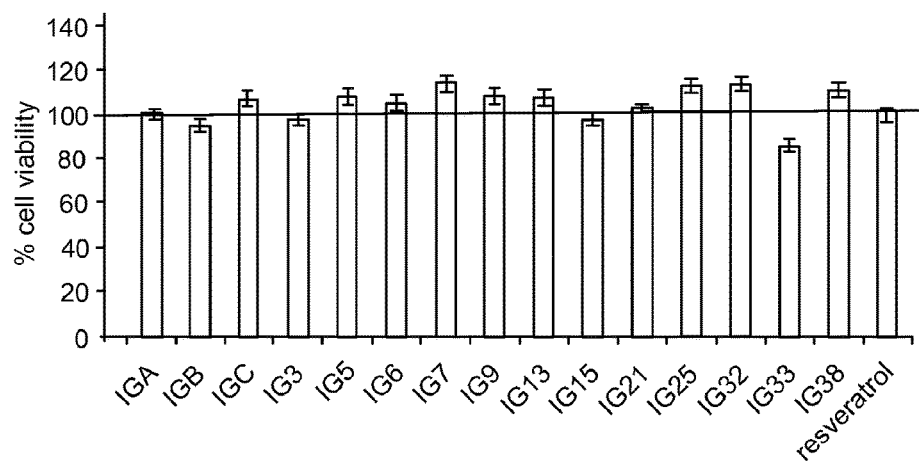
FIG. 12 illustrates the cell viability of primary cardiomyocytes assayed 48 hours after addition of TTR binders (10 µM).

Any convenient targeting moiety may be used. The targeting moiety may be a small molecule that targets a therapeutic protein target of interest. For example, the targeting moiety may be any convenient binder to a protein of a target ligand/receptor pair, such as but not limited to, IL2/IL2Rα, TNFα/TNFR1, VEGF-VEGFR, CCL12-CXCR4, CD4-gp120, c-Met-HGF, and LFA-1-CD54. In some embodiments, the targeting moiety is an IL-2 ligand such as the IL-2 antagonist Ro26-4550 (FIG. 10). In some embodiments, the targeting moiety is a small molecule TNF-α inhibitor, such as the compound disclosed by He et al. (Science, 2005, 310, 1022-1025) (FIG. 10). Suitable positions of the targeting moieties described above, to which a linker may be attached are selected using any convenient method, such as but not limited to, modeling methods using a X-ray crystal structure of the target protein (e.g., a co-crystal structure of target protein bound with the ligand) to model the mode of binding of the targeting moiety and to select appropriate positions that are not involved in contacts with the target protein (e.g., solvent exposed positions), and which may be readily chemically modified. For example, co-crystal structures of the IL-2 and TNF-alpha ligands shown in FIG. 10 are available for use in selecting convenient sites in these targeting moieties for chemical modification and attachment of linkers in preparation of subject heterobifunctional compounds. Further methods include determining whether a modification of interest has an adverse effect of the binding of the targeting moiety to the target protein using an in vitro binding assay.

Exemplary modifications of IL-2 and TNF-α targeting moieties of interest that may be used to attach these targeting moieties to linkers in heterobifunctional compounds are shown below:

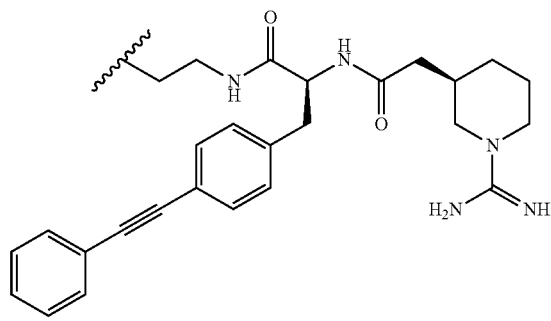

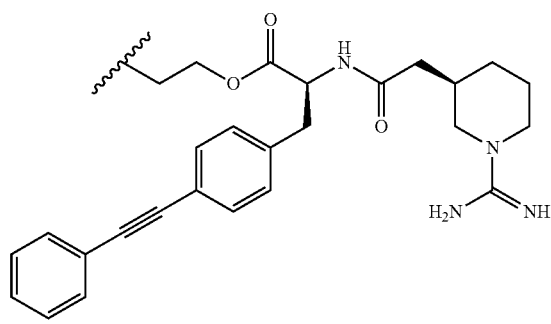

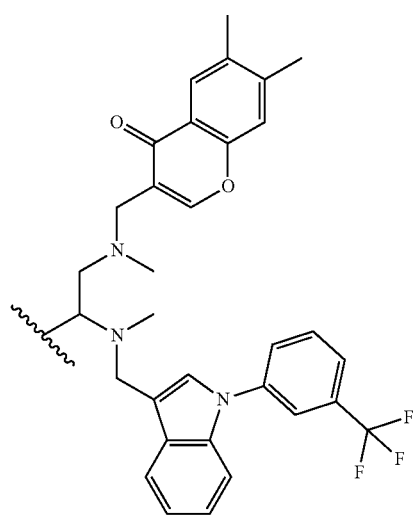

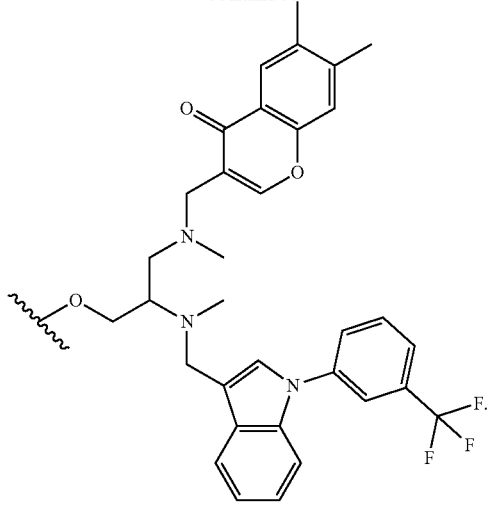

In some embodiments the protein target of interest is not FKBP, e.g., the targeting moiety is not a ligand for FKBP.

As used herein, the term "linker", "linkage" and "linking group" refers to a linking moiety that connects two groups and has a backbone of 20 atoms or less in length. A linker or linkage may be a covalent bond that connects two groups or a chain of between 1 and 20 atoms in length, for example of about 1, 2, 3, 4, 5, 6, 8, 10, 12, 14, 16, 18 or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, usually not more than one, two, or three unsaturated bonds will be present in a linker backbone. The linker may include one or more substituent groups, for example with an alkyl, aryl or alkenyl group. A linker may include, without limitations, oligo(ethylene glycol); ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

The linking moiety may be conjugated to the recruitment and targeting moieties using any convenient functional groups (carboxylic acids, amines, alcohols, carbamates, esters, ethers, thioethers, maleimides, and the like), and linking chemistries. For example, any convenient conjugation chemistry described by G. T. Hermanson ("Bioconjugate Techniques", Academic Press, Second Edition, 2008) may be readily adapted for use in preparing the subject heterobifunctional compounds.

Exemplary linkers that may be used in connecting the recruitment moiety to the targeting moiety using any convenient chemical modification methods are shown below:

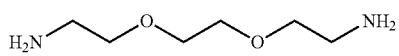

-continued

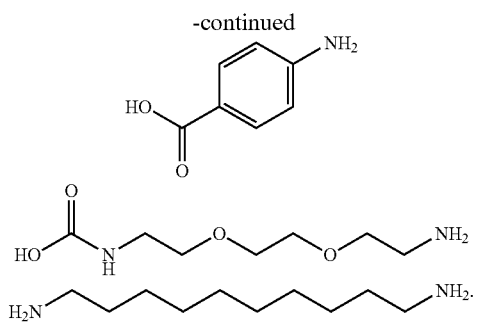

Dosage Forms of Compounds of the Present Disclosure

In pharmaceutical dosage forms, the compounds disclosed herein may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated include but are not necessarily limited to, enteral, parenteral, or inhalational routes, such as intrapulmonary or intranasal delivery.

Conventional and pharmaceutically acceptable routes of administration include intranasal, intrapulmonary, intramuscular, intratracheal, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. If oral administration is desired, the subject compounds may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Parenteral routes of administration other than inhalation administration include, but are not necessarily limited to, topical, transdermal, subcutaneous, intramuscular, intraorbital, intracapsular, intraspinal, intrasternal, and intravenous routes. Parenteral administration can be carried to effect systemic or local delivery of the agent. Where systemic delivery is desired, administration typically involves invasive or systemically absorbed topical or mucosal administration of pharmaceutical preparations. Where local delivery is desired, administration typically involves administering the composition to a desired target tissue, such a liver, heart, spine, etc. For local delivery, the administration may be by injection or by placement of the composition in the desired tissue or organ by surgery, for example.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject compounds of the invention can be formulated into preparations for injection by dissolving, suspending or emulsifying them in an aqueous or nonaqucous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Present Disclosure

Depending on the subject and condition being treated and on the administration route, the subject compounds may be administered in dosages of, for example, 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from one to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 μg to about 1,000 μg or about 10,000 μg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other protein stabilizing agents, such as resveratrol, heat shock proteins, protein chaperones, and mimics thereof.

The compounds described above may also be administered in combination with other therapies for diseases caused by TTR amyloid fibrils. Therapies for diseases caused by TTR amyloid fibrils include heart transplant for TTR cardiomyopathy, liver transplant, Tafamidis for treatment of FAP, and the like. The compound described above may be administered before, after, or during another therapy for diseases caused by TTR amyloid fibrils.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods

Also provided herein are methods for screening for compounds that increase the stability TTR, thereby preventing it from misfolding and forming amyloid fibrils.

Provided herein are methods for using the disclosed compounds to increase the stability of TTR thereby preventing it from misfolding and forming TTR amyloid fibrils.

Methods for Screening for Protein Stabilizers

A method for screening for TTR stabilizers is provided. The method generally includes screening a candidate compound for stabilizing TTR by competitively binding to the same site as bound by a TTR ligand known to bind and stabilize TTR. The method includes: a) contacting a TTR-fluorescence polarization probe (FP probe) complex with a candidate compound, wherein FP-probe in the TTR-FP probe complex comprises a ligand for TTR and a fluorescent moiety attached to the ligand by a linker, wherein the FP-probe stabilizes TTR, and wherein the TTR-FP probe complex generates a FP signal; and h) determining the FP signal, wherein a decrease in the FP signal indicates the candidate compound stabilizes TTR.

The method may further comprise determining that the candidate compound is bound to TTR. The method may further comprise determining the formation of amyloid fibrils by TTR in the presence of the candidate compound.

The transthyretin used in the screening methods can be wild type transthyretin or a mutant transthyretin, such as a naturally occurring mutant transthyretin causally associated with the incidence of a transthyretin amyloid disease such as familial amyloid polyneuropathy or familial amyloid cardiomyopathy. Exemplary naturally occurring mutant transthyretins include, but are not limited to, V1221, V30M, L55P (the mutant nomenclature describes the substitution at a recited amino acid position, relative to the wild type; see, e.g., Saraiva et al. (2001) Hum. Mut. 17:493 503).

As noted above, the FP-probe comprises of a ligand and a fluorescence moiety. The ligand may bind and stabilize TTR and prevent it from forming amyloid fibrils. Thus, the FP-probe can also bind and stabilize TTR. In certain embodiments, ligands that bind to and increase the stability of TTR may be already known or may be identified prior to conducting the screen. Methods for identifying ligands and testing the ligand for increasing stability of TTR can be designed by the skilled artisan.

In certain embodiments, the ligand may be a ligand known to bind to TTR and increase its stability thereby decreasing its tendency to form amyloid fibrils. A number small molecules that inhibit TTR amyloid formation by binding to the thyroxine (T4) sites in TTR and kinetically stabilizing its quaternary structure are known. Examples of such stabilizing ligands include Tafamidis, diflunisal, diclofenac analogue, and Resveratrol.

The ligand may be attached to a fluorescent moiety by a linker. Such linkers are well known in the art. Generally, the linkers do not completely disrupt the binding of the ligand to the protein. In general, the attachment of a linker to the ligand decreases its binding to the protein by less than 50%, for example by less than 40%, or less than 30%, or less than 20%, or less than 10%, or less than 5%, or less than 1% or less.

Examples of linker include Polyethylene glycol (PEG), PEG amide, PEG diamide,N,N-(1,2-aminoethyl); N,N-(2-{2-[2-(2-aminoethoxy)-ethoxy]-ethoxy}-aminoethyl); N,N-(2-[2-(2-aminoethoxy)-ethoxy]-aminoethyl); N,N-[2-(2-{2-[2-(2-aminoethoxy)-ethoxy]-ethylcarbamoyl}-ethyldisulfanyl)-aminoethyl]; N,N-(amidoacetamido); N-[(5-{2-[2-(2-aminoethoxy)-ethoxy]-ethylcarbamoyl}-pentyl)-carboxamide]; N-({5-[2-(2-aminoethyldisulfanyl)-ethylcarbamoyl]-pentyl})-carboxamide; N,N-[(5-aminopentyl)-thioureidyl]; N-({2-[2-(2-aminoethoxy)-ethoxy]-ethyl}-carboxamide); or an alkyl linker, optionally including one or heteroatoms in the linker backbone, e.g., —O(CH$_2$)$_n$—, where n is 1, 2, 3, 4, 5 or 6. The linker may be chosen based on the functional groups present on the ligand and the fluorescent moiety. Linkers that may be used to attach a ligand to a fluorescent moiety can be determined by one of skill in the art.

The fluorescent moiety may be any fluorophore or fluorescent group that when excited by light of suitable wavelength can emit fluorescence with high quantum yield. See, for example, J. R. Lakowicz in "Principles of Fluorescence Spectroscopy," Plenum Press, 1983. Numerous known fluorophores of a wide variety of structures and characteristics are suitable for use in the practice of methods disclosed here. Typical fluorescing compounds, which are suitable for use in the present invention, include, for example, rhodamine, substituted rhodamine, fluorescein, fluorescein isothiocyanate, naphthofluorescein, dichlorotriazinylamine fluorescein, dansyl chloride, phycoerythrin, and umbelliferone. Other suitable fluorescent groups for use in the present invention include, but are not limited to, those described in U.S. Pat. Nos. 4,255,329, 4,668,640 and 5,315,015.

Candidate compounds that may be used in the method for screening for stabilizers of TTR, include numerous chemical classes, primarily organic molecules, although including in some instances inorganic molecules, organometallic molecules. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups.

Candidate compounds may be obtained from a wide variety of sources including libraries of synthetic or natural compounds. For example, numerous means are available for random and directed synthesis of a wide variety of small molecule compounds. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A plurality of assays may be run in parallel with a plurality of different candidate compounds. More than one concentration of one or more of the candidate compounds may be tested to obtain a differential response to the various concentrations. As known in the art, determining the effective concentration of a candidate compound typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in FP signal.

In general, the method comprises contacting a TTR-FP probe complex with a candidate compound. The method uses the polarization signal of the FP-probe. When the FP-probe is free in solution, the FP signal is low. As the FP-probe binds to TTR, the FP signal increases, the increase in the FP signal is proportional to the decrease in the rate of tumbling of a FP-probe upon binding to the protein. Thus, the TTR-FP-probe complex generates a FP signal. When a candidate compound binds to TTR and displaces the bound FP-probe from the protein-FP probe complex, the FP polarization signal decreases. A decrease in the FP polarization signal indicates that the compound can bind to TTR and displace the stabilizing FP-probe. Since the compound competitively binds to the protein in the presence of the stabilizing FP-probe, the compound may be more active in stabilizing TTR compared to the ligand in the FP-probe.

In general, a decrease in the FP polarization signal indicates that the candidate compound can bind to TTR and stabilize TTR. The decrease in FP signal that identifies the candidate compound as a stabilizer for the protein may be about 10%, or about 20%, or about 30%, or about 40%, or about 50%, or more.

As noted above, the method may further comprise determining the binding of the candidate compound to TTR. Any suitable method may be used. Examples of some methods include, Surface Plasmon Resonance (SPR), Isothermal Titration calorimetry (ITC), and the like.

As noted above, the method may further comprise determining the formation of aggregates and/or fibrils by TTR in the presence of the candidate compound. Such methods are well known in the art. Exemplary methods for determining formation of aggregates and/or fibrils by TTR are provided below.

In certain embodiments, a method for screening for a candidate compound that binds TTR protein is provided. The method includes: a) contacting a TTR-fluorescence polarization probe (FP probe) complex with a candidate compound, wherein FP-probe in the TTR-FP probe complex comprises a ligand for TTR and a fluorescent moiety attached to the ligand by a linker, wherein the FP-probe stabilizes TTR, and wherein the TTR-FP probe complex generates a FP signal; and b) determining the FP signal, wherein a decrease in the FP signal indicates the candidate compound binds TTR.

In general, the compounds disclosed herein as well as the TTR stabilizers identified by the screening methods disclosed above may be used to prevent or reduce the dissociation of a TTR tetramer.

Use of TTR Stabilizers to Decrease TTR Amyloid Formation

The TTR stabilizers disclosed herein and those identified by the screening methods disclosed above may be used to decrease TTR amyloid formation and to decrease cell dysfunction and/or death associated with TTR amyloid formation. The TTR stabilzers may be used to decrease TTR amyloid formation in vitro in a cell-free system, in vitro in cells, and in vivo.

Amyloid fibril formation may be determined using a turbidity assay in vitro in a cell-free system. The turbidity assay can use a wild-type TTR or a mutant of TTR with an increased tendency to form amyloid fibrils. When a wild-type TTR is used TTR amyloidogenesis may be initiated by acidification of TTR. When a mutant of TTR with an increased tendency to form amyloid fibrils, acidification of TTR may also be used.

TTR stabilizers disclosed herein and those identified by the screening methods disclosed above may be used to decrease TTR amyloid formation in a cell.

Also provided ides for methods for the stabilization of transthyretin in a tissue or in a biological fluid, and thereby inhibiting misfolding. Generally, the method comprises administering to the tissue or biological fluid a composition comprising a stabilizing amount of a compound described herein that binds to transthyretin and prevents dissociation of the transthyretin tetramer by kinetic stabilization of the native state of the transthyretin tetramer.

Thus, methods which stabilize transthyretin in a diseased tissue ameliorate misfolding and lessen symptoms of an associated disease and, depending upon the disease, can contribute to cure of the disease. The invention contemplates inhibition of transthyretin misfolding in a tissue and/or within a cell. The extent of misfolding, and therefore the extent of inhibition achieved by the present methods, can be evaluated by a variety of methods, such as are described in the Examples.

Accordingly, in another aspect the invention includes a method of treating a transthyretin amyloid disease, the method comprising administering to a subject diagnosed as having a transthyretin amyloid disease a therapeutically effective amount of a compound that stabilizes the native state of the transthyretin tetramer.

In one embodiment, the invention features a method of treating a transthyretin amyloid disease, the method comprising administering to a subject diagnosed as having a transthyretin amyloid disease a therapeutically effective amount of a compound disclosed above that stabilizes transthyretin tetramer.

The transthyretin amyloid disease can be, for example, familial amyloid polyneuropathy, familial amyloid cardiomyopathy, or senile systemic amyloidosis.

The subject treated in the present methods can be a human subject, although it is to be understood that the principles of the invention indicate that the invention is effective with respect to all mammals.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); Room Temperature, RT, rt, and the like.

Materials and Methods

Reagents and Instruments.

Prealbumin from human plasma (human TTR) was purchased from Sigma. EZ-Link Sulfo-NIIS-LC-Biotin was purchased from Pierce. Diclofenac (sodium salt) was purchased from TCI. All reactions were carried out under nitrogen atmosphere using dry solvents under anhydrous conditions, unless otherwise noted. The solvents used were ACS grade from Fisher. Reagents were purchased from Aldrich and Acros, and used without further purification. Reactions were monitored by thin-layer chromatography (TLC) carried out on 0.20 mm POLYGRAM® SIL silica gel plates (Art.-Nr. 805 023) with fluorescent indicator $UV_{254}$ using UV light as a visualizing agent. Normal phase flash column chromatography was carried out using Davisil® silica gel (100-200 mesh, Fisher). $^1$H NMR spectra were recorded on INOVA 400 MHz spectrometers and calibrated using residual undeuterated solvent as an internal reference. Coupling constants (J) were expressed in Hertz. The following abbreviations were used to explain the multiplicities: s=singlet, d=doublet, t=triplet, q=quartet, m=multiplet. High-resolution mass spectra (HRMS) were recorded on a Micromass LCT Electrospray mass spectrometer performed at the Mass Spectrometry & Proteomics Facility (Stanford University). HPLC analysis was performed on Waters Delta 600 HPLC system connected to a diode array detector. The samples were analyzed on Xbridge® C18 5 μm reverse phase column (4.6×150 mm) using a linear gradient between solvent A (acetonitrile with 0.05% formic acid) and solvent B (water with 0.05% formic acid) from 0% to 100% over 10 or 20 minutes at a flow rate of 0.5 ml/min and detected at 254 nm.

Chemical Synthesis

N-(2-(2-(2-aminoethoxy)ethoxy)ethyl)-2',6'-difluorobiphenyl-4-carboxamide (Compound 2)

2,2'-(ethane-1,2-diylbis(oxy))diethanamine (280 mg, 1.89 mmol) was added to a cooled (0° C.) solution of carboxylic acid 1 (22 mg, 0.09 mmol) in anhydrous methylene chloride (2 ml). After 10 min, PyBop (59 mg, 0.11 mmol) was added and the reaction was warmed to room temperature and stirred for additional 3 hours. Methylene chloride was added and the organic layer was washed with semi-saturated sodium bicarbonate solution and water. The organic layer was dried over sodium sulfate, filtered, and the solvent was removed under reduced pressure. Purification by flash column chromatography (silica gel, 5-10% methanol/methylene chloride) gave 2 (26 mg, 76% yield); $^1$H NMR (CD$_3$OD, 400 MHz) δ 7.93 (d, 2H, J=8.4 Hz), 7.56 (d, 2H, J=8.4 Hz), 7.47-7.41 (m, 1H), 7.10 (t, 2H, J=8.2 Hz), 3.72-3.61 (m, 8H), 3.18-3.04 (m, 4H); HRMS (ESI$^+$) m/z: calcd for $C_{19}H_{22}F_2N_2O_{3+H}^+$ 365.1677; found 365.1671 (M+H$^+$). A schematic of the preparation of compound 2 from compound 1 is shown below. a) PyBop, CH$_2$Cl$_2$, 0° C. to RT, 3 h.

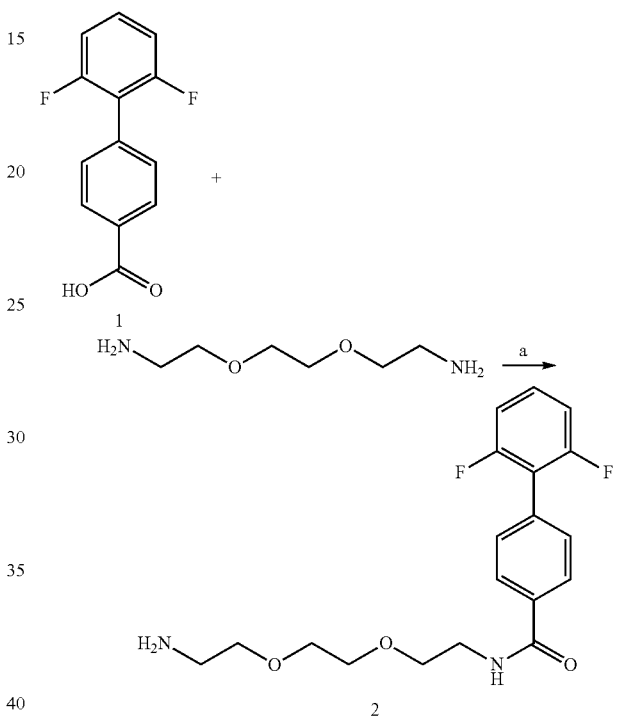

tert-butyl-2-(3,5-dichloro-4-(2,2-dimethyl-4-oxo-3,8,11-trioxa-5-azatridecan-13 yloxy)phenylamino)benzoate (35)

To a solution of 33 (177 mg, 0.5 mmol), linker 34 (137 mg, 0.55 mmol), and triphenylphosphine (197 mg, 0.75 mmol) in anhydrous THF (6.0 mL) was added a solution of 1,1'-(azodicarbonyl)dipiperidine (ADDP) (189 mg, 0.75 mmol) in THF (1.0 ml) dropwise. The reaction was stirred at room temperature for 4 days and then concentrated and purified by flash column chromatography (silica gel, 5-20% EtOAc/hexanes) to afforded compound 35 (148 mg, 51% yield); $^1$H NMR (CDCl$_3$, 400 MHz) δ 9.54 (s, 1H), 7.91 (dd, 1H, J=2.0 Hz, 9.5 Hz), 7.37-7.32 (m, 1H), 7.20 (dd, 1H, J=1.0 Hz, 8.6 Hz), 7.18 (s, 2H), 6.81-6.76 (m, 1H), 5.08-5.0 (m, 1H), 4.19 (t, 2H, J=4.8 Hz), 3.91-3.88 (m, 2H), 3.77-3.74 (m, 2H), 3.67-3.65 (m, 2H), 3.57 (t, 2H, J=4.8 Hz), 3.34-3.30 (m, 2H), 1.59 (s, 9H), 1.43 (s, 9H); Low resolution mass spectra for $C_{28}H_{38}Cl_2N_2O_7$ (ESI$^+$): m/z: 585.15(M+H$^+$), 607.17 (M+Na$^+$)

2-(4-(2-(2-(2-aminoethoxy)ethoxy)ethoxy)-3,5-dichlorophenylamino)benzoic acid (4)

Trifluoroacetic acid (0.5 ml) was added dropwise to a solution of 35 (5 mg, 0.008 mmol) in methylene chloride (2.0 ml) at 0° C. The reaction mixture was warmed to room temperature and stirred for additional 4 h. The solvents were removed under reduced pressure to give the trifluoroacetate salt of compound 4 (4 mg, 90% yield); $^1$H NMR (CD$_3$OD, 400 MHz) δ 8.0 (dd, 1H, J=2.0 Hz, 8.0 Hz), 7.44-7.39 (m, 1H), 7.26-7.22 (m, 3H), 6.88-6.82 (m, 1H), 5.02-4.94 (m, 1H), 4.19 (t, 2H, J=4.6 Hz), 3.91-3.88 (m, 2H), 3.79-3.76 (m, 2H), 3.74-3.71 (m, 4H), 3.12 (t, 2H, J=4.6 Hz); HRMS (ESI$^+$) m/z: calcd for $C_{19}H_{22}Cl_2N_2O_5$+H$^+$ 429.0984; found 429.0986 (M+H$^+$).

2-(3,5-dichloro-4-(2-(2-(2-(3-(3',6'-dihydroxy-3-oxo-3H-spiro[isobenzofuran-1,9'-xanthene]-5-yl)thioureido)ethoxy)ethoxy)ethoxy)phenylamino)benzoic acid (5)

N,N-Diisopropylethylamine (10 μL, 0.057 mmol) was added to a solution of the compound 4 (1.9 mg, 0.0035 mmol) and fluorescein isothiocyanate (FITC) (1.2 mg, 0.003 mmol) in DMF (1.0 ml) and the reaction mixture was stirred at room temperature overnight. The solvent was removed under reduced pressure and the residue was subjected to flash column chromatography (silica gel, 1-20% methanol/methylene chloride) to give the desired compound 5 (1.5 mg, 52% yield); 1H NMR (CD$_3$OD, 400 MHz) δ 8.14-8.10 (m, 1H), 7.88 (dd, 1H, J=2.0 Hz, 8.0 Hz), 7.80-7.62 (m, 2H), 7.34-7.30 (m, 1H), 7.24-7.18 (m, 1H), 7.18-7.12 (m, 3H), 6.86-6.78 (m, 1H), 6.72-6.64 (m, 3H), 6.54-6.50 (m, 2H), 4.21-4.04 (m, 4H), 3.92-3.66 (m, 8H); HRMS (ESI$^+$) m/z: calcd for $C_{40}H_{33}Cl_2N_3O_{10}S$+H$^+$ 818.1342; found 818.1328 (M+H$^+$).

A schematic for the synthesis of compounds 35, 4, and 5 is shown below.

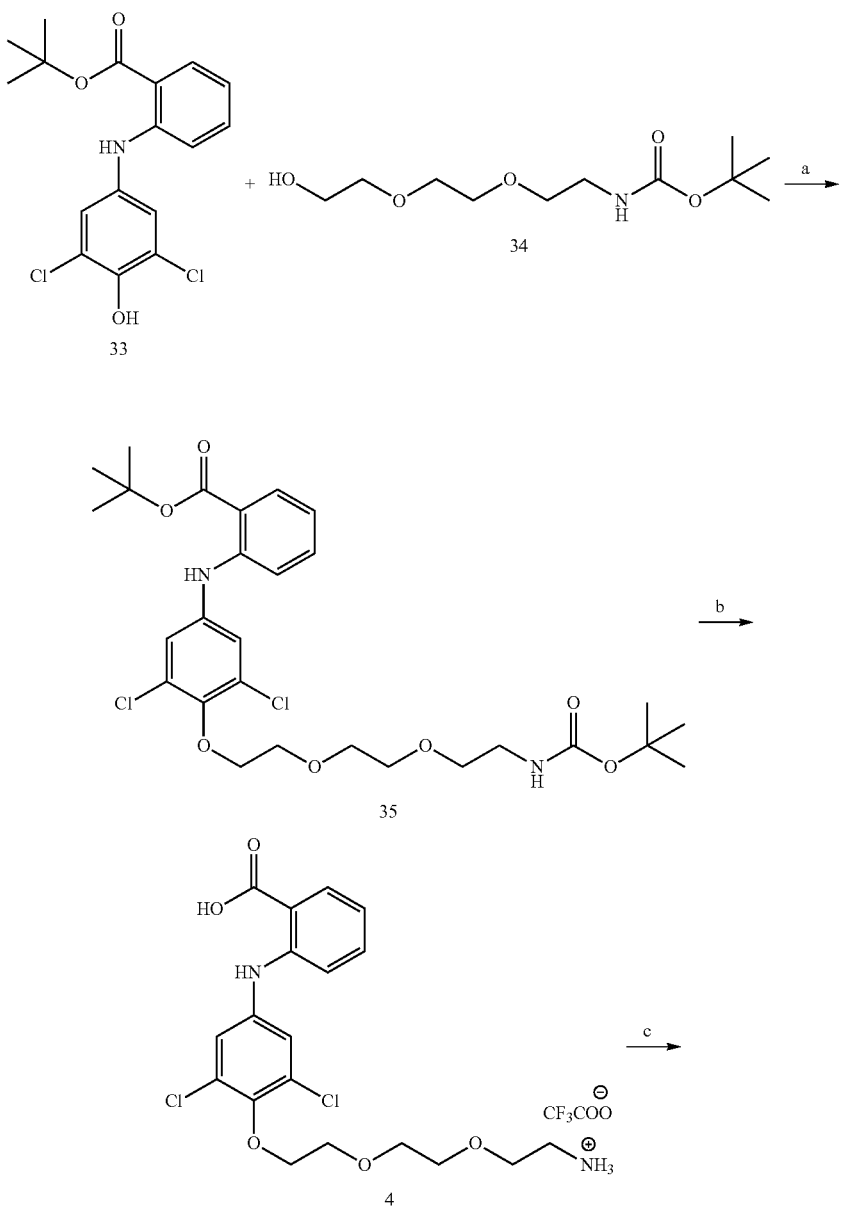

-continued

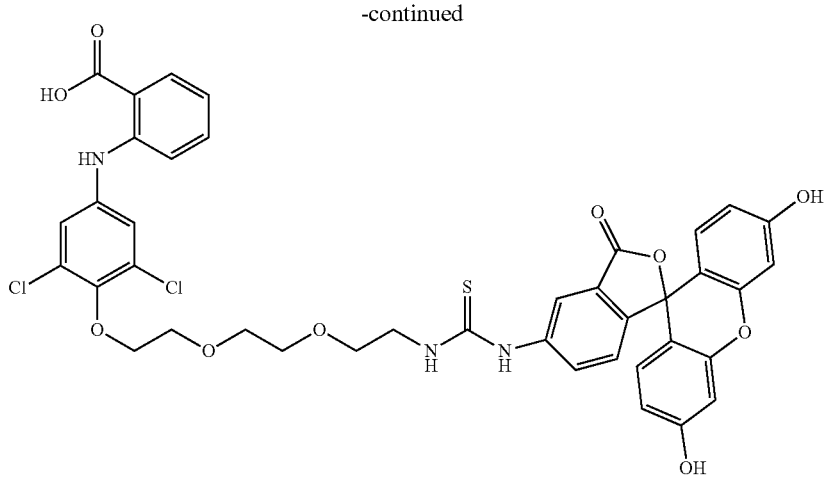

5 a) PPh₃, ADDP, THF, RT, 2 days; b) Trifluoroacetic acid, CH₂Cl₂, 0° C. to RT, 4 h; c) FITC, DIPEA, DMF, RT, 16 h.

Isothermal Titration Calorimetry (ITC).

Calorimetric titrations were carried out on a VP-ITC calorimeter (MicroCal, Northhampton, Mass.). A solution of small molecule (25 µM in PBS pH 7.4, 100 mM KCl, 1 mM EDTA, 8% DMSO) was prepared and titrated into an ITC cell containing 2 µM of TER in an identical buffer. Prior to each titration, all samples were degassed for 10 minutes. The initial injection of 3.0 µL was followed by 30 injections of 8.0 µL each (25° C.) to the point that TTR was fully saturated with ligand. Integration of the thermogram after subtraction of blanks yielded a binding isotherm that was analyzed with MicroCal Origin 5.0 software.

Fluorescence Polarization Binding Assays

Saturation Binding Experiment.

The binding of probe 5 for TTR was evaluated as follows. In a black 96-well plate (Costar), solutions (150 µL final volumes) containing 5 (100 nM) were incubated with various concentrations of human TTR (5 nM to 10 µM) in assay buffer (PBS pH 7.4, 0.01% Triton-X100, 1% DMSO) at room temperature. The samples were allowed to equilibrate by agitation for 20 min at room temperature. Fluorescence polarization (excitation λ 485 nm, emission λ 525 nm, Cutoff λ 515 nm) measurements were taken using Spectra-Max M5 Microplate Reader (Molecular Devices). There was no change in the FP signal of FITC alone upon addition of TTR, which indicates that FITC has no interaction with TTR. Nonspecific FP, produced by the free fluorescent probe 5 as well as by binding of 5 to the plate, was equal to 70±10 mP.

Displacement Binding Experiments for Assay Development.

The affinity of test compounds to TTR was determined as follows. In a black 96-well plate (Costar), probe 5 (100 nM) was incubated with TTR (200 nM) in assay buffer (PBS pH 7.4, 0.01% Triton-X100, 1% DMSO in 150 µL final volumes) at room temperature. Compounds (1,2, Thyroxine, or diclofenac) were added to the wells in serial dilutions (50 µM to 10 nM). All compounds appeared to be soluble under the assay conditions. The samples were allowed to equilibrate by agitation for 20 min at room temperature and the fluorescence polarization was measured as described above. The data were fit to the following equation $[y=(A-D)/(1+(x/C)^B)+D]$ where A=maximum FP signal, B=slope, C=apparent binding constant ($K_{app}$), and D=minimum FP signal. The apparent binding constant was reported as mean for triplicate experiments and the best data fit was determined by $R^2$ value.

High-Throughput Assay Format.

The HTS FP measurements were performed using black 384-well plates (E&K Scientific, # EK-31076) on an Analyst GT (Molecular Devices, Inc.). Approximately 120,000 compounds from the Stanford IITBC library were screened (Diverse compounds form Chemdiv, Chembridge, SPECS. and LOPAC$^{1280}$-1280 compounds Library of Pharmacologically Active Compounds from Sigma). HTS source plates containing 10 mM and 1 mM stock solution in DMSO were thawed and spun down just prior to testing. 10 µL blank control of assay buffer (PBS pH 7.4, 0.01% Triton-X100) was added to column 24 of the 384 well assay plate and 10 µL of 1.5 nM of the probe 5 was added to column 23 of the assay plate. 10 µL mixture of probe 5 (1.5 nM) and TTR (50 nM) was added to columns 1 to 22 of the assay plate. 50 nL of compounds (10 mM and 1 mM stocks) were then added to columns 2 to 22 of the assay plate (compounds were screened at two concentration 50 µM and 5 µM). The plates were incubated at room temperature for ~5 minutes and the fluorescence polarization was read in the Analyst GT (top read, bottom of well, Ex 485, Em 530, dichrioc 505, 10 second mix). A second read was also performed after ~2-5 hours. All FP measurements are expressed in millipolarization (mP) units calculated using the equation $mP=1000 \times [(I_S-I_{SB})-(I_P-I_{PB})]/[(I_S-I_{SB})+(I_P-I_{PB})]$, where $I_S$ is the sample parallel emission intensity measurement, $I_P$ is the sample perpendicular emission measurement, and $I_{SB}$ and $I_{PB}$ are the corresponding measurement for blank assay buffer. A very good dynamic range (60 m-220 mP) was observed for the assay.

Determination of IC50 Using the FP Assay.

Serial dilutions of test compounds (at least 8-point duplicate) were added to a solution of probe 5 and TTR in assay buffer (15 µL final volume). The plates were spun at 1.2K rpm and then read on Analyst GT as described above. A second read was performed after ~3 hours.

Biotinylation of TTR.

To an ice-cold solution of TTR (20 µM) in PBS was added EZ-Link Sulfo-NHS-LC-Biotin at a ratio of ~2:1 (biotin: TTR) (minimal biotinylation) and the solution was incubated at room temperature. After 1 hour, un-reacted biotin was removed by passing the sample over a fast (FPLC) desalting column (Superdex™ 75) equilibrated with PBS. This step was not sufficient to remove all of the unreacted biotin, therefore, the sample was dialyzed twice against PBS for 2 hours at 4° C.

Surface Plasmon Resonance (SPR) Assay for TTR-Ligands Interaction.

SPR measurements were performed at 25° C. using a Biacore T100 (GE Healthcare) instrument equilibrated in 1% DMSO in PBS as a running buffer. After pretreatment of the streptavidin-coated chip (Sensor Chop SA, Biacore), ~4000 RU biotinylated TTR was immobilized on one channel leaving the second flow channel as a blank (streptavidin alone) control. For binding measurements, HTS hits were diluted in running buffer (1% DMSO/PBS) and different dilution series were flowed over the chip at 50 µL/min (150 µL/60 s injection, 600 s wash). A zero concentration sample was used as a negative control. The kinetic data was fitted to a one-to-one binding model using Biacore T100 evaluation software.

Fibril Formation Assay for TTR Amyloidogenesis.

The efficacy of each compound to inhibit TTR amyloidogenesis was determined by monitoring the turbidity of TTR aggregation at acidic pH, as described previously. 5 µL of test compound (1.44 mM in DMSO) was added to a 495 µL of WT TTR (7.2 µM solution in 10 mM phosphate, pH 7.0, 100 mM KCl, 1 mM EDTA) in disposable cuvette. The sample was incubated at room temperature for 30 min after which the pH was lowered to 4.4 by addition of 500 µL of 100 mM acetate buffer (pH 4.2, 100 mM KCl, 1 mM EDTA) (final compound and TTR concentrations were 7.2 µM and 3.6 µM, respectively). The final 1 ml sample mixture was vortexed, then incubated at 37° C. for 72 hours, after which the sample was vortexed and the optical density was measured at 400 nm on a Beckman DU® 640 spectrophotometer. The percentage of fibril formation was determined by normalizing the optical density in the presence of test compound by that of TTR incubated with 5 µL of pure DMSO (representing 100% fibril formation or 0% inhibition). The optical density was also corrected for the absorption of all test compounds in the absence of TTR. For the kinetic fibril formation assay (FIG. 5B), the final compound and TTR concentrations were 3.0 µM and 3.6 µM, respectively. The optical density (400 nm) was measured as described above at 0, 24, 48, 72, 96, and 120 hours. All assays were performed in triplicate and the average values obtained are presented.

Cell-Based Assay.

Cells:

The human neuroblastoma IMR-32 cell line (CCL-127 ATCC) was maintained in advanced DMEM (Mediatech, Manassas, Va.), supplemented with 5% FBS, 1 mM Hepes buffer, 2 mM L-glutamine, 100 units/mL penicillin and 100 µg/mL streptomycin. The human cardiac cell line AC16 was maintained in DMEM:F12 (1:1) supplemented with 10% FBS, 1 mM Hepes buffer, 2 mM L-glutamine, 100 units/mL penicillin and 100 µg/mL streptomycin. Two to 4-day-old cultures (~70% confluent) were used for the experiments.

Cell Assays:

Recombinant WT TTR purified in the cold in HBSS (Mediatech, Manassas, Va.) was used as a cytotoxic insult to IMR-32 cells and the amyloidogenic V1221 TTR was used as cytotoxic insult to cardiac AC16 cells. Candidate compounds (16 mM in DMSO) were diluted 1:1000 with WT TTR or V1221 TTR (16 mM in HBSS, filter sterilized) or with HBSS only. The mixtures were vortexed and incubated for 24 h at 4° C. WT TTR or V1221 TTR (16 mM in HBSS) containing the same amount of DMSO than TTR/candidate compound mixtures was prepared in parallel and incubated under the same conditions.

The neuroblastoma IMR-32 and the cardiac AC16 cells were seeded in black wall, clear bottom, tissue culture treated 96-well plates (Costar) at a density of 6,000 cells/well and 250 cells/well, respectively in Opti-mem supplemented with 5% FBS, 1 mM Hepes buffer, 2 mM L-glutamine, 100 units/mL penicillin and 100 µg/mL streptomycin, 0.05 mg/mL CaCl2 and incubated overnight at 37° C. The medium was then removed and replaced immediately by the TTR/compound or HBSS previously diluted 1:1 in Opti-mem supplemented with 0.8 mg/mL BSA, 2 mM Hepes buffer, 4 mM L-glutamine, 200 units/mL penicillin, 200 µg/mL streptomycin and 0.1 mg/mL CaCl2. The cells were incubated 24 h at 37° C. after which cell viability was measured. When IMR-32 cells where used the 96 well plates were spun for 30 min at 1,500×g at 4° C. one hour after TTR/compounds had been seeded to allow the poorly adherent cells to re-attach to the wells.

Cell Viability Assay:

Cell viability of the cells treated with TTR or TTR/candidate compound was evaluated by a resazurin reduction assay. Briefly, 10 µL/well of resazurin (500 mM, PBS) was added to each well and incubated for 2-3 h at 37° C. Viable cells reduce resazurin to the highly fluorescent resorufin dye, which is quantitated in a multiwell plate reader (Ex/Em 530/590 nm, Tecan Safire2, Austria). Cell viability was calculated as percentage of fluorescence relative to cells treated with vehicle only (100% viability) after subtraction of blank fluorescence (wells without cells). All experimental conditions were performed at least in six replicates. Averages and SEM corresponding to 2 independently performed experiments were calculated.

Example 1

Design and Synthesis of the TTR FP Probe

The first step in developing a FP assay is the design of a fluoresceinated ligand that binds to TTR. Typically, such ligand would be a TTR binder attached to a fluorescent tag through a suitable linker. The linker is usually included to minimize steric clashes of the fluorophore with binding site residues. Binding is measured by an increase in the FP signal, which is proportional to the decrease in the rate of tumbling of a fluorescent ligand upon association with macromolecules such as proteins.

Figure 1B:
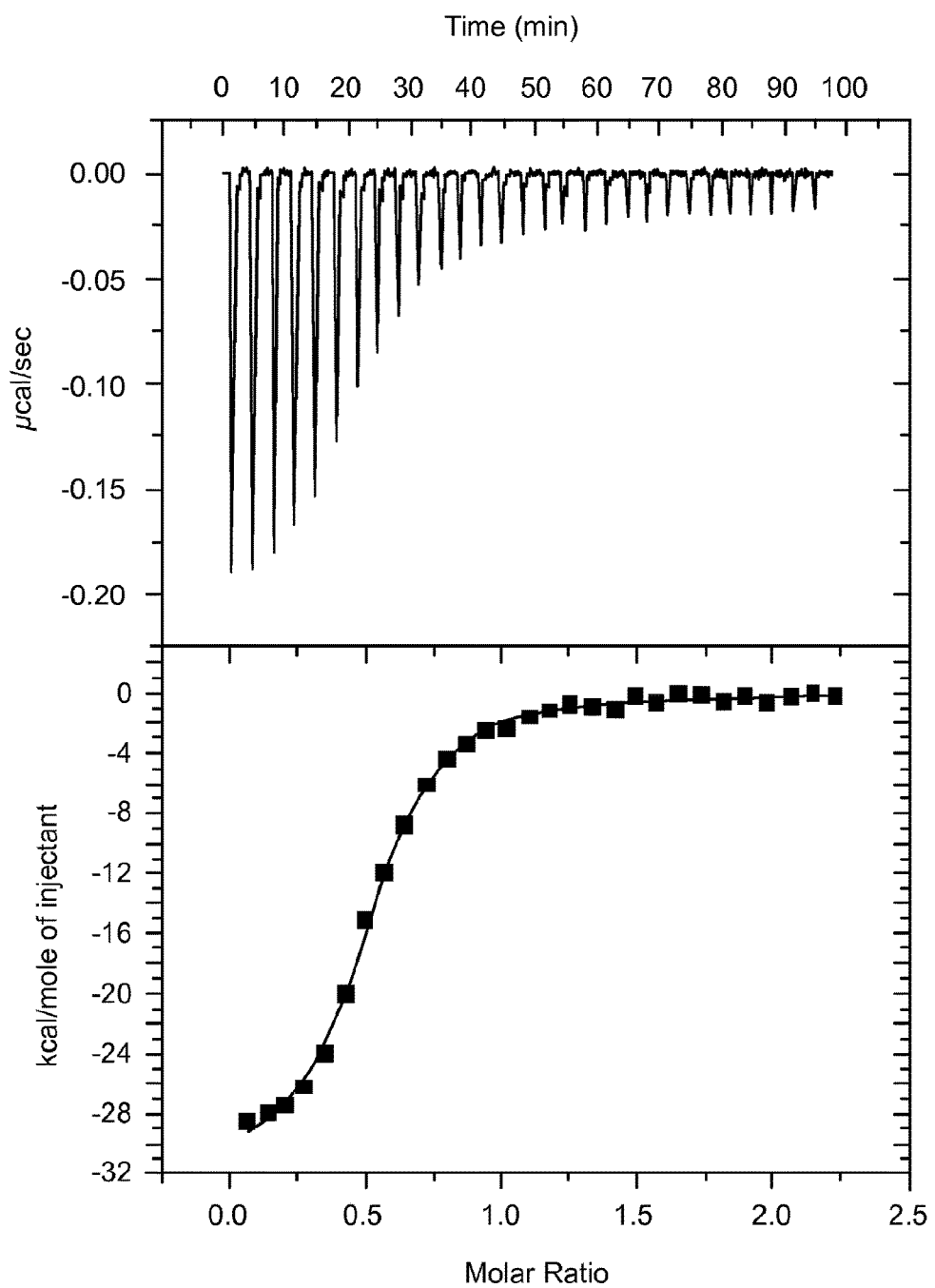
FIGS. 1B-1E depict results of calorimetric titration of ligands against TTR.
Figure 1C:
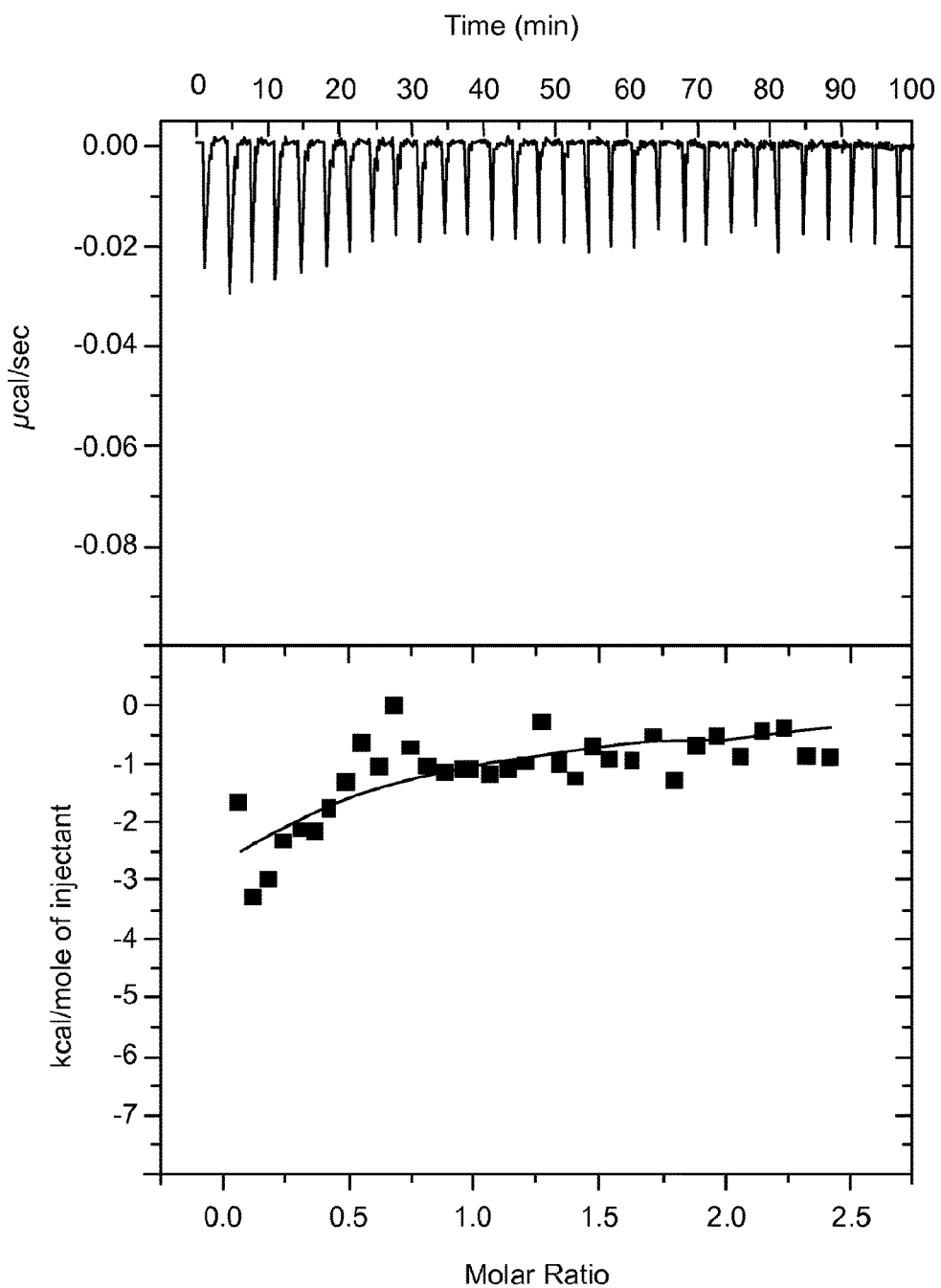
Figure 1D:
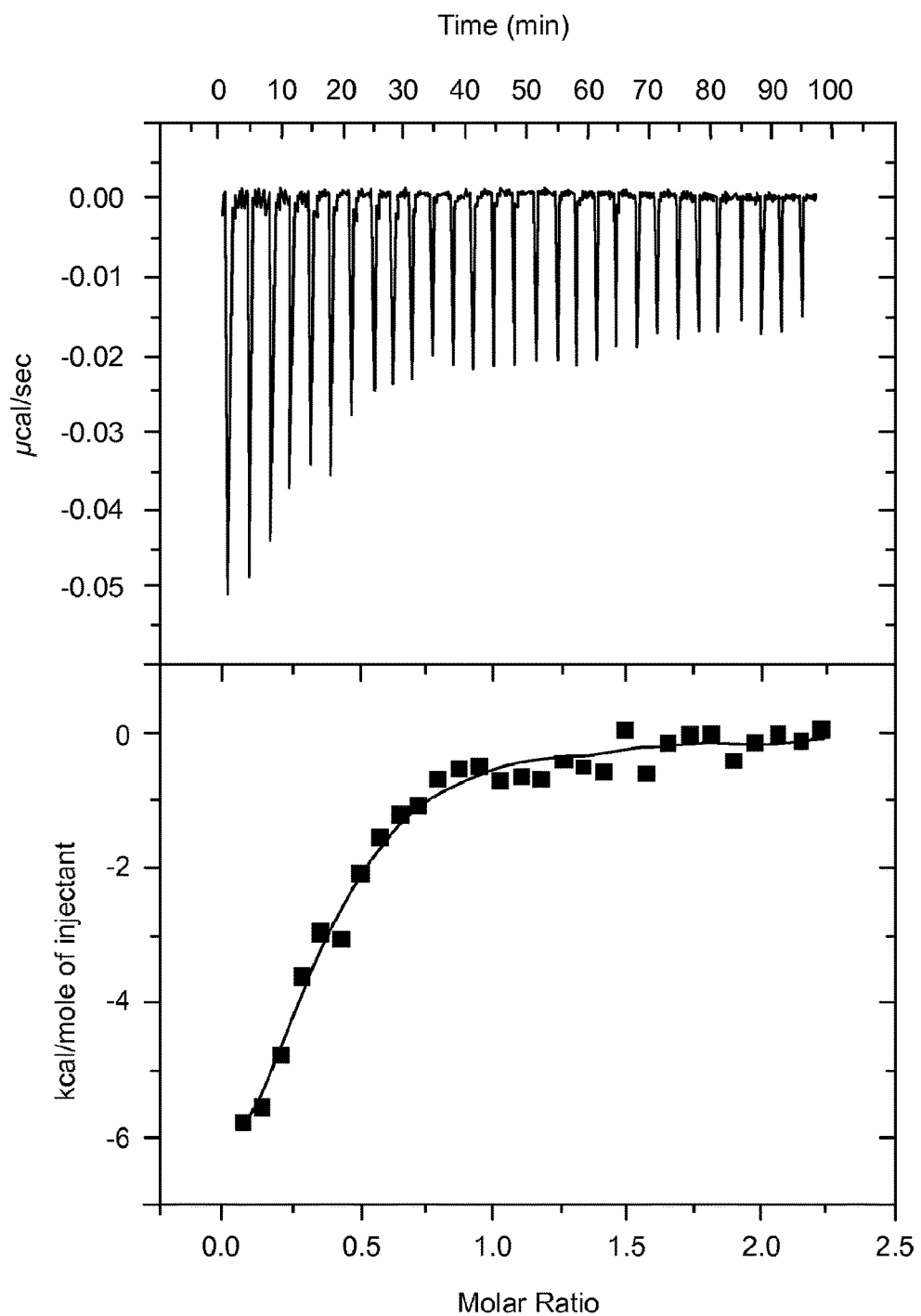
Figure 1E:
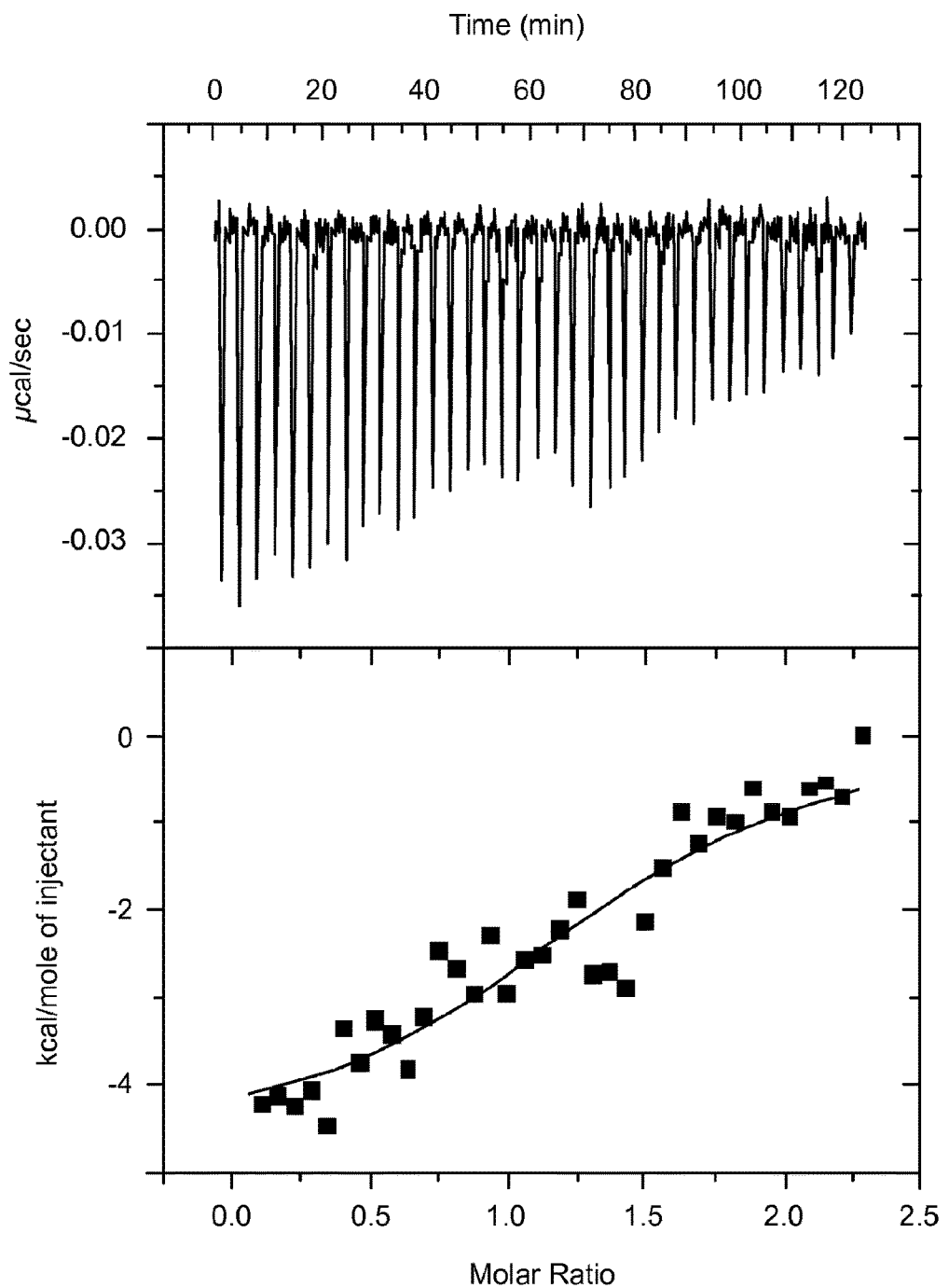
Figure 2A:
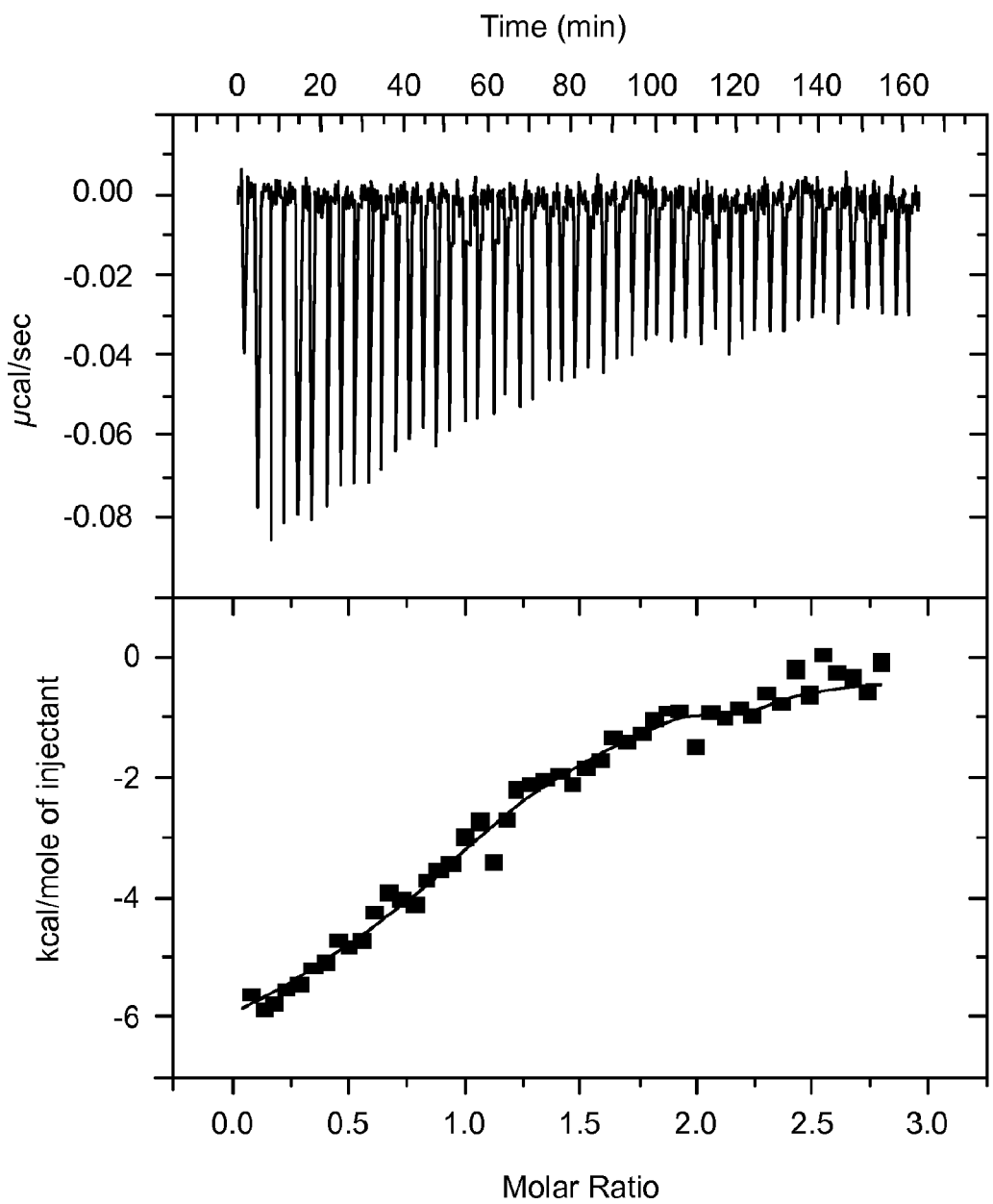
FIGS. 2A-2C depict results from the assessment of the binding affinity of probe 5 to TTR.

Initially, the NSAID diflunisal analogue 1 (FIG. 1A) which has high affinity for TTR ($K_d$=80 nM) and is a potent inhibitor of TTR aggregation was tested as a fluoresceinated ligand. X-ray crystallographic data showed that compound 1 binds to the TTR T4-binding site with its carboxylate-substituted hydrophilic ring oriented in the outer binding pocket and exposed to solvent. Therefore, a poly(ethylene glycol) (PEG) diamine linker was attached to the carboxylic acid of compound 1 by amide bond to produce compound 2 (FIG. 1A). The binding affinities of 1 and 2 to TTR were evaluated using isothermal titration calorimetry (ITC). As reported earlier, compound 1 was found to have a strong binding affinity to TTR (wild type TTR form human plasma) ($K_d$=72.5±4.7 nM, FIG. 1B). However, attaching a linker to the carboxylic acid of 1 (compound 2) resulted in a drastic loss of binding affinity ($K_d$>3.29 µM, FIG. 1C), which suggests a critical role of the carboxylic acid of 1 in electrostatic interaction with the Lys 15 ε-ammonium groups in the outer pocket of TTR. Wiseman et al. reported the NSAID diclofenac analogue 3 (FIG. 1A) as potent TTR aggregation inhibitors. The crystal structure of compound 3 bound to TTR demonstrates that the phenolic hydroxyl between the two chlorine atoms points directly out of the binding pocket into the solvent. Thus, this position would be a potential site for linker attachment. Using Mitsunobu coupling, a PEG linker was attached to the phenol group of compound 3 to generate ligand 4 (FIG. 1A). The binding affinity of 4 to TTR was evaluated using ITC, which demonstrated that compound 4 has very good affinity for TTR ($K_d$=284.9±58.1 nM, FIG. 1D). This affinity is comparable to the affinity of the known TTR binder diclofenac ($K_d$=370.4±145.4 nM, FIG. 1E). Having confirmed that attaching a linker to 3 did not abrogate the binding affinity, compound 4 was then coupled to Fluorescein isothiocyanate (FITC) to produce the desired FITC-coupled TTR probe 5 (FIG. 1A). Attaching FITC to 4 resulted in ~3-fold decrease in binding affinity to TTR ($K_d$ for 5=819.7±129.7 nM, FIG. 2A). Fortunately, the affinity of 5 for TTR was not so strong that unreasonably high concentrations of competitive binders were required to displace it.

Example 2

Evaluation of the Binding of Probe 5 to TTR Using FP

The binding of probe 5 to TTR was evaluated to test its suitability for the FP assay.

Figure 2B:
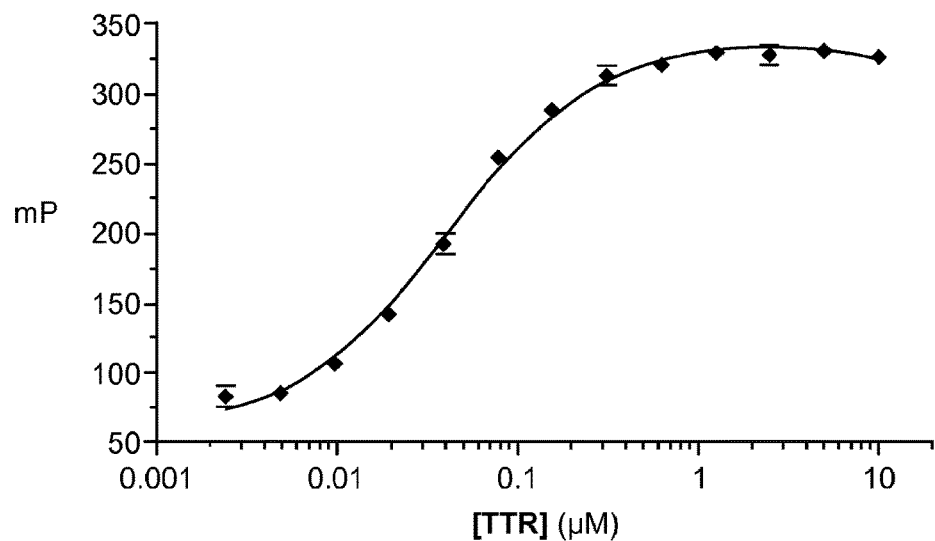

The binding of 5 for TTR was determined using a standard saturation binding experiment. A fixed concentration of 5 (100 nM) was incubated with increasing concentrations of TTR, and the formation of the 5●TTR complex was quantitated using the increase in FP signal (excitation λ 485 nm, emission λ 525 nm) (FIG. 2b). As shown in FIG. 2b, at lower TTR concentrations, a low mP value was obtained; as the concentration of TTR increased, a greater fraction of fluorescent 5 bound to TTR and polarization progressively increased to reach saturation. A very good dynamic range, of approximately 70-330 mP, was measured for the assay.

Example 3

Displacement FP Assay for TTR Ligands

Figure 2C:
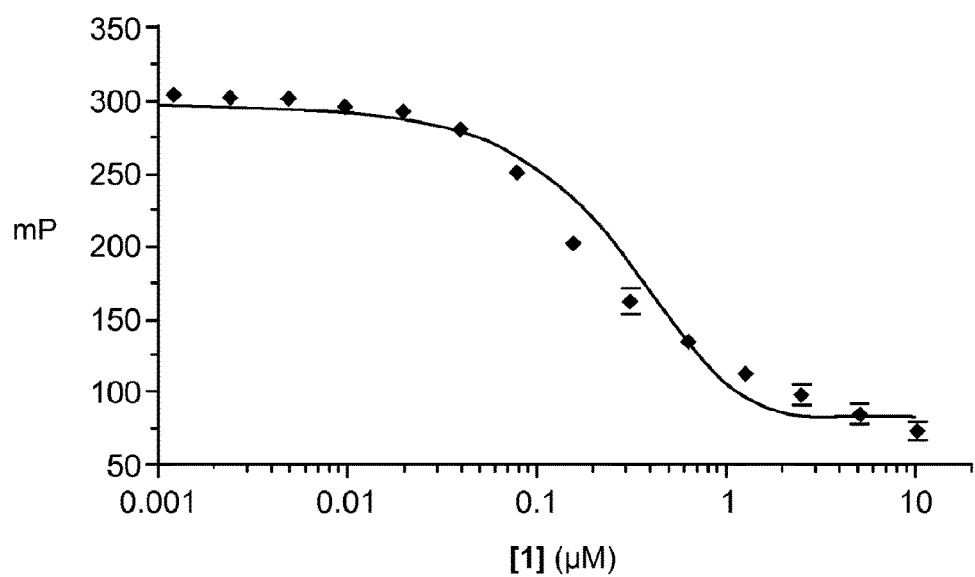
Figure 3A:
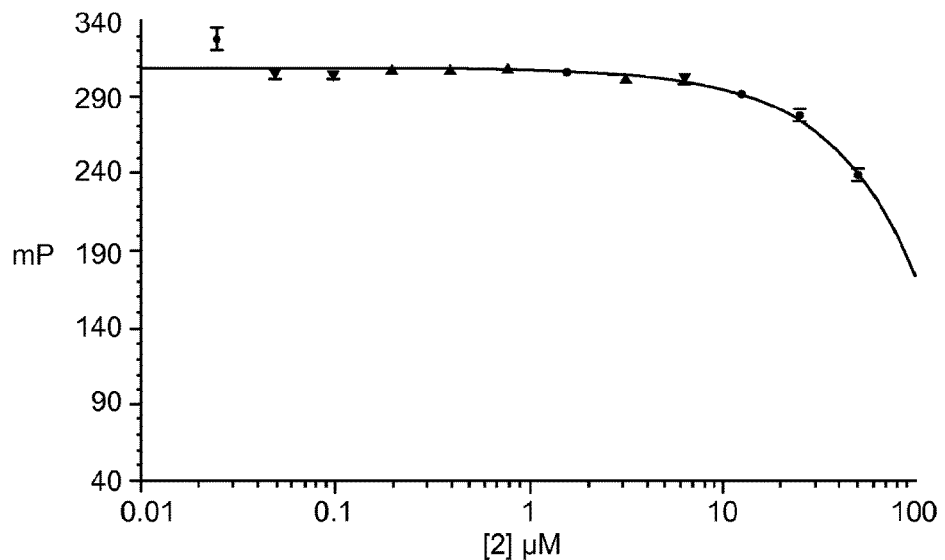
FIGS. 3A-3C depict displacement FP assay of TTR ligands.
Figure 3B:
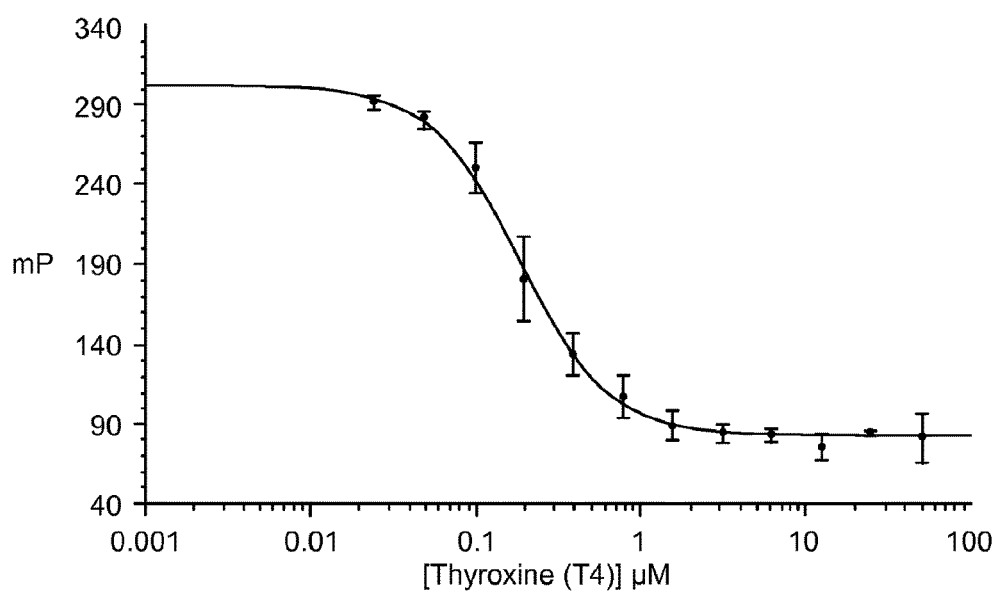
Figure 3C:
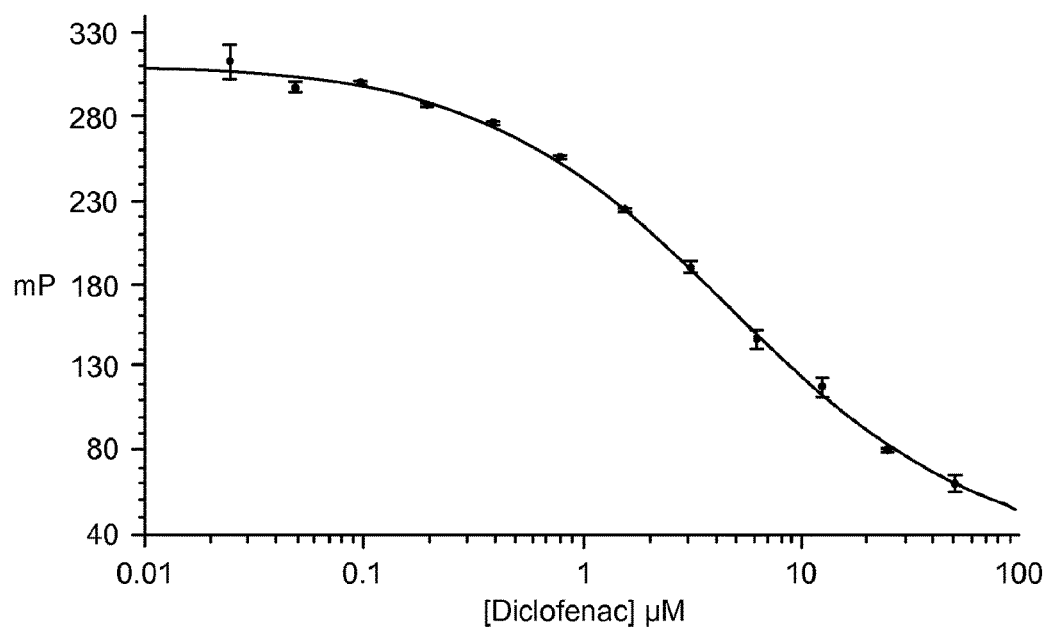

A displacement assay was used to assess the affinity of various known TTR binders to TTR. TTR (200 nM) was incubated with 100 nM of 5 and gave an assay window that is close to the maximum value (~300 mP). Increasing concentrations of compounds 1 or 2 were added to the 5●TTR complex and the fluorescence polarization was measured at equilibrium as described in the experimental procedures. As expected, compound 1, which has a strong binding affinity for TTR, gave a dose dependent decrease in the FP signal which confirms its binding to TTR. An equilibrium binding analysis of the data for 1 gave an apparent binding constant ($K_{app}$) of 0.231 µM ($R^2$=0.997) (FIG. 2c). In comparison, compound 2 (which is not a TTR ligand, based on ITC as described above) did not displace probe 5 from its TTR binding site (no decrease in the FP signal, FIG. 3A), which confirms 2 as a poor binder for TTR. Other known TTR binders were also tested to validate that the FP assay results correlate with a relevant biological parameter. Thyroxine (T4) ($K_{app}$=0.186 µM, $R^2$=0.998) and diclofenac ($K_{app}$=4.66 µM, $R^2$=0.999), were able to decrease the FP signal in a dose-dependent manner (FIGS. 3B and 3C). The main goal of the FP assay describe here is HTS and structure-activity relationship (SAR) development. Determination of $K_{app}$ of a ligand to TTR is quite sufficient for this purpose because a more informative, though cumbersome, ITC assay is available for more detailed ligand binding analysis. Importantly, these apparent binding constants, determined by FP assay, correlate very well with the data obtained by ITC (Table 2).

TABLE 2

Affinity of ligands as determined by ITC and FP.

| Ligand | ITC $K_d$ (µM) | FP $K_{app}$ (µM) |
|---|---|---|
| 1 | 0.0724 | 0.231 ($R^2$ = 0.997) |
| 2 | >3.289 | >50 |
| Thyroxine (T4) | 0.0197[a] | 0.186 ($R^2$ = 0.998) |
| Diclofenac | 0.370 | 4.66 ($R^2$ = 0.999) |

[a]Detemined by [$^{125}$I]thyroxine (T4) displacent assay ref

Example 4

Adaptation of the FP Assay for HTS

Figure 4A:
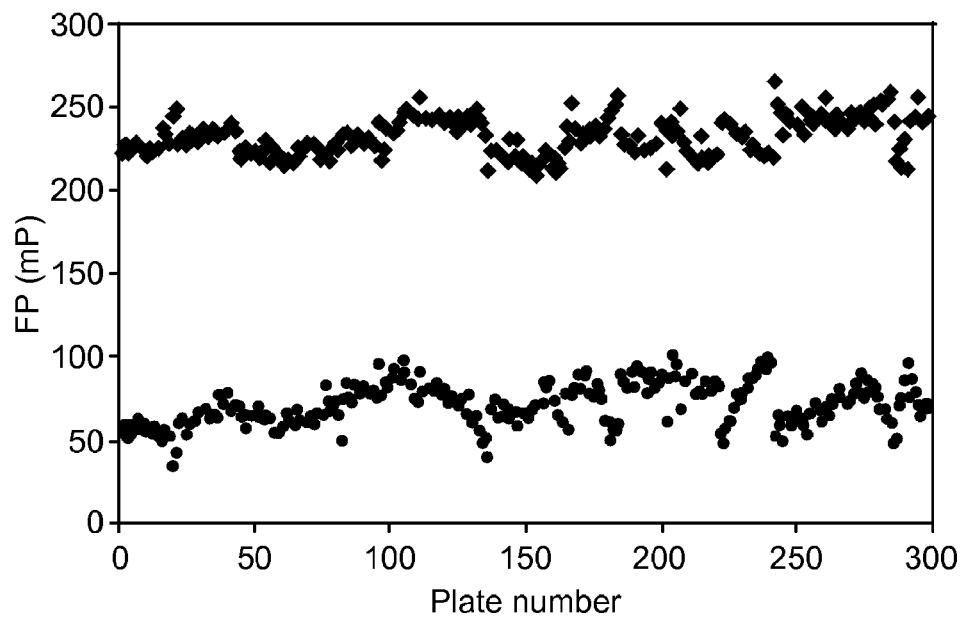
FIG. 4A shows average FP mP values for probe 5 incubated with TTR (MAX, ♦) or buffer (MIN, ●).
Figure 4B:
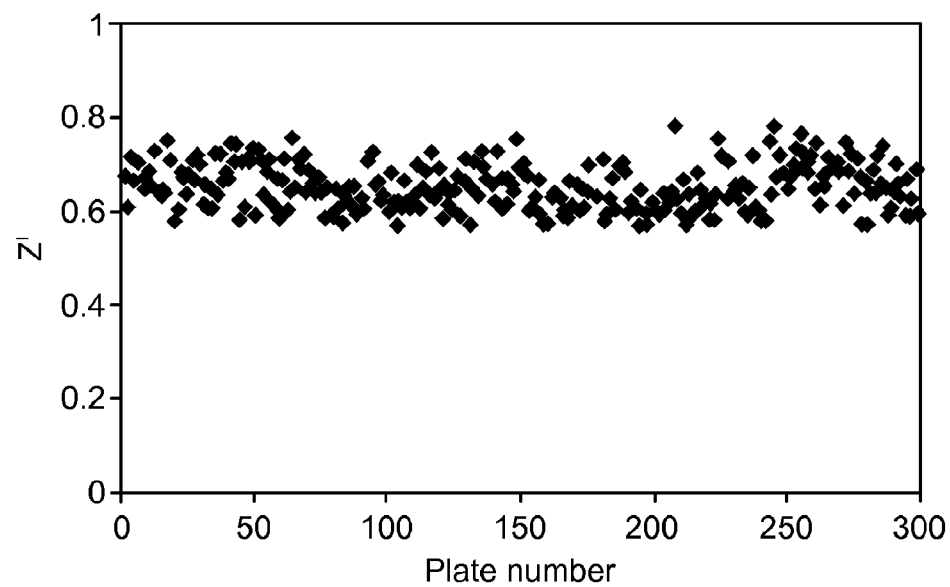
FIG. 4B shows Z' factor values calculated for each plate.

The FP assay was then adapted for HTS and used to screen ~120,000 small molecule library for compounds that displaced probe 5 from the T4 binding of TTR. The FP assay was performed in 384-well plate using very low concentration of probe 5 (1.5 nM) and TTR (50 nM) in a 10 pt assay volume. A detergent (0.01% Triton-X100) was added to the assay buffer to avoid any false positive hits from promiscuous, aggregate-based inhibitors. The assay demonstrated robust performance, with a very good dynamic range (~70-230 mP) and a Z' factor in the range of 0.57-0.78 (FIGS. 4A and 4B). "Hits" were defined as compounds that resulted in at least 50% decrease in fluorescence polarization and demonstrated relative fluorescence between 70 and 130%. Many fluorescence quenchers and enhancers having less than 70% and greater than 130% total fluorescence relative to a control, respectively, were excluded from the hit list. 200 compounds were designated as positive hits (0.167% hit rate). The 200 hits were then evaluated in a dose-response manner and their $IC_{50}$ (compound concentration that resulted in 50% decrease in the FP signal) values were determined. Among the 200 compounds screened, 33 compounds showed a dose-response effect on the FP and displayed IC50≤10 µM.

The top 33 hits (compounds with lowest FP $IC_{50}$) were then purchased again and their $IC_{50}$ was determined in a 10-point duplicate dose-response FP assay (Table 3).

TABLE 3

| Compounds Structures[a] | % fibril formation[b] | $IC_{50}$ (µM)[c] |
|---|---|---|
| 6 | 0.43 ± 0.61 | 0.277 |

TABLE 3-continued
| Compounds Structures[a] | % fibril formation[b] | IC$_{50}$ (μM)[c] |
|---|---|---|
| 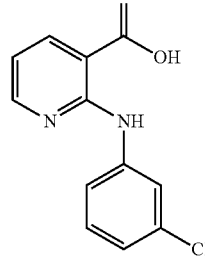 Niflumic acid | 4.83 ± 1.19 | 0.289 |
| 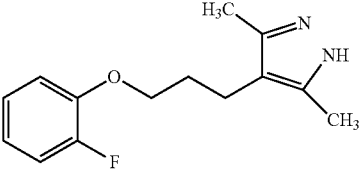 7 | 0.75 ± 1.06 | 0.296 |
| 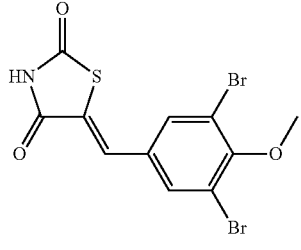 8 | 0.37 ± 0.53 | 0.301 |
| 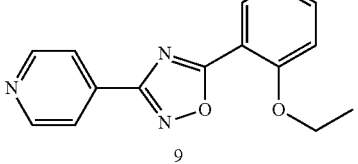 9 | 0.00 ± 0.00 | 0.3291 |
| 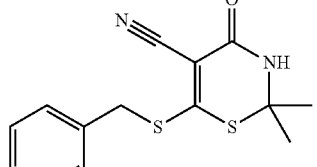 10 | 0.52 ± 0.73 | 0.433 |
TABLE 3-continued
| Compounds Structures[a] | % fibril formation[b] | IC$_{50}$ (μM)[c] |
|---|---|---|
| 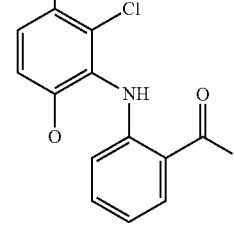 Meclofenamic acid | 3.87 ± 0.93 | 0.504 |
| 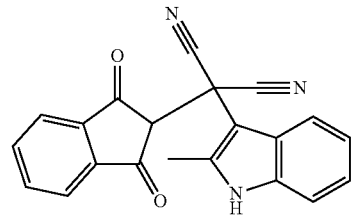 11 | 5.77 ± 3.91 | 0.586 |
| 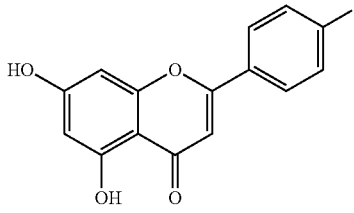 Apigenin | 10.07 ± 0.53 | 0.653 |
| 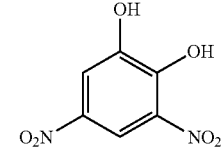 3,5-dinitrocatechol | 1.08 ± 0.59 | 0.741 |
| 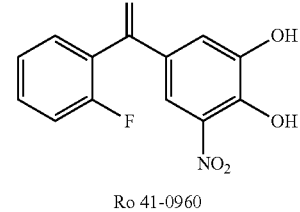 Ro 41-0960 | 0.32 ± 0.45 | 0.755 |
| 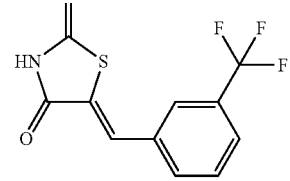 12 | 1.92 ± 1.08 | 0.815 |

TABLE 3-continued

| Compounds Structures[a] | % fibril formation[b] | IC$_{50}$ (μM)[c] |
|---|---|---|
| 13 | 3.22 ± 0.34 | 0.842 |
| 14 | 0.00 ± 0.00 | 1.152 |
| 15 | 0.00 ± 0.00 | 1.306 |
| 16 | 1.81 ± 2.56 | 2.585 |
| 17 | 9.60 ± 1.58 | 2.656 |
| 18 | 10.44 ± 4.88 | 3.349 |
| 19 | 13.91 ± 1.28 | 3.707 |
| Diclofenac | 11.56 ± 0.72 | 3.742 |
| 20 | 13.90 ± 5.52 | 3.927 |
| 21 | 24.36 ± 1.11 | 4.217 |

TABLE 3-continued

| Compounds Structures[a] | % fibril formation[b] | IC$_{50}$ (μM)[c] |
|---|---|---|
| 22 | 3.17 ± 4.48 | 4.786 |
| 23 | 28.77 ± 6.36 | 4.881 |
| 24 | 17.57 ± 4.81 | 4.933 |
| 25 | 43.25 ± 4.35 | 5.414 |
| 26 | 35.32 ± 3.69 | 5.604 |
| 27 | 38.38 ± 3.33 | 5.803 |
| 28 | 46.24 ± 1.33 | 8.69 |
| 29 | 48.25 ± 0.68 | 9.764 |
| 30 | 50.96 ± 1.98 | 10.039 |

TABLE 3-continued

| Compounds Structures[a] | % fibril formation[b] | IC$_{50}$ (µM)[c] |
|---|---|---|
| 31 | 49.43 ± 4.26 | 10.552 |
| 32 | 47.39 ± 1.94 | 10.957 |

[a]Chemical structure of TTR ligands.
[b]TTR amyloidogenesis inhibition activity (% fibril formation).
[c]IC$_{50}$ (compound concentration that resulted in 50% decrease in the FP signal).

Surface plasmon resonance (SPR) was used as an orthogonal biophysical technique to complement the screening assay and further test the hits. Solutions of the 33 hits were passed over immobilized TTR on streptavidin chip. All compounds identified by the screen as hits were confirmed as TTR binders (Based on observed SPR signal). It was shown previously that many NSAIDs and isoflavons are potent TTR aggregation inhibitors. Among the potent 33 hits identified in the screen, there were previously identified NSIADs (diclofenac, meclofenamic acid, and niflumic acid) and isoflavones (apigenin) (Table 3).

Example 5

Evaluation of Amyloidogenesis Inhibition by the HTS HITS

Figure 5A:
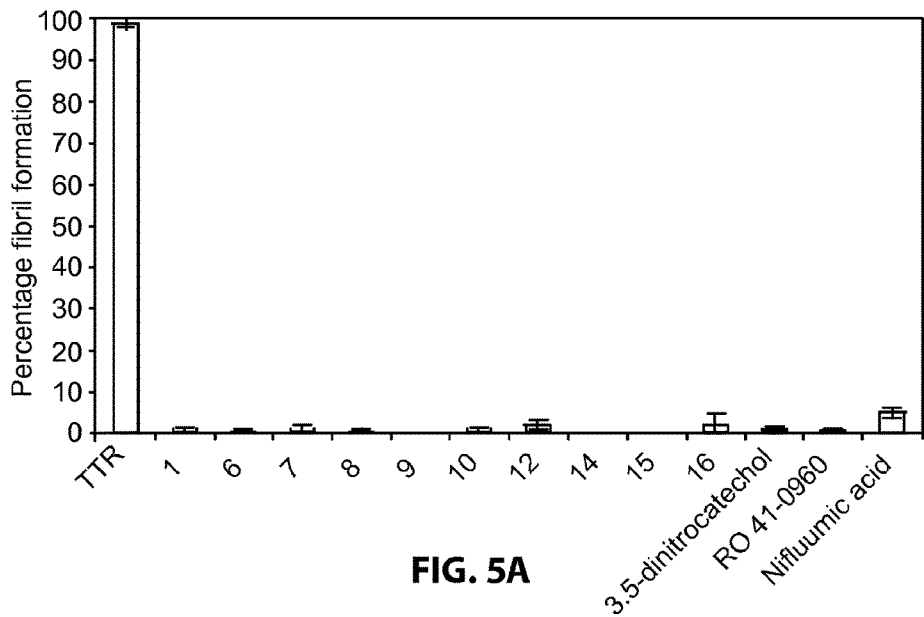
FIGS. 5A and 5B show evaluation of the potency of HTS ligands as TTR aggregation inhibitors.
Figure 5B:
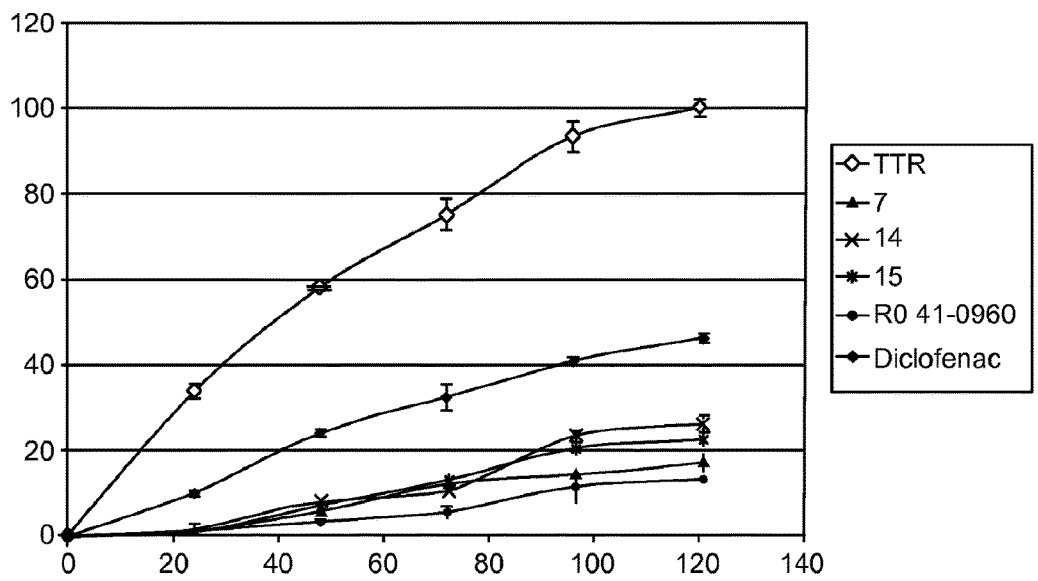

After confirming that the hits hind in the TTR T4-binding site, the efficacy with which these ligands inhibit TTR amyloidogenesis was evaluated using a previously reported acid-mediated fibril formation assay. This assay has been shown to be equivalent to monitoring amyloidosis using thioflavin T assay. TTR was preincubated with small molecules for 30 min at room temperature before amyloidosis was initiated (lowering pH to 4.4, incubation at 37° C.). Each compound was evaluated at a concentration of 7.2 µM relative to a TTR tetramer concentration of 3.6 µM (equivalent to 7.2 µM because each TTR tetramer has two T4 sites). This concentration is similar to concentration of TTR in human plasma. The amyloidogenesis inhibition efficacy of each compound was determined by monitoring the turbidity of TTR (400 nm). The extent of TTR amyloidogenesis was quantitated at a fixed time point (72 h). All amyloid fibril formation data was normalized to TTR amyloidogenesis in the absence of inhibitor, assigned to be 100% fibril formation. All the TTR ligands identified in the screen were inhibitors of TTR aggregation (<50% fibril formation) (Table 3). 23 out of the 33 hits were very good aggregation inhibitors (<20% fibril formation which corresponds to >80% inhibition of WT TTR fibril formation) among which 11 compounds demonstrated excellent TTR aggregation inhibition (<2% fibril formation) (FIG. 5A). Among the potent aggregation inhibitors were the NSAID niflumic acid and two compounds (3,5-dinitrocatechol and Ro 41-0960), which have been reported earlier as selective inhibitors of catechol O-methyl transferase (COMT). All other ligands have no reported biological activity against TTR amyloidogenesis. The ability of some of the potent ligands to inhibit TTR amyloidogenesis at substoichiometric concentration (TTR 3.6 µM and ligands 3.0 µM) were also tested. The aggregation inhibition was monitored over 5 days using the acid-mediated fibril formation assay (compared to 3 days for the fixed time point described above) (FIG. 5B). Compounds 7, 14, 15, and Ro 41-0960 inhibited fibril formation by >75% compared to diclofenac which resulted in only ~55% inhibition. This clearly indicates that these highly potent ligands are able to stabilize the TTR tetramer by binding to only one of the two T4 available. The most potent 11 aggregation inhibitors (along with niflumic acid as a control) were then evaluated for ability to prevent TTR cytotoxicity against neuron and cardiac cells. The chemical structures of all the ligands were confirmed by $^1$H NMR and high-resolution mass spectrometry (HRMS) and the chemical purity was >95%.

Example 6

Kinetic Stabilizers Prevent TTR-Induced Cytotoxicity Against Neurons and Cardiac Cells In tissue culture, amyloidogenic TTR variants are cytotoxic to cells derived from tissues that are target of amyloid deposition (Reixach, PNAS 2004). The human neuroblastoma cell line IMR-32 was used as a model for FAP (Reixach, PNAS 2004) and a human cardiac cell line AC16 was used as a model for SSA and FAC.

The amyloidogenic cardiac-specific V122I TTR variant was used as insult for the cells of cardiac origin (AC16). Interestingly, the non-amyloidogenic wild type TTR (WT TTR) purified at 4° C. (as opposed to room temperature) is cytotoxic to AC16, IMR-32 and other neuronal cell lines, possibly because of an altered tetramer structure that may facilitate amyloidogenesis (Reixach, BBRC 2006, 348:889-97, Lindhagen-Persson et al, Amyloid 2008 15:240). Cold-purified WT TTR was used as insult in the IMR-32 system. The advantage of using cold-purified WT TTR instead of an amyloidogenic variant that deposits in peripheral nerve (like V30M TTR) resides in the fact that WT TTR can be stored at −80° C. for months without changes in its cytotoxic properties, whereas other more amyloidogenic TTR variants are not stable and must be re-purified by gel filtration every time before use to remove the large soluble aggregates from solution which will render TTR non-cytotoxic (Reixach PNAS 2004).

Kinetic stabilizers prevented TTR-induced cytotoxicity by suppressing the release of monomers which result in misfolding and aggregation, whereas structurally related compounds with poor TTR binding capacity do not inhibit cytotoxicity (Reixach, BBRC 2006, 348:889-97, Lindhagen-Persson et al, Amyloid 2008 15:240).

The compounds under study were pre-incubated with WT TTR or V1221 TTR for 24 h at 4° C. at equimolar concentrations (8 µM) and added to IMR-32 cells or AC16 cells, respectively. Cell viability was measured after 24 h by a resazurin reduction assay. Metabolically active cells reduce the resazurin redox dye into resorufin, a soluble compound amenable to fluorescence quantification (O'Brien et al Eur J Biochem 267:5421). The percentage of viable cells was calculated relative to cells treated with vehicle only (cell culture media and DMSO)—which were assigned to be 100% viable. Resveratrol, a compound known to bind and kinetically stabilize native TTR preventing TTR-induced cytotoxicity was used as positive control.

Figure 6A:
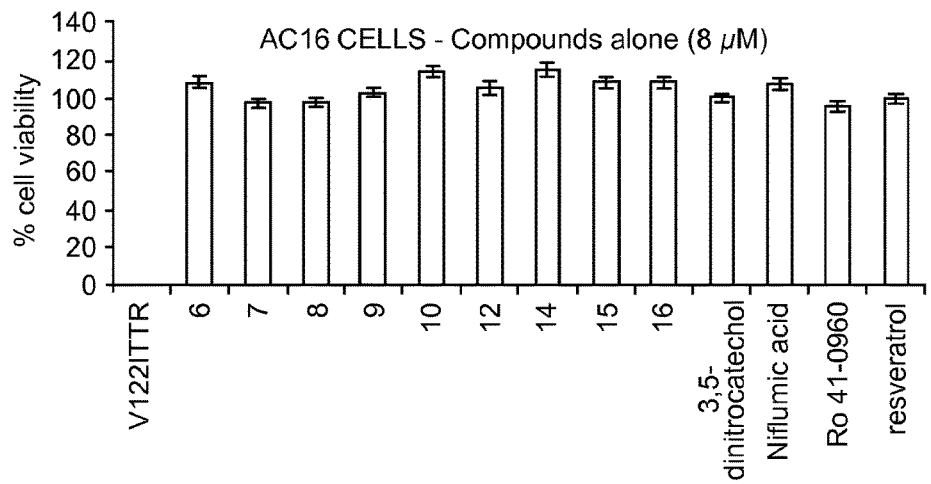
FIGS. 6A and 6B show results from measurement of cytotoxicity of TTR ligands (8 µM) on human AC16 cardiac cells (FIG. 6A) and human IMR-32 neuroblastoma cells (FIG. 6B).
Figure 6B:
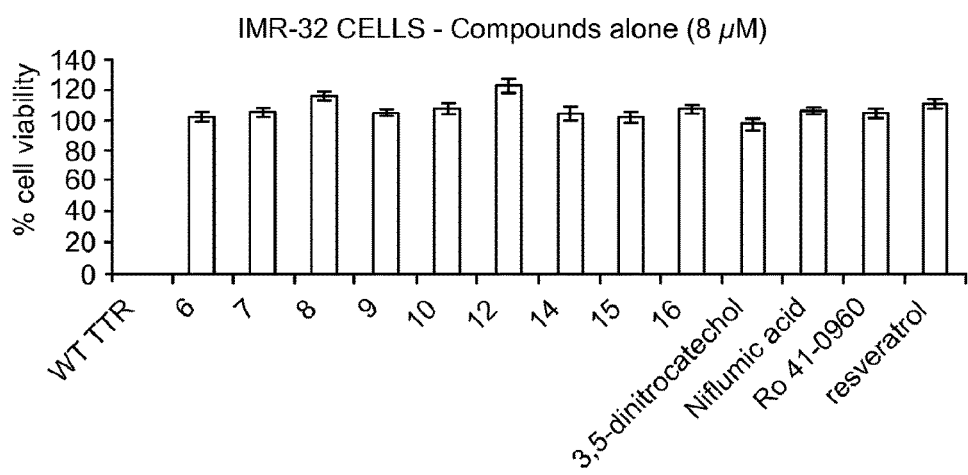

The results show that none of the compounds was cytotoxic to IMR-32 or to AC16 cells at the concentration tested (8 µM) (FIGS. 6A and 6B). Cell viability results are reported relative to cells treated with vehicle only (100% cell viability)(ref). Columns represent the means of two independently performed experiments (n=12) and the error bars represent standard errors.

Figure 6C:
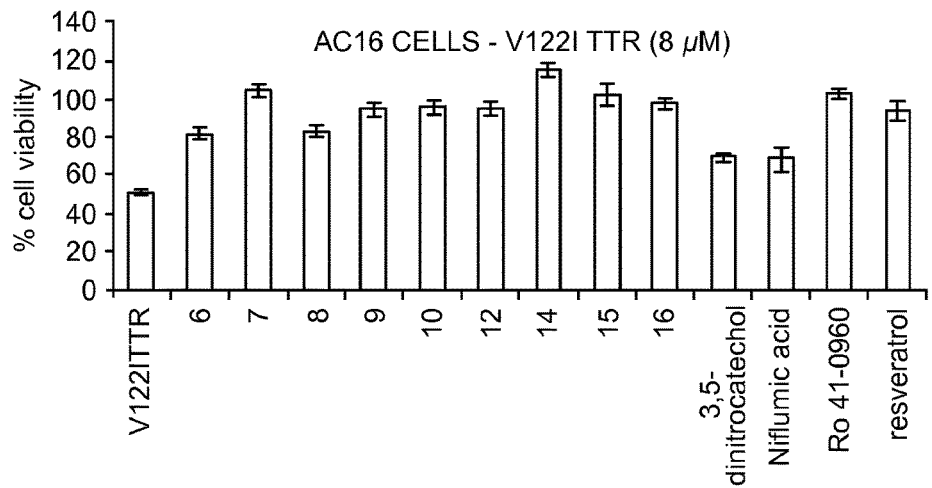
FIGS. 6C and 6D illustrate inhibition of V122 TTR and WT TTR cytotoxicity in human AC16 cardiac cells and IMR-32 neuroblastoma cells.
Figure 6D:
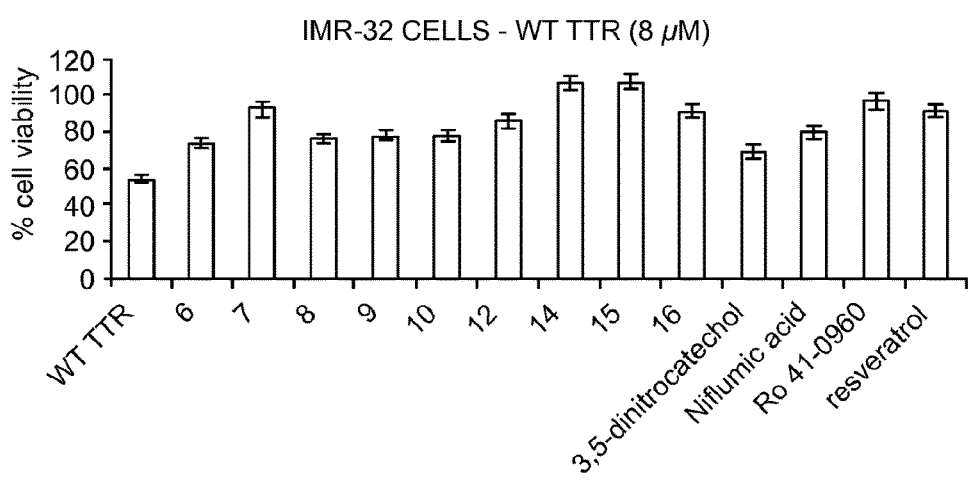

WT TTR and V1221 TTR alone reduced cell viability to 54±1% and 49±1% in IMR-32 and AC16 cells, respectively. For each cell culture assay (FIGS. 6C and 6D), the final concentration of both TTR and ligands was 8 µM. Cell viability was assessed using the resazurin reduction assay after 24 h. Cell viability results are reported relative to cells treated with vehicle only (100% cell viability)(ref). Columns represent the means of two independently performed experiments (n=12) and the error bars represent standard errors. Most of the compounds prevented TTR-induced cytotoxicity in both cell lines (FIGS. 6C and 6D). 3,5-dinitrocatechol was the only compound found to be poor inhibitor in both tissue culture systems. The NSAID niflumic acid was also a relatively poor inhibitor in the cardiac tissue culture system. It must be noted, however that even these so-called poorer inhibitors are able to prevent TTR-induced cytotoxicity in some degree in both cell lines (>68% cell viability compared to ~50% of TTR alone). Interestingly, compounds Ro 41-0960, 7, 14, and 15 demonstrated impressive potency and completely prevented TTR-induced cytotoxicity against both cardiomyocytes and neurons (FIGS. 6C and 6D).

Example 7

Determination of Binding Constants of HITS to TTR

Thyroxine (T4) and most reported TTR ligands bind TTR with negative cooperativity. The negative cooperativity of T4 binding to the two T4 sites appears to arise from conformational changes in TTR upon binding of T4 to first site. It is established that occupancy of only one T4 binding site within TTR is sufficient to impart kinetic stabilization on the entire tetramer. Thus, inhibitors exhibiting strong negative cooperativity would be ideal TTR stabilizers. ITC was used determine the binding constants of some of the hits to TTR and to evaluate presence or absence of cooperativity between the two TTR T4 sites. For most of the ligands studied, there are clearly two phases in the binding isotherms: a strong binding of the first ligand that almost saturates before the second weaker-affinity interaction becomes visible. This strongly indicates that these compounds exhibit negative cooperativity in binding to TTR. However, attempts to fit the data to interacting sites model of negatively cooperative binding yielded poor fits. Integration of the thermograms and subtraction of blanks gave binding isotherms that fit best a model that considers one set of binding sites. Dissection of the free energies associated with ligands binding to TTR suggests that these ligands interact differently with TTR (4).

TABLE 4

Isothermal Titration Calorimetry (ITC) analysis of the binding of ligands to human wild type TTR.

| Compounds | $K_d$ (nM) | ΔG | ΔH | TΔS |
| --- | --- | --- | --- | --- |
| 4 | 284.9 ± 58.1 | −8.93 ± 0.14 | −8.85 ± 0.95 | 0.08 ± 0.01 |
| 5 | 819.7 ± 129.7 | −8.30 ± 0.45 | −6.86 ± 0.36 | 1.44 ± 0.07 |
| 1 | 72.5 ± 4.7 | −9.74 ± 0.10 | −31.46 ± 0.37 | −21.72 ± 0.26 |
| 7 | 320.5 ± 27.6 | −8.86 ± 0.17 | −9.01 ± 0.13 | −0.15 ± 0.002 |
| Ro 41-0960 | 184.5 ± 26.5 | −9.18 ± 0.47 | −13.5 ± 0.32 | −4.3 ± 0.11 |
| 14 | 245.1 ± 40.1 | −9.02 ± 0.19 | −6.66 ± 0.22 | 2.36 ± 0.08 |
| Niflumic acid | 591.7 ± 146.6 | −8.49 ± 0.32 | −18.1 ± 1.71 | −9.57 ± 0.91 |
| Diclofenac | 370.4 ± 145.4 | −8.78 ± 0.59 | −4.69 ± 0.42 | 4.08 ± 0.37 |

Dissociation Constants ($K_d$) associated with the binding of ligands to TTR are expressed in nM. Thermodynamic Binding Parameters associated with ligand binding to TTR; Binding free energies (ΔG), enthalpies (ΔH), and binding entropies (TΔS) values are reported in units of kcal mol$^{-1}$.

Dissociation Constants ($K_d$) associated with the binding of ligands to TTR are expressed in nM. Thermodynamic Binding Parameters associated with ligand binding to TTR; Binding free energies (ΔG), enthalpies (ΔH), and binding entropies (TΔS) values are reported in units of kcal mol$^{-1}$.

Figure 7A:
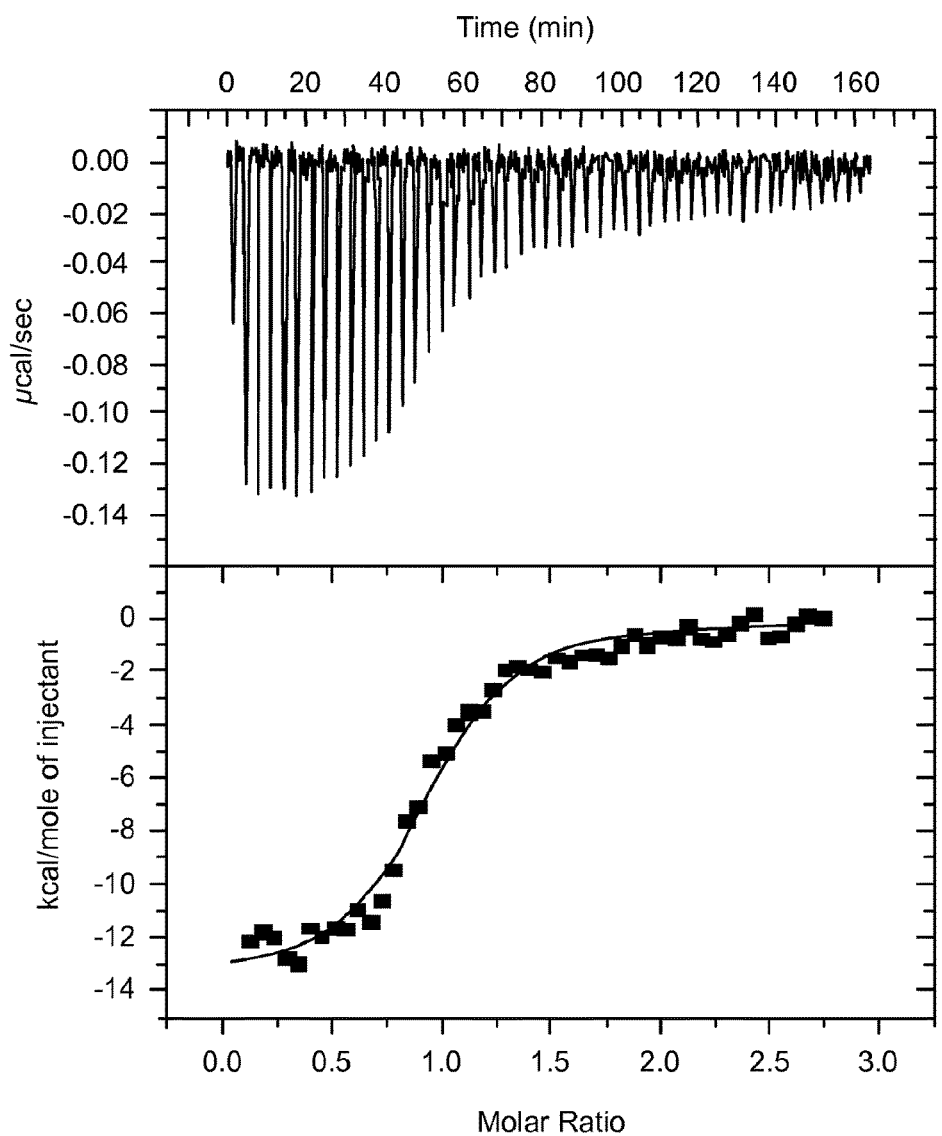
FIGS. 7A-7D illustrate calorimetric titration of Ro 41-0960 ($K_d$=184.5±26.5 nM) (FIG. 7A); niflumic acid ($K_d$=591.7±146.6 nM) (FIG. 7B); compound 7 ($K_d$=320.5±27.6 nM) (FIG. 7C); and compound 14 ($K_d$=245.1±40.1 nM) (FIG. 7D) for binding to TTR. Raw data (top) and integrated heats (bottom) from the titration of TTR (2 µM) with ligand (25 µM). The solid red line through the integrated heats represents the best fit binding isotherm to a one-to-one binding model.
Figure 7B:
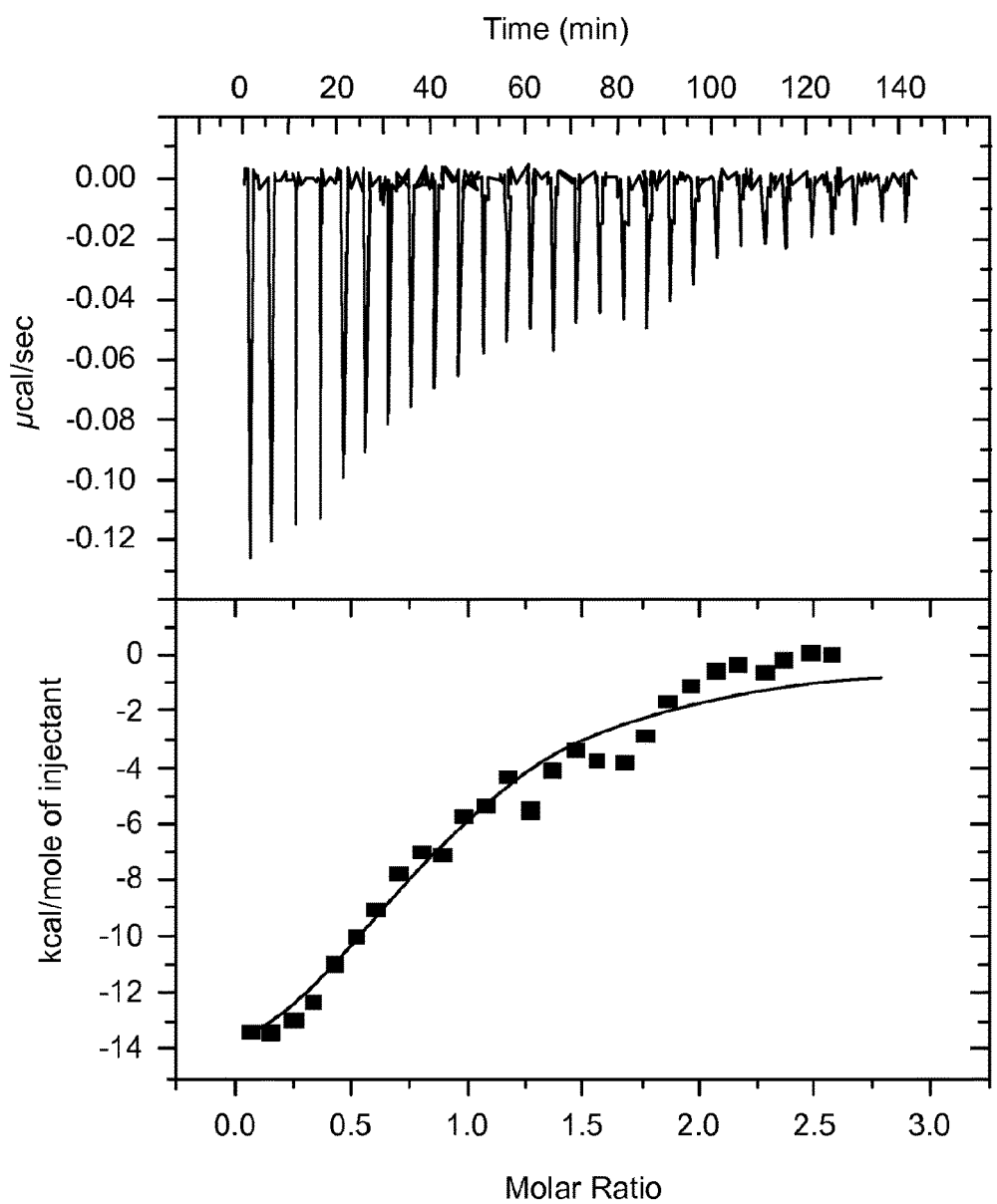
Figure 7C:
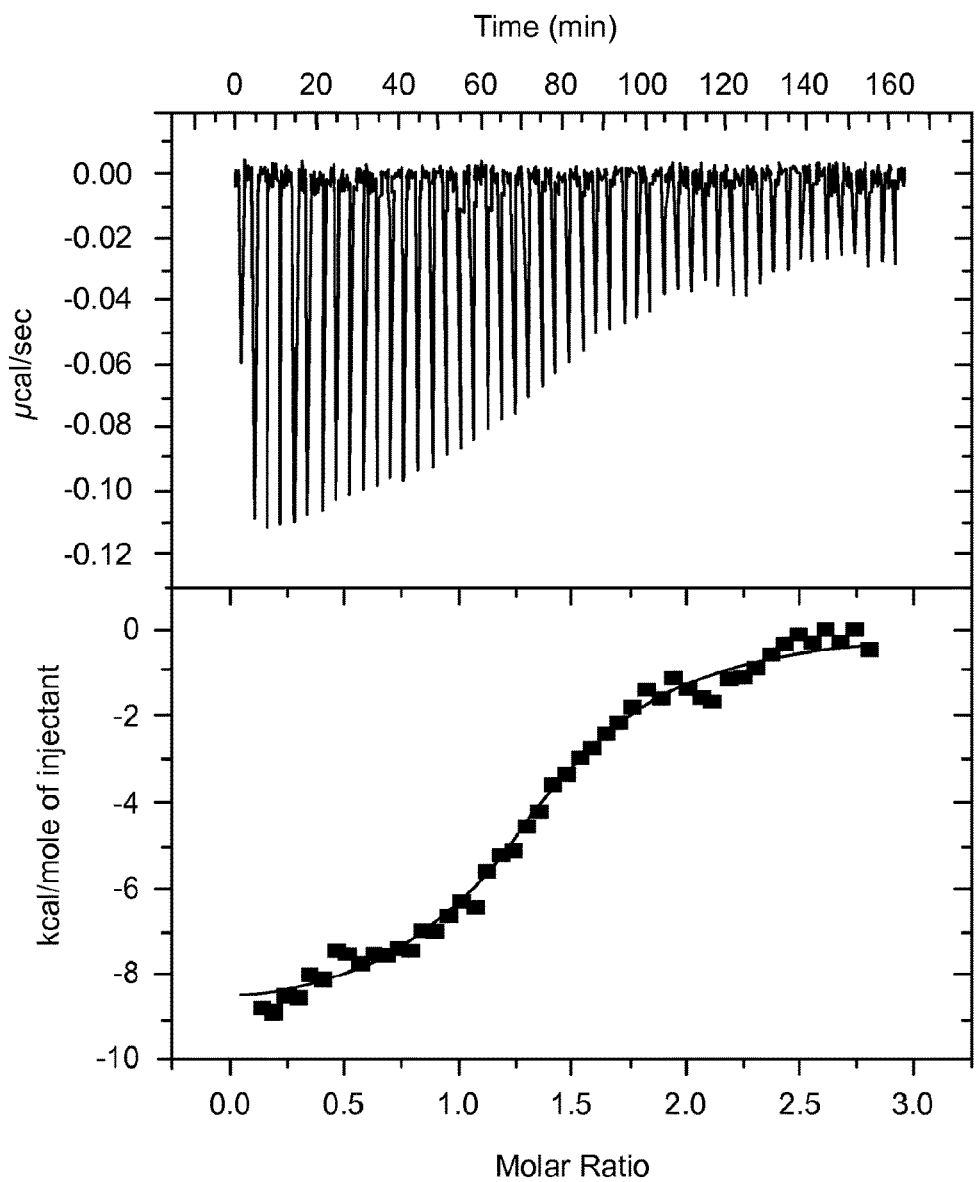
Figure 7D:
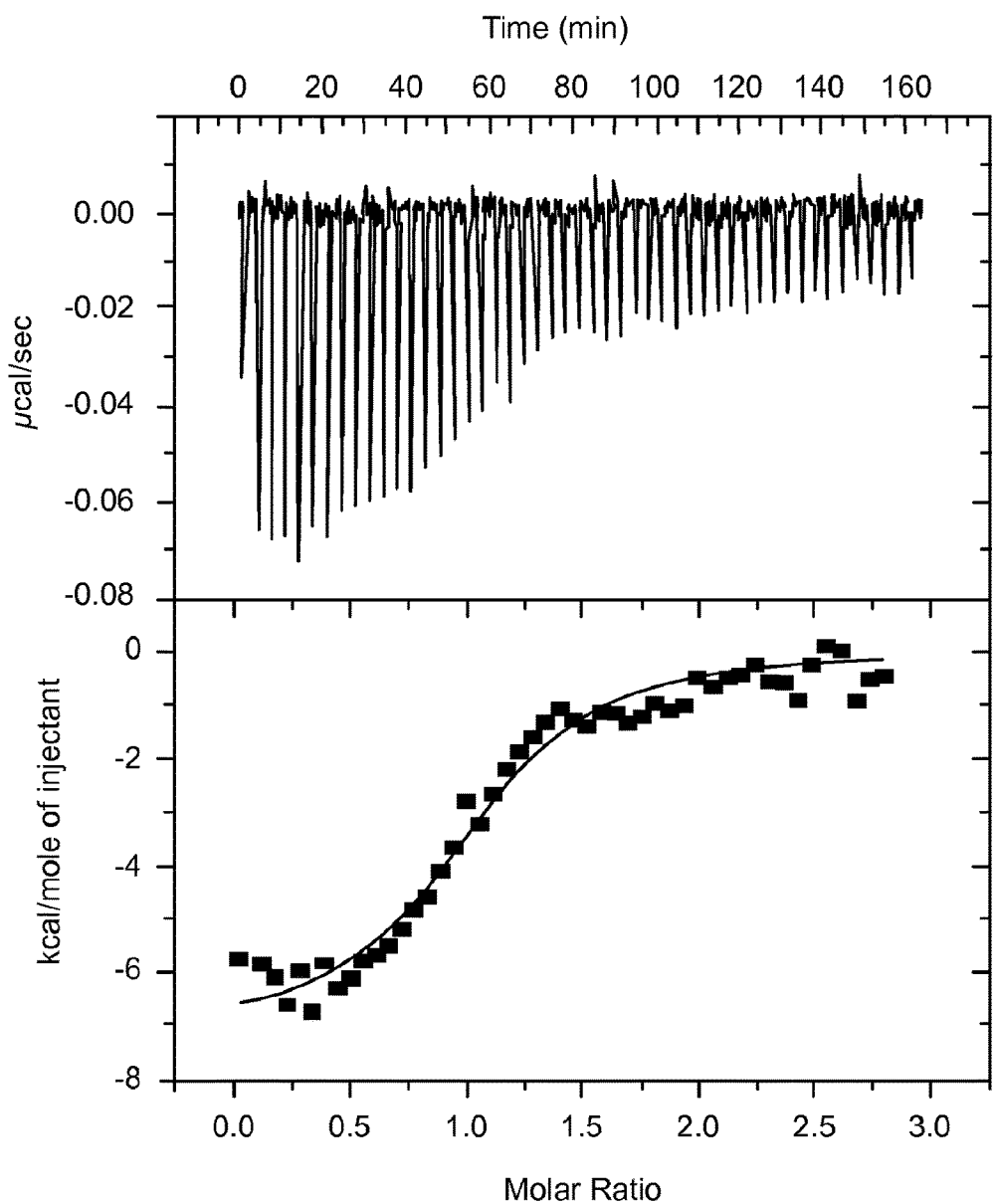

Ro 41-0960 exhibits an enthalpically driven (ΔG=−9.18±0.47 kcal mol$^{-1}$, ΔH=−13.5±0.32 kcal mol$^{-1}$) binding to TTR with unfavorable entropy (TΔS=−4.3±0.11 kcal mol$^{-1}$) (FIG. 7A). This mode of binding is similar to that of known TTR ligands such as niflumic acid (ΔG=−8.49±0.32 kcal ΔH=−18.1±1.71 kcal mol$^{-1}$ and TΔS=−9.57±0.91 kcal mol$^{-1}$) (FIG. 7B) and 1 (ΔG=−9.74±0.10 kcal mol$^{-1}$, ΔH=−31.46±0.37 kcal mol$^{-1}$ and TΔS=−21.72±0.26 kcal mol$^{-1}$). The binding of 7 to TTR is primarily enthalpically driven (ΔG=−8.86±0.17 kcal mol$^{-1}$, ΔH=−9.01±0.13 kcal mol$^{-1}$) and there is only mirror effect of the entropy associated with binding (TΔS=−0.15±0.002 kcal mol$^{-1}$) (FIG. 7C). On the other hand, there is strong favorable entropic contribution to the binding of compound 14 to TTR (TΔS=2.36±0.08 kcal mol$^{-1}$) (ΔG=−9.02±0.19 kcal mol$^{-1}$, ΔH=−6.66±0.22 kcal mol$^{-1}$) (FIG. 7D), which is similar to the favorable entropic contribution to the binding of diclofenac (TΔS=4.08±0.37 kcal mol$^{-1}$) (ΔG=−8.78±0.59 kcal mol$^{-1}$, ΔH=−4.69±0.42 kcal mol$^{-1}$). The binding of 14 to TTR does not cause major conformational changes the TTR tetramer structure. Thus, the favorable entropy associated with binding of 14, which is larger in size than other ligands, to TTR may be attributed to its ability to displace more water for the hydrophobic T4 site, and not due to ligand-induced conformational changes with the TTR tetramer.

Figure 7E:
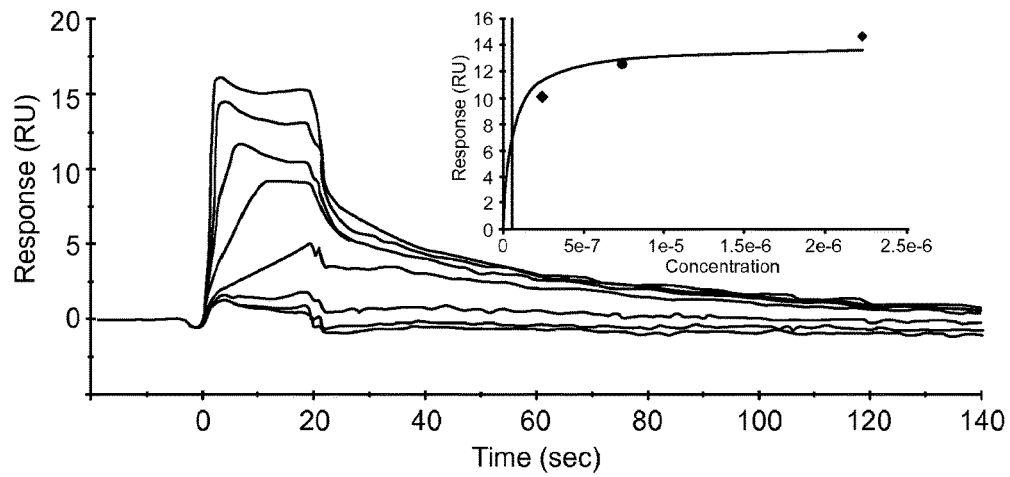
FIG. 7E shows a SPR sensogram showing concentration-dependent binding of ligand 7 to wild type biotinylated TTR on a streptavidin-coupled surface over a concentration of 1 nM to 2.2 in order of increasing RUs. Normalized RUs are plotted over a time course. Equilibrium binding analysis (inset) indicates a $K_d$ of 57.91±13.2 nM (SD).
Figure 8A:
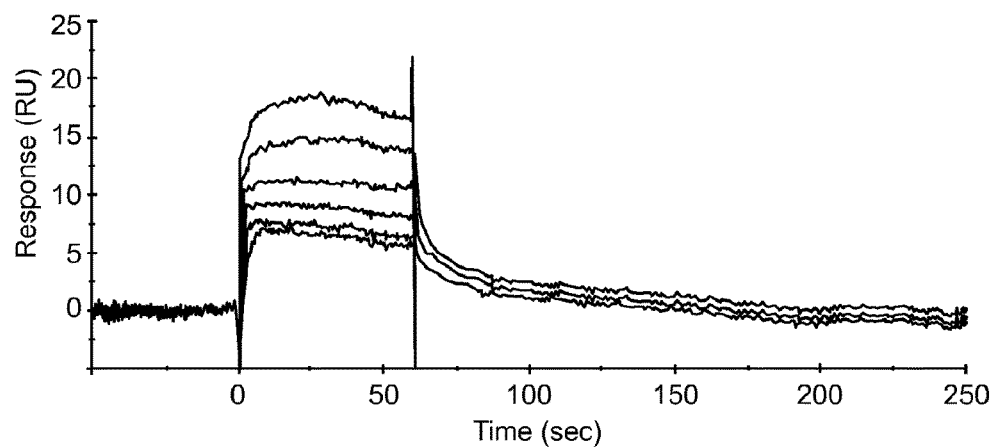
FIGS. 8A-8C depict assessment of the binding TTR ligands using SPR.
Figure 8B:
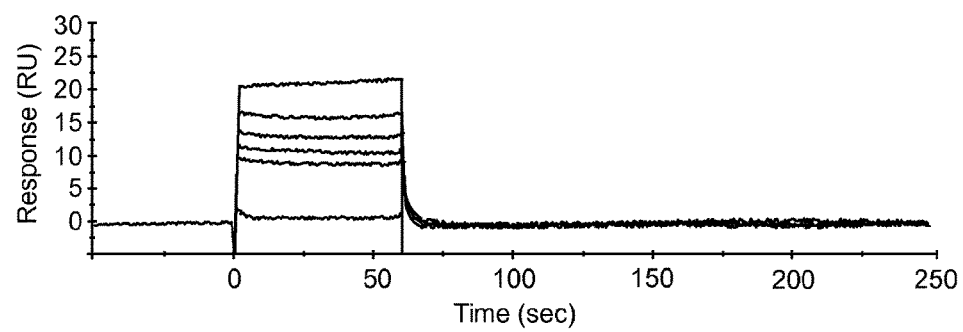
Figure 8C:
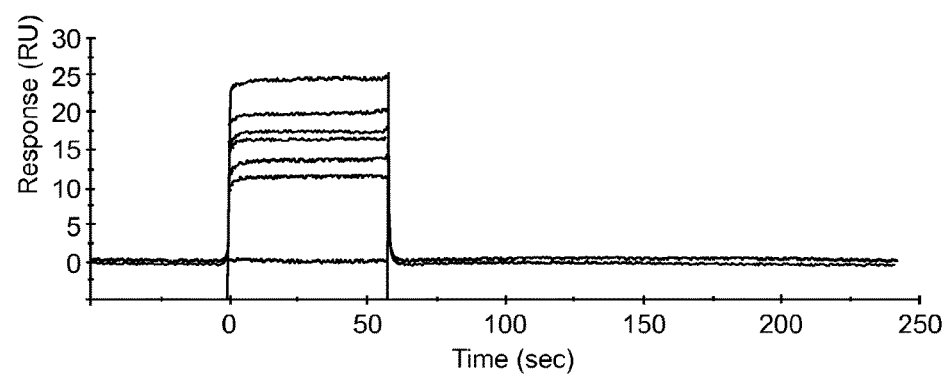

The interaction of some TTR ligands was further studied using SPR. The potent TTR ligand 7 exhibited binding to TTR in a concentration-dependent with a $K_d$ of 57.91±13.2 nM, determined by fitting steady state data (FIG. 7E). This difference between the $K_d$ values, form ITC and SPR, may be tolerated by considering the accuracy of the curve fitting and the effects of immobilization of the protein in the SPR experiment. Measurement of the binding kinetics of 7 to TTR gave a similar binding constant ($K_d$=20.22±2.04 nM) to the one determined from the steady state data. The kinetic data also provided us with an important parameter in the discovery of selective and drug-like molecules; target residence time (τ). Target residence time, the reciprocal of $k_{off}$, is used differentiate between transient and long-lived ligand-protein complexes. Compounds that dissociate from target slowly would have longer τ, allowing less frequent administration of higher doses. Compound 7 has favorable binding kinetics to TTR with rapid on-rate and a slow off-rate (longer τ) ($k_{on}$=1.29×10$^6$±1.3×10$^5$ M$^{-1}$ s$^{-1}$ and $k_{off}$=0.026±0.001 s$^{-1}$). Ro 41-0960 also showed similar binding kinetics to those observed for IG3 ($K_d$=56.05±4.14 nM, $k_{on}$=2.35×10$^6$±1.5×10$^5$ M$^{-1}$ s$^{-1}$ and $k_{off}$=0.132±0.009 s$^{-1}$), though the $k_{off}$ was ~5× faster (FIG. 8A). In contrast, NSAIDs such as niflumic acid and diclofenac displayed a much faster dissociation form TTR ($k_{off}$=0.523 s$^{-1}$ and 1.01 s$^{-1}$, respectively) compared to 7 or Ro 41-0960 (~20× or 40× lower target residence time than 7) (FIGS. 8B and 8C).

Example 8

Heterobifunctional Compounds for PPI Disruption

Recruitment Moiety:

To target extracellular PPIs a number of extracellular proteins were examined. The abundant serum protein transthyretin (TTR) was selected as a presenter protein for inhibitors of extracellular receptor/ligand interactions. Transthyretin is a 55-kDa homotetrameric protein composed of four identical (3-sheet sandwich subunits. The TTR homotetrameric structure possesses 2,2,2 symmetry and is arranged as a dimer of dimers. TTR transports thyroxine (T4) and holoretinol binding protein (RBP) in the blood and in the cerebrospinal fluid (CSF) using non-overlapping binding sites [1]. The more labile dimer-dimer interface of the TTR tetramer creates two funnel-shaped T4 binding sites that are 99% unoccupied in the blood, because thyroid-binding globulin and albumin transport the vast majority of T4 in human blood [4]. TTR is desirable as an endogenous presenter protein for extracellular targets because: (1) TTR is present at a concentration of approximately 0.2 mg/mL (3.6 µM) in human plasma [13]; (2) TTR is an abundant protein in cerebrospinal fluid, present at approximately 10-fold lower concentration than in plasma [13]; (3) Several structurally diverse small molecules, including biaryls, flavones, phenoxazines and diarylamines have been found to bind to the same binding pocket that binds to T4 [14]. A fluorescence polarization (UP) assay was used to identify TTR ligands and to perform structure-activity relationship (SAR) analysis, as described above. The FP assay was then adapted for HTS and used to screen a ~120,000 member small molecule library for compounds that displaced the FP probe from the T4 binding of TTR. "Hits" were defined as compounds that induced at least 50% decrease in fluorescence polarization and demonstrated relative fluorescence between 70 and 130%. 200 compounds were designated as positive hits (0.167% hit rate). The 200 hits were then evaluated in a dose-response manner and their IC50 (compound concentration that resulted in 50% decrease in the FP signal) values were determined. The top 100 hits were then purchased and their IC50 was confirmed again in >10-point duplicate dose response FP assay. 32 compounds displayed an IC50<1 µM and the binding affinities of these compounds to TTR were evaluated using ITC and Surface Plasmon Resonance (SPR) (FIG. 5). The cytotoxicity of these compounds was evaluated and found that only one of the compounds was slightly toxic to primary cardiomyoctes and neurons (FIG. 6). HTS is also performed using a red-shifted dye (e.g., Cy3B) in labeling the FP TTR ligand instead of a FITC based ligand, for increased intensity and lifetime of approx. 2.9 ns.

Selection of the Linker.

Figure 9:
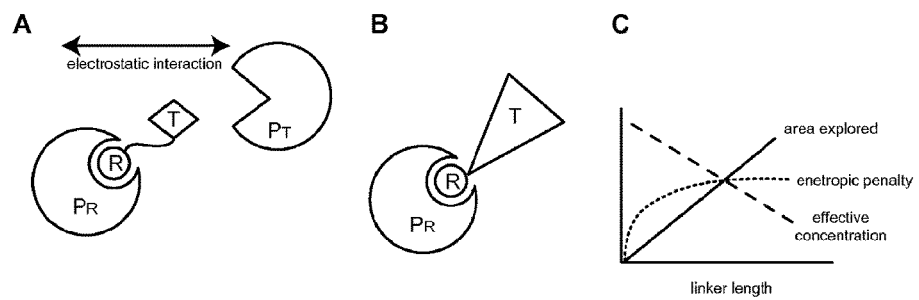
FIG. 9 depicts the selection of the linker of a subject heterobifunctional compound using computational chemistry. R and $P_R$ are a recruiting moiety and recruited protein respectively. T and $P_T$ are a targeting moiety and target protein, respectively.

The linker is selected considering the biophysical properties of the interacting proteins (Rp: recruited protein, and Tp: target protein). Given the bifunctional compound effectively acts to form a protein complex, the long-range forces that govern protein-protein interaction are considered when selecting an appropriate linker. The effect of the electrostatic interaction may be favorable, unfavourable or small (FIG. 9A). If the effect is small, the linker is selected to merely be long enough to project the targeting moiety (T) out of the binding pocket. If the interaction between Rp (recruited protein) and Tp (target protein) is disfavoured the linker is selected to be longer. The longer the linker (e.g., a flexible linker), the greater the area explored by the targeting element (FIG. 9B). Although this allows the targeting element to bind to the protein Tp, the effective concentration of the T decreases as the area explored increases. The flexibility of the linker also introduces an entropic cost for small flexible linkers, due to the restriction of conformational states in the final bifunctional complex. As the linker increases in length this penalty is reduced. Introduction of rigid elements into the linker restricts the conformational space explored by T, and provided it is sufficiently long allows it to project from the protein, with a reduced conformational penalty. Using a series of linker systems, a library of bifunctional molecules is prepared for a wide variety of interacting proteins.

Linkers of various length, hydrophilicity, and rigidity are used in the preparation of bifunctional compounds. The linkers are attached to activated functional groups on the small molecule targeting and recruitment moieties using any convenient organic coupling reactions (e.g., ester, amide, and ether bond formation reactions). The affinity of the recruitment complex is modeled using a computational tool (Ocker), and recruitment moieties having known crystal structures, where the tool overlays the common elements and produces an energetically favorable complex. Favorable positions for linker attachment are selected using the computational tool and crystal structures.

Selection of Targeting Moieties.

Any convenient small molecule binder of a target protein or target protein/receptor pair can be used. In addition, targeting moieties are identified by small molecule microarrays (SMM) screening for binding to the target protein using computational approaches [15]. The IL-2 antagonist Ro26-

4550 (IC50 3-6 µM) is a small molecule inhibitor of the target IL-2 (FIG. 10) [16]. The structure of IL-2 bound to the IL-2Rα (Kd≈10 nM) has been described [17] (FIG. 10). Analysis of the crystal structure shows that the IL-2Rα completely envelops the footprint covered by the small molecule competitive inhibitor. A linker is added to Ro26-4550 at a position that points away from IL2 (as determined by analysis of the X-ray crystal structures of IL-2 bound to the IL2Rα, IC50=10 nM, and Ro26-4550 bound to IL2, IC50=6 uM) and towards pointing away from IL2 and towards the IL2Rα. Ro26-4550 is covalently linked to a number of TTR ligands (FIG. 10). The attachment site for the linker on the TTR ligand is determined by the co-crystal structure of the ligand bound to TTR. Inhibition of IL2 to IL2Rα binding is determined using standard assays. In addition, the inhibition of IL2R activation is tested using cellular assays, such as IL2 dependent cell proliferation.

TNFα/TNFR1 interaction: A TNFα inhibitor that inhibits in vitro TNF receptor 1 (TNFR1) binding to TNF-α with an IC50 of 22 μM [18] is used as a targeting moiety in the bifunctional compounds. TNFα to TNFR1 binding assays are performed using standard protocols. In addition, simple cellular assays are performed, such as the inhibition of TNF-α mediated stimulation of inhibitor of NF-κB (IκB) degradation in HeLa cells compared to the orthogonal interleukin-1β (IL-1β)-mediated stimulation of the same pathway, to test the potency of the bifunctional compounds to inhibit the interaction between TNF-α and TNFR1.

REFERENCES

1. Monaco H. L.; Rizzi M.; Coda A. Science 1995, 268, 1039-41.
2. Choi S. H.; Leight S. N.; Lee V. M.; Li T.; Wong P. C.; Johnson J. A.; Saraiva M. J.; Sisodia S. S. J Neurosci. 2007, 27, 7006-10.
3. Buxbaum J. N.; Ye Z.; Reixach N.; Friske L.; Levy C.; Das P.; Golde T.; Masliah E.; Roberts A. R.; Bartfai T. *Proc Natl Acad Sci USA*. 2008, 105, 2681-6.
4. Johnson S. M.; Wiseman R. L.; Sekijima Y.; Green N. S.; Adamski-Werner S. L.; Kelly J. W. Acc Chem Res. 2005, 38, 911-21.
5. Suhr O. B.; Herlenius G.; Friman S.; Ericzon B. G. Liver Transpl. 2000, 6, 263-76.
6. Blake C. C.; Geisow M. J.; Oatley S. J.; Rérat B., Rérat C. J Mol Biol. 1978, 25, 339-56.
7. Adamski-Werner S. L.; Palaninathan S. K.; Sacchettini J. C.; Kelly J. W. J Med Chem. 2004, 47, 355-74.
8. Bartalena L.; Robbins J. Clin Lab Med. 1993, 3, 583-98.
9. Sekijima Y.; Kelly J. W.; Ikeda S. Curr Pharm Des. 2008, 14, 3219-30.
10. Chang L.; Munro S. L.; Richardson S. J.; Schreiber G. Eur J Biochem. 1999, 259, 534-42.
11. Wiseman R. L.; Johnson S. M.; Kelker M. S.; Foss T.; Wilson I. A.; Kelly J. W. J Am Chem Soc. 2005, 127, 5540-51.
12. Prapunpoj P.; Leelawatwatana L.; Schreiber G.; Richardson S. J. FEBS J. 2006, 273, 4013-23.
13. Aldred, A. R., C. M. Brack, and G. Schreiber, The cerebral expression of plasma protein genes in different species. Comp Biochem Physiol B Biochem Mol Biol, 1995. 111(1): p. 1-15.
14. Peterson, S. A., et al., Inhibiting transthyretin conformational changes that lead to amyloid fibril formation. Proc Natl Acad Sci USA, 1998. 95(22): p. 12956-60.
15. Koehler, A. N., A. F. Shamji, and S. L. Schreiber, Discovery of an inhibitor of a transcription factor using small molecule microarrays and diversity-oriented synthesis. J Am Chem Soc, 2003. 125(28): p. 8420-1.
16. Emerson, S. D., et al., NMR characterization of interleukin-2 in complexes with the IL-2Ralpha receptor component, and with low molecular weight compounds that inhibit the IL-2/IL-Ralpha interaction. Protein Sci, 2003. 12(4): p. 811-22.
17. Rickert, M., et al., The structure of interleukin-2 complexed with its alpha receptor. Science, 2005, 308(5727): p. 1477-80.
18. He, M. M., et al., Small-molecule inhibition of TNF-alpha. Science, 2005. 310(5750): p. 1022-5.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for screening a candidate compound for transthyretin (TTR) stabilizing activity, the method comprising:

a) contacting a TTR-fluorescence polarization (FP) probe complex with a candidate compound, wherein the TTR-FP probe complex comprises TTR and an FP probe, the FP probe comprises a ligand for TTR and a fluorescent moiety attached to the ligand for TTR by a linker, and the TTR-FP probe complex generates an FP signal; and b) determining the FP signal, wherein a decrease in the FP signal after addition of the candidate compound indicates the candidate compound stabilizes TTR.

2. The method of claim 1, wherein the TTR-FP probe complex is generated by contacting a sample comprising TTR with the FP probe.

3. The method of claim 1, wherein TTR in the TTR-FP probe complex is wild type TTR, a mutant TTR, or a combination thereof.

4. The method of claim 3, wherein TTR in the TTR-FP probe complex is wild type TTR.

5. The method of claim 3, wherein TTR in the TTR-FP probe complex is a mutant TTR.

6. The method of claim 5, wherein the mutant TTR includes at least one mutation selected from the group consisting of V1121, V30M, and L55P.

7. The method of claim 1, wherein the ligand for TTR is selected from the group consisting of diflunisal, diclofenac, tafamidis, and resveratrol.

8. The method of claim 1, wherein the ligand for TTR is NASID diclofenac analogue 3:

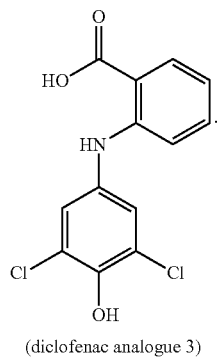 [SMILES: O=C(O)c1ccccc1Nc1cc(Cl)c(O)c(Cl)c1]

(diclofenac analogue 3)

9. The method of claim 1, wherein the linker is selected from the group consisting of polyethylene glycol (PEG), PEG amide, PED diamide, N,N-(1,2-aminoethyl), N,N-(2-{2-[2-(2-aminoethoxy)-ethoxyl]-ethoxy}-aminoethyl), N,N-[2-(2-aminoethoxy)-ethoxy]-aminoethyl), N,N-[2-(2-{2-[2-(2-aminoethoxy)-ethoxy]-ethylcarbamoyl}-ethyldisulfanyl)-aminoethyl], N,N-(amidoacetamido), N-[(5-{2-[2-(2-aminoethoxy)-ethoxy]-ethylcarbamoyl}-pentyl)-carboxamide], N-({5-[2-(2-aminoethyldisulfanyl)-ethylcarbamoyl]-pentyl})-carboxamide; N,N-[(5-aminopentyl)-thioureidyl], N-({2-[2-(2-aminoethoxy)-ethoxy]-ethyl}-carboxamide), and an alkyl linker, wherein the alkyl linker optionally includes one or more heteroatoms in the linker backbone.

10. The method of claim 1, wherein the linker is polyethylene glycol (PEG).

11. The method of claim 1, wherein the fluorescent moiety is selected from the group consisting of rhodamine, substituted rhodamine, fluorescein, fluorescein isothiocyanate, naphthofluorescein, dichlorotriazinylamine fluorescein, dansyl chloride, phycoerythrin, and umbelliferon.

12. The method of claim 1, wherein the fluorescent moiety is fluorescein isothiocyanate.

13. The method of claim 1, wherein the FP probe is the chemical structure shown below.

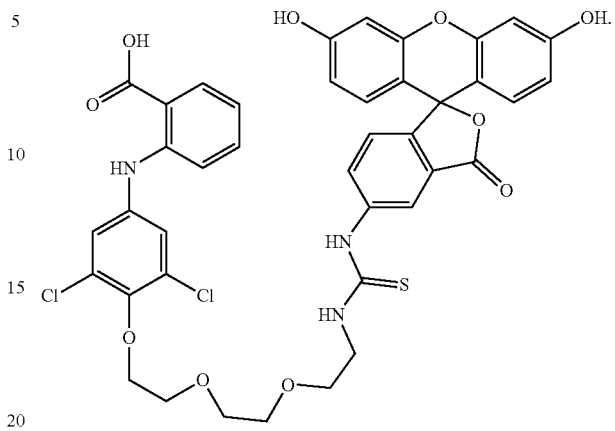

14. The method of claim 1, wherein the candidate compound is selected from the group consisting of an organic molecule, an inorganic molecule, and an organic molecule.

15. The method of claim 1, wherein the candidate compound is an organic molecule comprising an aromatic moiety.

16. The method of claim 1, wherein the candidate compound stabilizes TTR when there is at least a 10%, 20%, 30%, 40%, or 50% decrease in FP signal.

17. The method of claim 1, wherein the candidate compound stabilizes TTR when there is at least a 50% decrease in FP signal.

18. The method of claim 1, wherein the method for screening a candidate compound for TTR stabilizing activity is a high throughput screen (HTS) comprising a plurality of candidate compounds tested in parallel.

* * * * *